US008496928B2

(12) United States Patent
Verma et al.

(10) Patent No.: US 8,496,928 B2
(45) Date of Patent: Jul. 30, 2013

(54) METHOD FOR PREVENTING AND TREATING CARDIOVASCULAR DISEASES WITH BRCA1

(75) Inventors: Subodh Verma, Toronto (CA); Mohammed Al-Omran, Riyadh (SA)

(73) Assignees: St. Michael's Hospital, Toronto (CA); King Saud University, Riyadh (SA)

( * ) Notice: Subject to any disclaimer, the term of this patent is extended or adjusted under 35 U.S.C. 154(b) by 0 days.

(21) Appl. No.: 13/348,153

(22) Filed: Jan. 11, 2012

(65) Prior Publication Data

US 2012/0142762 A1    Jun. 7, 2012

Related U.S. Application Data

(63) Continuation of application No. 12/572,518, filed on Oct. 2, 2009, now Pat. No. 8,110,185.

(60) Provisional application No. 61/102,609, filed on Oct. 3, 2008.

(51) Int. Cl.
*A01N 63/00* (2006.01)
*A61K 48/00* (2006.01)

(52) U.S. Cl.
USPC ........................................ 424/93.7; 514/44 R

(58) Field of Classification Search
USPC ........................................ 424/93.7; 514/44 R
See application file for complete search history.

(56) References Cited

U.S. PATENT DOCUMENTS

| 5,578,461 | A | 11/1996 | Sherwin et al. | 435/69.1 |
|---|---|---|---|---|
| 5,747,282 | A | 5/1998 | Skolnick et al. | 435/69.1 |
| 2002/0102248 | A1 | 8/2002 | Chung | |
| 2006/0014839 | A1* | 1/2006 | Califf et al. | 514/789 |
| 2006/0154252 | A1 | 7/2006 | Marguerie et al. | 435/6 |
| 2009/0306159 | A1* | 12/2009 | Wulff et al. | 514/381 |

FOREIGN PATENT DOCUMENTS

| EP | 1321522 A1 | 6/2003 |
|---|---|---|
| KR | 2009048056 A | 5/2006 |
| WO | WO90/14092 | 11/1990 |
| WO | WO93/03222 A2 | 5/1993 |
| WO | WO94/12650 A2 | 6/1994 |
| WO | WO 02/04666 A2 | 1/2002 |
| WO | WO02/46466 A2 | 6/2002 |
| WO | WO 2004/042080 A1 | 5/2004 |
| WO | WO 2006/015127 A2 | 2/2006 |

OTHER PUBLICATIONS

Muller et al. Cardiovascular Research 70:70-78, 2006.*
Irminger-Finger et al. "Identification of BARD1 as Mediator Between Proapoptotic Stress and p53-Dependent Apoptosis" Molecular Cell 2001 vol. 8: 1255-1266.
Kenndey et al. "The Role of BRCA1 in the Cellular Response to Chemotherapy", Journal of the National Cancer Institute 2004 vol. 96 (22): 1659-1668.

Lee et al. "Identification of Marker Genes Related to Cardiovascular Toxicity of Doxorubicin and Daunorubicin in Human Unbilical Vein Endothelial Cells (HUVECS)" Molecular Cellular Toxicity 2007 vol. 3 (4) Sup. S, p. 51.
Shukla et al. "BRCA1 is an Essential Regulator of Cardiac Function" Circulation 2008 vol. 118 (2) Sup. 2, p. S534.
Singh et al. "BRCA1 Limits Inflammination Induced Apoptosis and Improves Endothelial Function: A Novel Role of DNA Repair Genes in Vascular Homestasis" Circulation 2008 vol. 118 (18) Sup. 2, p. S708
Taron et al. "BRCA1 mRNA Expression Levels as an Indicator of Chemoresistance in Lung Cancer" Human Molecular Genetics 2004 vol. 13 (20): 2443-2449.
International Search Report from PCT/CA2009/001382, Jan. 12, 2010.
Written Opinion from PCT/CA2009/001382, Jan. 12, 2010.
Abramson, B.L. and Buckell, V. "Canadian Cardivascular Scoiety Consensus: Peripheral Arterial Disease—Executive Summary" The Canadian Journal of Cardiology 2005 vol. 21 (12): 997-1006.
Bishopric et al. "Molecular Mechanisms of Apoptosis in the Cardiac Myocyte" Current Opinion in Pharmacology 2001 vol. 1: 141-150.
Bonini et al. "HSV-TK Gene Transfer into Donor Lymphocytes for Control of Allogeneic Graft-Versus-Leukemia" Science 1997 vol. 276: 1719-1724.
Bowie et al. "Deciphering the Message in Protein Sequences: Tolerance to Amino Acid Substitutions" Science 1990 vol. 247: 1306-1310.
Cavazzana-Calvo et al. "Gene Therapy of Human Severe Combined Immunodeficiency (SCID)-X1 Disease" Science 2000 vol. 288: 669-672.
Deng, C. and Brodie, S.G. "Roles of BRCA1 and its Interacting Proteins" BioEssaays 2000 vol. 22(8): 728-737.
Deng, C. and Wang, R. "Roles of BRCA1 in DNA Damage Repair: a Link Between Development and Cancer" Human Molecular Genetics 2003 vol. 12 (Review Issue 1): R113-123.
Dingwall, C. and Laskey, R.A. "Nuclear Targeting Sequences—a Consensus?" Trends in Biochemical Sciences 1991 vol. 16: 475-481.
Dorn, II, G.W. and Brown, J.H. "Gq Singaling in Cardiac Adaptation and Maladaptation" Trends in Cardiovascular Medicine 1999 vol. 9(1/2): 26-34.
Edelstein et al. "Gene Therapy Clinical Trails Worldwide to 2007—an Update" The Journal of Gene Medicine 2007 vol. 9: 833-842.
Evans et al. "Arthritis Gene Therapy's First Death" Arthritis Research & Therapy 2008 vol. 10: 110.
Fackenthal, J.D. and Olopade, O.I. "Breast Cancer Risk Associated with *BRCA1* and *BRCA2* in Diverse Populations" Nature Reviews 2007 7: 937-948.
Feuerstein, G.Z. "Apoptosis in Cardiac Diseases-New Opportunities for Novel Therapeutics for Heart Diseases" Cardiovacular Drugs and Therapy 1999 vol. 13: 289-294.
Ford et al. "Genetics Heterogeneity and Penetrance Analysis of the BRCA1 and BRCA2 Genes in Breast Cancer Families" The American Journal Human Genetics 1998 vol. 62: 676-689.

(Continued)

*Primary Examiner* — Marcia S Noble
(74) *Attorney, Agent, or Firm* — Licata & Tyrrell P.C.

(57) ABSTRACT

Methods for inhibiting cardiomyocyte apoptosis and/or to improving cardiac function and inhibiting inflammation-induced apoptosis in endothelial cells by delivering BRCA1 are provided. Such methods are useful in treatment and prevention of cardiovascular diseases.

21 Claims, 60 Drawing Sheets

OTHER PUBLICATIONS

Fuchs et al. "A Randomized, Double-Blind, Placebo-Controlled, Multicenter, Pilot Study of the Safety and Feasibility of Catheter-Based Intramyocradial Injection of AdVEGF121 in Patients with Refractory Advanced Coronary Artery Dieases" Catheterization and Cardiovascular Intervnetions 2006 vol. 68: 372-378.

Gilmore et al. "Role Played by BRCA1 in Regulatting the Cellular Response to Stress" Biochemical Society Transactions 2003 vol. 31 Part 1: 257-62.

Gong et al. "Retroviral Gene Transfer of Tissue-Type Plasminogen Activator Targets Thrombolysis In Vitro and In Vivio" Gene Therapy 2007 vol. 14: 1537-1542.

Gratton et al. "Cell-permeable Peptide Improve Cellular Uptake and Therapeutic Gene Delivery of Replication-Deficient Viruses in Cells and In Vivo" Nature Medicine 2003 vol. 9(3): 357-362.

Green et al. "Exercise and Cardiovasular Risk Reduction: Time to Update the Rationale for Exercise?" Journal of Applied Physiology 2008 vol. 105(2): 766-768.

Gregorevic et al. "Systemic Delivery of Genes to Striated Muscles Using Adeno-Associated Viral Vectors" Nature Medicine 2004 vol. 10(8): 828-834.

Hakem et al. "Developmental Studies of *Brca1* and *Brca2* Knock-Out Mice" Journal of Mammary Gland Biologu and Neoplasia 1998 vol. 3(4): 431-445.

Hao et al. "Myocardial Angiogenesis After Plasmid or Adenoviral VEGF-$A_{165}$ Gene Transfer in Rat Myocardial Infraction Model" Cardiovascular Research 2007 vol. 73: 481-487.

Rosamond et al, "Heart Disease and Stroke Statistics 2008 Update: A Report from the American Heart Association Statistics Committe and Stroke Statistics Subcommittee" Online Publication 2007: e25-e146 (http://cir.ahajounals.org/cgi/content/full/117/4/e25).

Hinohara et al. "Validation of Eight Genetic Risk Factors in East Asian Populations Replictaed the Association of *BRAP* with Coronary Artery Disease" Journal of Human Genetics 2009 vol. 54: 642-646.

Jessup, M. and Brozena, S.E. "Heart Failure" The New England Journal of Medicine 2003 vol. 3418 (20): 2007-2018.

Kalka, C. and Baumgartner, I. "Gene and Stem Cell Therapy in Peripheral Arterial Occlusive Disease" Vascular Medicine 2008 vol. 13: 157-172.

Kastrup et al. "Direct Intramyocardial Plasmid Vascular Endothelial Growth Factor-$A_{165}$ Gene Therapy in Patients with Stable Severe Angina Pectoris" Journal of American College of Cardiology 2005 vol. 45(7): 982-988.

Kim, C. and Beckles, G.L. "Cardiovascular Disease Risk Reducation in the Behavioral Risk Factor Surveillance System" American Journal of Preventive Medicine 2004 vol. 27(1): 1-7.

Kumar, D. and Jugdutt, B.I. "Apoptosis and Oxidants in the Heart" The Journal of Laboratory and Clinical Medicine 2003 vol. 142 (5): 288-267.

Kühnel et al. "Protein Transduction Domains Fused to Virus Receptors Improve Cellular Virus Uptake and Enhance Oncolysis by Tumor-Speciific Replicating Vectors" Journal of Virology 2004 78 (24): 13743-13754.

Laham et al. "Intracoronary Basic Fibroblast Growth Factor (FGF-2) in Patients with Severe Ischemic Heart Disease: Results of a Phase I Open-Label Dose Escalaiton Study" Journal of the American College of Cardiology 2000 vol. 36(7): 2132-2139.

Mekhail et al. "Identification of a Common Subnuclear Localization Signal" Molecular Biology of the Cell 2007 vol. 18: 3966-3977.

Menssen, A. and Hermeking , H. "Characterization of the c-MYC-Regulated Transcriptome by SAGE: Identification and Analysis of c-MYC Target Genes" The Proceedings of the National Academy of Sciences USA 2002 vol. 99(9): 6274-6279.

Morris et al. "Translocating Peptides and Proteins and Their Use for Gene Delivery" Current Opinion in Biotechnology 2000 vol. 11: 461-466.

Müller et al. "Targeting the Heart with Gene Therapy-Optimized Gene Delivery Methods" Cardiovascular Research 2007 vol. 73: 453-432.

Murray et al. "Role Played by BRCA1 in Transcriptional Regulation in Response to Therapy" Biochemical Society Transactions 2007 vol. 35 Part 5: 1342-1346.

Ozaki et al. "SNPs in *BRAP* Associated with Risk of Myocardial Infarction in Asian Population" Nature Genetics 2009 vol. 41(3): 329-333.

Park et al. "Efficient Lentiviral Transduction of Liver Requires Cell Cycling In Vivo" Nature Genetics 2000 vol. 24: 49-552.

Ripa et al. "Intramyocardial Injection of Vascular Endothelial Growth Factor-$A_{165}$ Plasmid Followed by Granulocyte-Colony Stimulating Factors to Induce Angiogenesis in Patients with Severe Chronic Ischaemic Heart Disease" European Heart Journal 2006 vol. 27: 1785-1792.

Schott et al. "Pressue Overload and Neurohumoral Activation Differentially Affect the Myocardial Proteome" Proteomics 2005 5: 1372-1381.

Scully, R. and Livingston, D.M. "In Search of the Tumor-Suppressor Funtions of BRCA1 and BRCA2" Nature 2000 vol. 408: 429-432.

Scully et al. "Genetic Analysis of BRCA1 Function in a Defined Tumor Cell Line" Molecular Cell 1999 4: 1093-1099.

Shukla et al. "BRCA1 is an Essential Regulator of Cardiac Function" Canadian Journal of Cardiology 2008 vol. 24 (Suppl E): 217E abstract.

Shukla et al. "BRCA1 is a Novel and Essential Regulator of Cardiac Function" Canadian Journal of Cardiology 2009 vol. 25 (Suppl B): 535 abstract.

Shukla et al. "BRCA1 is an Essential Regulator of Cardiac Function" Circulation Research 2009 vol. 105: e15 (P22) abstract.

Shukla et al. "Abstract 3695: BRCA1 is a Novel Modulator of Cardiac Substrate Metabolism and Restores Cardiac Function in Response to Ischemic and Genotoxic Stressors" Circulation 2009 vol. 120: S850-851.

Singh et al. "BRCA1 Protects Against Inflammation-Induced Apoptosis and Improves Endothelial Function by Activation of AKT and ENOS: A Novel Role for BRCA1 in Vascular Homeostasis" Canadian Journal of Cardiology 2009 vol. 25 (Suppl B): 193 abstract.

Singh et al. "Abstract 4219: BRCA1 is a Novel Regulator of Endothelial Function and Limits Atherosclerosis" Circulation 2009 vol. 120: S928.

Singh et al. "BRCA1 Attenuates Inflammation Indued Apoptosis and Restores Endothelial Function: A Novel Role of BRCA1 in Vascular Homeostasis" Journal of the American College of Cardiology 2009 vol. 53 (Supplement A): 432 (1022-123) abstract.

Smith et al. "ACC/AHA Guidelines for Percutaneous Coronory Intervention (Revision of the 1993 PTCA Guidelines)—Executive Summary" Circulation 2001 vol. 103: 3019-3041.

Smith , T.F. and Waterman, M.S. "Comparison of Biosequences" Advances in Applied Mathematics 1981 vol. 2: 482-489.

Somasundaram et al. "BRCA1 Signals ARF-Dependent Stabilization and Coactivation of p53" Oncogene 1999 18: 6605-6614.

Stewart et al. "Angiogenic Gene Therapy in Patients with Nonrevascularizable Ischemic Heart Disease: a Phase 2 Randomized, Controlled Trial of $AdVEGF_{121}$ (AdVEGF121) Versus Maximun Medical Treatment" Gene Therapy 2006 vol. 13: 1503-1511.

Symes et al. "Gene Therapy with Vascular Endothelial Growth Factor for Inoperable Coronary Artery Disease" The Annals of Thoracic Surgery 1999 vol. 68: 830-837.

Xu et al. "Genetic Interactions Between Tumor Suppressors Brca1 and p53 in Apoptosis, Cell Cycle and Tumorigenesis" Nature Genetics 2001 vol. 28: 266-271.

Xu et al. "Conditional Mutation of Brca1 in Mammary Epithelial Cells Results in Blunted Ductal Morphogenesis and Tumor Formation" Nature Genetics 1999 vol. 22: 37-43.

Schimmel et al. Cancer Treatment Reviews 30:181-191, 2004.

Gautam et al., Am J. Respir Med 1(1): 35-46, 2002.

Tomasoni and Benigni, Current Gene Therapy 4: 115-122, 2004.

Yang, Radiology 228: 36-49, 2003.

\* cited by examiner

Products of 004 and 006

Products of 004 and 005

SEQUENCE LISTING

<160> NUMBER OF SEQ ID NOS: 33

<210> SEQ ID NO 1
<211> LENGTH: 7191
<212> TYPE: DNA
<213> ORGANISM: Homo sapien

<400> SEQUENCE: 1

```
cttagcggta gcccttggt ttccgtggca acggaaaagc gcgggaatta cagataaatt      60
aaaactgcga ctgcgcggcg tgagctcgct gagacttcct ggacggggga caggctgtgg     120
ggtttctcag ataactgggc ccctgcgctc aggaggcctt caccctctgc tctgggtaaa     180
gttcattgga acagaaagaa atggatttat ctgctcttcg cgttgaagaa gtacaaaatg     240
tcattaatgc tatgcagaaa atcttagagt gtcccatctg tctggagttg atcaaggaac     300
ctgtctccac aaagtgtgac cacatatttt gcaaattttg catgctgaaa cttctcaacc     360
agaagaaagg gccttcacag tgtcctttat gtaagaatga tataaccaaa aggagcctac     420
aagaaagtac gagatttagt caacttgttg aagagctatt gaaaatcatt tgtgcttttc     480
agcttgacac aggtttggag tatgcaaaca gctataattt tgcaaaaaag gaaaataact     540
ctcctgaaca tctaaaagat gaagtttcta tcatccaaag tatgggctac agaaaccgtg     600
ccaaaagact tctacagagt gaacccgaaa atccttcctt gcaggaaacc agtctcagtg     660
tccaactctc taaccttgga actgtgagaa ctctgaggac aaagcagcgg atacaacctc     720
aaaagacgtc tgtctacatt gaattgggat ctgattcttc tgaagatacc gttaataagg     780
caacttattg cagtgtggga gatcaagaat tgttacaaat caccctcaa ggaaccaggg     840 atgaaatcag tttggattct gcaaaaaagg ctgcttgtga attttctgag acggatgtaa     900
caaatactga acatcatcaa cccagtaata atgatttgaa caccactgag aagcgtgcag     960
ctgagaggca tccagaaaag tatcagggta gttctgtttc aaacttgcat gtggagccat    1020
gtggcacaaa tactcatgcc agctcattac agcatgagaa cagcagttta ttactcacta    1080
aagacagaat gaatgtagaa aaggctgaat tctgtaataa agcaaacag cctggcttag    1140 caaggagcca acataacaga tgggctgaa gtaaggaaac atgtaatgat aggcggactc    1200
ccagcacaga aaaaaggta gatctgaatg ctgatcccct gtgtgagaga aaagaatgga    1260
ataagcagaa actgccatgc tcagagaatc ctagagatac tgaagatgtt ccttggataa    1320
cactaaatag cagcattcag aaagttaatg agtggttttc cagaagtgat gaactgttag    1380
gttctgatga ctcacatgat ggggagtctg aatcaaatgc caaagtagct gatgtattgg    1440
acgttctaaa tgaggtagat gaatattctg gttcttcaga gaaatagac ttactggcca    1500 gtgatcctca tgaggcttta atatgtaaaa gtgaaagagt tcactccaaa tcagtagaga    1560
gtaatattga agacaaaata tttgggaaaa cctatcggaa gaaggcaagc ctccccaact    1620
taagccatgt aactgaaaat ctaattatag gagcatttgt tactgagcca cagataatac    1680
```

```
aagagcgtcc cctcacaaat aaattaaagc gtaaaaggag acctacatca ggccttcatc      1740
ctgaggattt tatcaagaaa gcagatttgg cagttcaaaa gactcctgaa atgataaatc      1800
agggaactaa ccaaacggag cagaatggtc aagtgatgaa tattactaat agtggtcatg      1860
agaataaaac aaaaggtgat tctattcaga atgagaaaaa tcctaaccca atagaatcac      1920
tcgaaaaaga atctgctttc aaaacgaaag ctgaacctat aagcagcagt ataagcaata      1980
tggaactcga attaaatatc cacaattcaa agcacctaa aaagaatagg ctgaggagga       2040
agtcttctac caggcatatt catgcgcttg aactagtagt cagtagaaat ctaagcccac      2100
ctaattgtac tgaattgcaa attgatagtt gttctagcag tgaagagata agaaaaaaaa      2160
agtacaacca aatgccagtc aggcacagca gaaacctaca actcatggaa ggtaaagaac      2220
ctgcaactgg agccaagaag agtaacaagc caaatgaaca gacaagtaaa agacatgaca      2280
gcgatacttt cccagagctg aagttaacaa atgcacctgg ttctttact aagtgttcaa       2340 ataccagtga acttaaagaa tttgtcaatc ctagccttcc aagagaagaa aaagaagaga      2400
aactagaaac agttaaagtg tctaataatg ctgaagaccc caaagatctc atgttaagtg      2460
gagaaagggt tttgcaaact gaaagatctg tagagagtag cagtatttca ttggtacctg      2520
gtactgatta tggcactcag gaaagtatct cgttactgga agttagcact ctagggaagg      2580
caaaaacaga accaaataaa tgtgtgagtc agtgtgcagc atttgaaaac cccaagggac      2640
taattcatgg ttgttccaaa gataatagaa atgacacaga aggctttaag tatccattgg      2700
gacatgaagt taaccacagt cgggaaacaa gcatagaaat ggaagaaagt gaacttgatg      2760
ctcagtattt gcagaataca ttcaaggttt caaagcgcca gtcatttgct ccgttttcaa      2820
atccaggaaa tgcagaagag gaatgtgcaa cattctctgc ccactctggg tccttaaaga      2880
aacaaagtcc aaaagtcact tttgaatgtg aacaaaagga agaaaatcaa ggaaagaatg      2940
agtctaatat caagcctgta cagacagtta atatcactgc aggctttcct gtggttggtc      3000
agaaagataa gccagttgat aatgccaaat gtagtatcaa aggaggctct aggttttgtc      3060
tatcatctca gttcagaggc aacgaaactg gactcattac tccaaataaa catggacttt      3120
tacaaaaccc atatcgtata ccaccacttt ttcccatcaa gtcatttgtt aaaactaaat      3180
gtaagaaaaa tctgctagag gaaaactttg aggaacattc aatgtcacct gaaagagaaa      3240
tgggaaatga gaacattcca agtacagtga gcacaattag ccgtaataac attagagaaa      3300
atgtttttaa agaagccagc tcaagcaata ttaatgaagt aggttccagt actaatgaag      3360
tgggctccag tattaatgaa ataggttcca gtgatgaaaa cattcaagca gaactaggta      3420
gaaacagagg gccaaaattg aatgctatgc ttagattagg ggttttgcaa cctgaggtct      3480
ataaacaaag tcttcctgga agtaattgta agcatcctga ataaaaaag caagaatatg      3540 aagaagtagt tcagactgtt aatacagatt tctctccata tctgatttca gataacttag      3600
aacagcctat gggaagtagt catgcatctc aggtttgttc tgagcaccct gatgacctgt      3660
tagatgatgg tgaaataaag gaagatacta gttttgctga aaatgacatt aaggaaagtt      3720
ctgctgtttt tagcaaaagc gtccagaaag gagagcttag caggagtcct agcccttca       3780 cccatacaca tttggctcag ggttaccgaa gaggggccaa gaattagag tcctcagaag        3840 agaacttatc tagtgaggat gaagagcttc cctgcttcca acacttgtta tttggtaaag      3900
taaacaatat accttctcag tctactaggc atagcaccgt tgctaccgag tgtctgtcta      3960
agaacacaga ggagaattta ttatcattga agaaatagctt aaatgactgc agtaaccagg     4020
taatattggc aaaggcatct caggaacatc accttagtga ggaaacaaaa tgttctgcta      4080
```

```
gcttgttttc ttcacagtgc agtgaattgg aagacttgac tgcaaataca acacccagg    4140 atcctttctt gattggttct tccaaacaaa tgaggcatca gtctgaaagc cagggagttg    4200
gtctgagtga caaggaattg gtttcagatg atgaagaaag aggaacgggc ttggaagaaa    4260
ataatcaaga agagcaaagc atggattcaa acttaggtga agcagcatct gggtgtgaga    4320
gtgaaacaag cgtctctgaa gactgctcag ggctatcctc tcagagtgac attttaacca    4380
ctcagcagag ggataccatg caacataacc tgataaagct ccagcaggaa atggctgaac    4440
tagaagctgt gttagaacag catgggagcc agccttctaa cagctaccct tccatcataa    4500
gtgactcttc tgcccttgag gacctgcgaa atccagaaca agcacatca gaaaaagcag     4560 tattaacttc acagaaaagt agtgaatacc ctataagcca gaatccagaa ggcctttctg    4620
ctgacaagtt tgaggtgtct gcagatagtt ctaccagtaa aaataaagaa ccaggagtgg    4680
aaaggtcatc cccttctaaa tgcccatcat tagatgatag gtggtacatg cacagttgct    4740
ctgggagtct tcagaataga aactacccat ctcaagagga gctcattaag gttgttgatg    4800
tggaggagca acagctggaa gagtctgggc cacacgattt gacggaaaca tcttacttgc    4860
caaggcaaga tctagaggga accccttacc tggaatctgg aatcagcctc ttctctgatg    4920
accctgaatc tgatccttct gaagacagag ccccagagtc agctcgtgtt ggcaacatac    4980
catcttcaac ctctgcattg aaagttcccc aattgaaagt tgcagaatct gcccagagtc    5040
cagctgctgc tcatactact gatactgctg gtataatgc aatggaagaa agtgtgagca    5100
gggagaagcc agaattgaca gcttcaacag aaagggtcaa caaaagaatg tccatggtgg    5160
tgtctggcct gaccccagaa gaatttatgc tcgtgtacaa gtttgccaga aaacaccaca    5220
tcactttaac taatctaatt actgaagaga ctactcatgt tgttatgaaa acagatgctg    5280
agtttgtgtg tgaacggaca ctgaaatatt ttctaggaat tgcgggagga aaatgggtag    5340
ttagctattt ctgggtgacc cagtctatta agaaagaaa aatgctgaat gagcatgatt    5400
ttgaagtcag aggagatgtg gtcaatggaa gaaaccacca aggtccaaag cgagcaagag    5460
aatcccagga cagaaagatc ttcaggggc tagaaatctg ttgctatggg cccttcacca    5520
acatgcccac agatcaactg gaatggatgg tacagctgtg tggtgcttct gtggtgaagg    5580
agctttcatc attcacccTT ggcacaggtg tccacccaat tgtggttgtg cagccagatg    5640
cctggacaga ggacaatggc ttccatgcaa ttgggcagat gtgtgaggca cctgtggtga    5700
cccgagagtg ggtgttggac agtgtagcac tctaccagtg ccaggagctg acacctacc    5760 tgataccca gatcccccac agccactact gactgcagcc agccacaggt acagagccac    5820
aggaccccaa gaatgagctt acaaagtggc cttccaggc cctgggagct cctctcactc    5880
ttcagtcctt ctactgtcct ggctactaaa tattttatgt acatcagcct gaaaaggact    5940
tctggctatg caagggtccc ttaaagattt tctgcttgaa gtctcccttg gaaatctgcc    6000
atgagcacaa aattatggta attttttcacc tgaagaagatt ttaaaaccat ttaaacgcca    6060
ccaattgagc aagatgctga ttcattattt atcagcccta ttctttctat tcaggctgtt    6120
gttggcttag ggctggaagc acagagtggc ttggcctcaa gagaatagct ggtttcccta    6180
agtttacttc tctaaaaccc tgtgttcaca aaggcagaga gtcagaccct tcaatggaag    6240
gagagtgctt gggatcgatt atgtgactta aagtcagaat agtccttggg cagttctcaa    6300
atgttggagt ggaacattgg ggaggaaatt ctgaggcagg tattagaaat gaaaaggaaa    6360
cttgaaacct gggcatggtg gctcacgcct gtaatcccag cactttggga ggccaaggtg    6420
ggcagatcac tggaggtcag gagttcgaaa ccagcctggc caacatggtg aaaccccatc    6480
```

```
tctactaaaa atacagaaat tagccggtca tggtggtgga cacctgtaat cccagctact      6540
caggtggcta aggcaggaga atcacttcag cccgggaggt ggaggttgca gtgagccaag      6600
atcataccac ggcactccag cctgggtgac agtgagactg tggctcaaaa aaaaaaaaaa      6660
aaaaaggaaa atgaaactag aagagatttc taaaagtctg agatatattt gctagatttc      6720
taaagaatgt gttctaaaac agcagaagat tttcaagaac cggtttccaa agacagtctt      6780
ctaattcctc attagtaata agtaaaatgt ttattgttgt agctctggta tataatccat      6840
tcctcttaaa atataagacc tctggcatga atatttcata tctataaaat gacagatccc      6900
accaggaagg aagctgttgc tttctttgag gtgattttt  tccttt gctc cctgttgctg       6960 aaaccataca gcttcataaa taattttgct tgctgaagga agaaaagtg ttttt cataa        7020 acccattatc caggactgtt tatagctgtt ggaaggacta ggtcttccct agcccccca       7080 gtgtgcaagg gcagtgaaga cttgattgta caaaatacgt tttgtaaatg ttgtgctgtt      7140
aacactgcaa ataaacttgg tagcaaacac ttcaaaaaaa aaaaaaaaa  a              7191
```

<210> SEQ ID NO 2
<211> LENGTH: 7388
<212> TYPE: DNA
<213> ORGANISM: Homo sapien

<400> SEQUENCE: 2

```
ggcagtttgt aggtcgcgag ggaagcgctg aggatcagga agggggcact gagtgtccgt        60
gggggaatcc tcgtgatagg aactggaata tgccttgagg gggacactat gtctttaaaa      120
acgtcggctg gtcatgaggt caggagttcc agaccagcct gaccaacgtg gtgaaactcc      180
gtctctacta aaaatacaaa aattagccgg gcgtggtgcc gctccagcta ctcaggaggc      240
tgaggcagga gaatcgctag aacccgggag gcggaggttg cagtgagccg agatcgcgcc      300
attgcactcc agcctgggcg acagagcgag actgtctcaa aacaaaacaa aacaaaacaa      360
aacaaaaaac accggctgtt cattggaaca gaaagaaatg gatttatctg ctcttcgcgt      420
tgaagaagta caaaatgtca ttaatgctat gcagaaaatc ttagagtgtc ccatctgtct      480
ggagttgatc aaggaacctg tctccacaaa gtgtgaccac atattttgca aattttgcat      540
gctgaaactt ctcaaccaga gaaagggcc  ttcacagtgt cctttatgta agaatgatat      600
aaccaaaagg agcctacaag aaagtacgag atttagtcaa cttgttgaag agctattgaa       660
aatcatttgt gcttttcagc ttgacacagg tttggagtat gcaaacagct ataattttgc      720
aaaaaaggaa ataactctc  ctgaacatct aaaagatgaa gtttctatca tccaaagtat       780
gggctacaga aaccgtgcca aaagacttct acagagtgaa cccgaaaatc cttccttgca      840 ggaaccagt  ctcagtgtcc aactctctaa ccttggaact gtgagaactc tgaggacaaa       900
gcagcggata caacctcaaa agacgtctgt ctacattgaa ttgggatctg attcttctga      960
agataccgtt aataaggcaa cttattgcag tgtgggagat caagaattgt tacaaatcac     1020
ccctcaagga accagggatg aaatcagttt ggattctgca aaaaaggctg cttgtgaatt     1080
ttctgagacg gatgtaacaa atactgaaca tcatcaaccc agtaataatg atttgaacac     1140
cactgagaag cgtgcagctg agaggcatcc agaaaagtat cagggtagtt ctgtttcaaa     1200
cttgcatgtg gagccatgtg gcacaaatac tcatgccagc tcattacagc atgagaacag     1260
cagtttatta ctcactaaag acagaatgaa tgtagaaaag gctgaattct gtaataaaag     1320
caaacagcct ggcttagcaa ggagccaaca taacagatgg gctggaagta aggaaacatg     1380
taatgatagg cggactccca gcacagaaaa aaaggtagat ctgaatgctg atcccctgtg     1440
```

```
tgagagaaaa gaatggaata agcagaaact gccatgctca gagaatccta gagatactga    1500
agatgttcct tggataacac taaatagcag cattcagaaa gttaatgagt ggttttccag    1560
aagtgatgaa ctgttaggtt ctgatgactc acatgatggg gagtctgaat caaatgccaa    1620
agtagctgat gtattggacg ttctaaatga ggtagatgaa tattctggtt cttcagagaa    1680
aatagactta ctggccagtg atcctcatga ggctttaata tgtaaaagtg aaagagttca    1740
ctccaaatca gtagagagta atattgaaga caaaatattt gggaaaacct atcggaagaa    1800
ggcaagcctc cccaacttaa gccatgtaac tgaaaatcta attataggag catttgttac    1860
tgagccacag ataatacaag agcgtccccct cacaaataaa ttaaagcgta aaaggagacc    1920
tacatcaggc cttcatcctg aggattttat caagaaagca gatttggcag ttcaaaagac    1980
tcctgaaatg ataaatcagg gaactaacca aacggagcag aatggtcaag tgatgaatat    2040
tactaatagt ggtcatgaga ataaaacaaa aggtgattct attcagaatg agaaaaatcc    2100
taacccaata gaatcactcg aaaagaatc tgctttcaaa acgaaagctg aacctataag    2160
cagcagtata agcaatatgg aactcgaatt aaatatccac aattcaaaag cacctaaaaa    2220
gaataggctg aggaggaagt cttctaccag gcatattcat gcgcttgaac tagtagtcag    2280
tagaaatcta agcccaccta attgtactga attgcaaatt gatagttgtt ctagcagtga    2340
agagataaag aaaaaaaagt acaaccaaat gccagtcagg cacagcagaa acctacaact    2400
catggaaggt aaagaacctg caactggagc caagaagagt aacaagccaa atgaacagac    2460
aagtaaaaga catgacagcg atactttccc agagctgaag ttaacaaatg cacctggttc    2520
ttttactaag tgttcaaata ccagtgaact taaagaattt gtcaatccta gccttccaag    2580
agaagaaaaa gaagagaaac tagaaacagt taaagtgtct aataatgctg aagaccccaa    2640
agatctcatg ttaagtggag aaagggtttt gcaaactgaa agatctgtag agagtagcag    2700
tatttcattg gtacctggta ctgattatgg cactcaggaa agtatctcgt tactggaagt    2760
tagcactcta gggaaggcaa aaacagaacc aaataaatgt gtgagtcagt gtgcagcatt    2820
tgaaaacccc aagggactaa ttcatggttg ttccaaagat aatagaaatg acacagaagg    2880
ctttaagtat ccattgggac atgaagttaa ccacagtcgg gaaacaagca tagaaatgga    2940
agaaagtgaa cttgatgctc agtatttgca gaatacattc aaggtttcaa agcgccagtc    3000
atttgctccg ttttcaaatc caggaaatgc agaagaggaa tgtgcaacat ctctgcccca    3060
ctctgggtcc ttaaagaaac aaagtccaaa agtcactttt gaatgtgaac aaaaggaaga    3120
aaatcaagga aagaatgagt ctaatatcaa gcctgtacag acagttaata tcactgcagg    3180
ctttcctgtg gttggtcaga agataagcc agttgataat gccaaatgta gtatcaaagg    3240
aggctctagg ttttgtctat catctcagtt cagaggcaac gaaactggac tcattactcc    3300
aaataaacat ggacttttac aaaacccata tcgtatacca ccacttttc ccatcaagtc    3360 atttgttaaa actaaatgta agaaaaatct gctagaggaa actttgagg aacattcaat    3420 gtcacctgaa agagaaatgg gaaatgagaa cattccaagt acagtgagca caattagccg    3480
taataacatt agagaaaatg ttttaaaga agccagctca agcaatatta atgaagtagg    3540
ttccagtact aatgaagtgg gctccagtat taatgaaata ggttccagtg atgaaaacat    3600
tcaagcagaa ctaggtagaa acagagggcc aaaattgaat gctatgctta gattagggt    3660 tttgcaacct gaggtctata aacaaagtct tcctggaagt aattgtaagc atcctgaaat    3720
aaaaaagcaa gaatatgaag aagtagttca gactgttaat acagatttct ctccatatct    3780
gatttcagat aacttagaac agcctatggg aagtagtcat gcatctcagg tttgttctga    3840
```

```
gacacctgat gacctgttag atgatggtga aataaaggaa gatactagtt ttgctgaaaa    3900
tgacattaag gaaagttctg ctgttttag caaaagcgtc cagaaaggag agcttagcag    3960
gagtcctagc cctttcaccc atacacattt ggctcagggt taccgaagag gggccaagaa    4020
attagagtcc tcagaagaga acttatctag tgaggatgaa gagcttccct gcttccaaca    4080 cttgttatt ggtaaagtaa acaatatacc ttctcagtct actaggcata gcaccgttgc    4140
taccgagtgt ctgtctaaga acacagagga gaatttatta tcattgaaga atagcttaaa    4200
tgactgcagt aaccaggtaa tattggcaaa ggcatctcag gaacatcacc ttagtgagga    4260
aacaaaatgt tctgctagct tgttttcttc acagtgcagt gaattggaag acttgactgc    4320
aaatacaaac acccaggatc cttcttgat tggttcttcc aaacaaatga ggcatcagtc    4380
tgaaagccag ggagttggtc tgagtgacaa ggaattggtt tcagatgatg aagaaagagg    4440
aacgggcttg gaagaaaata atcaagaaga gcaaagcatg gattcaaact taggtgaagc    4500
agcatctggg tgtgagagtg aaacaagcgt ctctgaagac tgctcagggc tatcctctca    4560
gagtgacatt ttaaccactc agcagaggga taccatgcaa cataacctga taaagctcca    4620
gcaggaaatg gctgaactag aagctgtgtt agaacagcat gggagccagc cttctaacag    4680
ctacccttcc atcataagtg actcttctgc ccttgaggac ctgcgaaatc cagaacaaag    4740
cacatcagaa aaagcagtat taacttcaca gaaaagtagt gaataccctaa taagccagaa    4800 tccagaaggc ctttctgctg acaagtttga ggtgtctgca gatagttcta ccagtaaaaa    4860
taaagaacca ggagtggaaa ggtcatcccc ttctaaatgc ccatcattag atgataggtg    4920
gtacatgcac agttgctctg ggagtcttca gaatagaaac tacccatctc aagaggagct    4980
cattaaggtt gttgatgtgg aggagcaaca gctggaagag tctgggccac acgatttgac    5040
ggaaacatct tacttgccaa ggcaagatct agagggaacc ccttacctgg aatctggaat    5100
cagcctcttc tctgatgacc ctgaatctga tccttctgaa gacagagccc cagagtcagc    5160
tcgtgttggc aacataccat cttcaacctc tgcattgaaa gttccccaat tgaaagttgc    5220
agaatctgcc cagagtccag ctgctgctca tactactgat actgctgggt ataatgcaat    5280
ggaagaaagt gtgagcaggg agaagccaga attgacagct tcaacagaaa gggtcaacaa    5340
aagaatgtcc atggtggtgt ctggcctgac cccagaagaa tttatgctcg tgtacaagtt    5400
tgccagaaaa caccacatca ctttaactaa tctaattact gaagagacta ctcatgttgt    5460
tatgaaaaca gatgctgagt ttgtgtgtga acggacactg aaatattttc taggaattgc    5520
gggaggaaaa tgggtagtta gctatttctg ggtgacccag tctattaaag aaagaaaat    5580 gctgaatgag catgatttg aagtcagagg agatgtggtc aatggaagaa accaccaagg    5640
tccaaagcga gcaagagaat cccaggacag aaagatcttc aggggctag aaatctgttg    5700 ctatgggccc ttcaccaaca tgcccacaga tcaactggaa tggatggtac agctgtgtgg    5760
tgcttctgtg gtgaaggagc tttcatcatt caccttggc acaggtgtcc acccaattgt    5820
ggttgtgcag ccagatgcct ggacagagga caatggcttc catgcaattg gcagatgtg    5880 tgaggcacct gtggtgaccc gagagtgggg gttggacagt gtagcactct accagtgcca    5940
ggagctggac acctacctga tacccccagat ccccacagc cactactgac tgcagccagc    6000
cacaggtaca gagccacagg accccaagaa tgagcttaca aagtggcctt tccaggccct    6060
gggagctcct ctcactcttc agtccttcta ctgtcctggc tactaaatat tttatgtaca    6120
tcagcctgaa aaggacttct ggctatgcaa gggtccctta aagattttct gcttgaagtc    6180
tcccttggaa atctgccatg agcacaaaat tatggtaatt tttcacctga aagattta    6240
```

| | | |
|---|---|---|
| aaaccattta aacgccacca attgagcaag atgctgattc attatttatc agccctattc | 6300 | |
| tttctattca ggctgttgtt ggcttagggc tggaagcaca gagtggcttg gcctcaagag | 6360 | |
| aatagctggt ttccctaagt ttacttctct aaaaccctgt gttcacaaag gcagagagtc | 6420 | |
| agacccttca atggaaggag agtgcttggg atcgattatg tgacttaaag tcagaatagt | 6480 | |
| ccttgggcag ttctcaaatg ttggagtgga acattgggga ggaaattctg aggcaggtat | 6540 | |
| tagaaatgaa aaggaaactt gaaacctggg catggtggct cacgcctgta atcccagcac | 6600 | |
| tttgggaggc caaggtgggc agatcactgg aggtcaggag ttcgaaacca gcctggccaa | 6660 | |
| catggtgaaa ccccatctct actaaaaata cagaaattag ccggtcatgg tggtggacac | 6720 | |
| ctgtaatccc agctactcag gtggctaagg caggagaatc acttcagccc gggaggtgga | 6780 | |
| ggttgcagtg agccaagatc ataccacggc actccagcct gggtgacagt gagactgtgg | 6840 | |
| ctcaaaaaaa aaaaaaaaa aaggaaaatg aaactagaag agatttctaa aagtctgaga | 6900 | |
| tatatttgct agatttctaa agaatgtgtt ctaaaacagc agaagatttt caagaaccgg | 6960 | |
| tttccaaaga cagtcttcta attcctcatt agtaataagt aaaatgttta ttgttgtagc | 7020 | |
| tctggtatat aatccattcc tcttaaaata taagacctct ggcatgaata tttcatatct | 7080 | |
| ataaaatgac agatcccacc aggaaggaag ctgttgcttt ctttgaggtg attttttttcc | 7140 | |
| tttgctccct gttgctgaaa ccatacagct tcataaataa ttttgcttgc tgaaggaaga | 7200 | |
| aaaagtgttt ttcataaacc cattatccag gactgtttat agctgttgga aggactaggt | 7260 | |
| cttccctagc cccccccagtg tgcaaggggca gtgaagactt gattgtacaa aatacgtttt | 7320 | |
| gtaaatgttg tgctgttaac actgcaaata aacttggtag caaacacttc aaaaaaaaaa | 7380 | |
| aaaaaaaa | 7388 | |

<210> SEQ ID NO 3
<211> LENGTH: 7185
<212> TYPE: DNA
<213> ORGANISM: Homo sapien

<400> SEQUENCE: 3

| | | |
|---|---|---|
| cttagcggta gcccccttggt ttccgtggca acggaaaagc gcgggaatta cagataaatt | 60 | |
| aaaactgcga ctgcgcggcg tgagctcgct gagacttcct ggacggggga caggctgtgg | 120 | |
| ggtttctcag ataactgggc ccctgcgctc aggaggcctt caccctctgc tctggttcat | 180 | |
| tggaacagaa agaaatggat ttatctgctc ttcgcgttga agaagtacaa aatgtcatta | 240 | |
| atgctatgca gaaaatctta gagtgtccca tctgtctgga gttgatcaag gaacctgtct | 300 | |
| ccacaaagtg tgaccacata ttttgcaaat tttgcatgct gaaacttctc aaccagaaga | 360 | |
| aagggccttc acagtgtcct ttatgtaaga atgatataac caaaaggagc ctacaagaaa | 420 | |
| gtacgagatt tagtcaactt gttgaagagc tattgaaaat catttgtgct tttcagcttg | 480 | |
| acacaggttt ggagtatgca aacagctata ttttgcaaaa aaggaaaaat aactctcctg | 540 | |
| aacatctaaa agatgaagtt tctatcatcc aaagtatggg ctacagaaac cgtgccaaaa | 600 | |
| gacttctaca gagtgaaccc gaaaatcctt ccttgcagga accagtctc agtgtccaac | 660 | |
| tctctaacct tggaactgtg agaactctga ggacaaagca gcggatacaa cctcaaaaga | 720 | |
| cgtctgtcta cattgaattg ggatctgatt cttctgaaga taccgttaat aaggcaactt | 780 | |
| attgcagtgt gggagatcaa gaattgttac aaatcacccc tcaaggaacc agggatgaaa | 840 | |
| tcagtttgga ttctgcaaaa aaggctgctt gtgaattttc tgagacggat gtaacaaata | 900 | |
| ctgaacatca tcaacccagt aataatgatt tgaacaccac tgagaagcgt gcagctgaga | 960 | |

```
ggcatccaga aaagtatcag ggtagttctg tttcaaactt gcatgtggag ccatgtggca    1020
caaatactca tgccagctca ttacagcatg agaacagcag tttattactc actaaagaca    1080
gaatgaatgt agaaaaggct gaattctgta ataaaagcaa acagcctggc ttagcaagga    1140
gccaacataa cagatgggct ggaagtaagg aaacatgtaa tgataggcgg actcccagca    1200
cagaaaaaaa ggtagatctg aatgctgatc ccctgtgtga gagaaaagaa tggaataagc    1260
agaaactgcc atgctcagag aatcctagag atactgaaga tgttccttgg ataacactaa    1320
atagcagcat tcagaaagtt aatgagtggt tttccagaag tgatgaactg ttaggttctg    1380
atgactcaca tgatggggag tctgaatcaa atgccaaagt agctgatgta ttggacgttc    1440
taaatgaggt agatgaatat tctggttctt cagagaaaat agacttactg ccagtgatc     1500 ctcatgaggc tttaatatgt aaaagtgaaa gagttcactc caaatcagta gagagtaata    1560
ttgaagacaa atatttggg aaaacctatc ggaagaaggc aagcctcccc aacttaagcc     1620
atgtaactga aaatctaatt ataggagcat ttgttactga gccacagata atacaagagc    1680
gtcccctcac aaataaatta aagcgtaaaa ggagacctac atcaggcctt catcctgagg    1740
attttatcaa gaaagcagat ttggcagttc aaaagactcc tgaaatgata aatcagggaa    1800
ctaaccaaac ggagcagaat ggtcaagtga tgaatattac taatagtggt catgagaata    1860
aaacaaaagg tgattctatt cagaatgaga aaaatcctaa cccaatagaa tcactcgaaa    1920
aagaatctgc tttcaaaacg aaagctgaac ctataagcag cagtataagc aatatggaac    1980
tcgaattaaa tatccacaat tcaaaagcac taaaaagaa taggctgagg aggaagtctt     2040
ctaccaggca tattcatgcg cttgaactag tagtcagtag aaatctaagc ccacctaatt    2100
gtactgaatt gcaaattgat agttgttcta gcagtgaaga gataagaaa aaaaagtaca     2160 accaaatgcc agtcaggcac agcagaaacc tacaactcat ggaaggtaaa gaacctgcaa    2220
ctggagccaa aagagtaac aagccaaatg aacagacaag taaaagacat gacagcgata     2280 cttttcccaga gctgaagtta acaaatgcac ctggttcttt tactaagtgt tcaaatacca    2340
gtgaacttaa agaatttgtc aatcctagcc ttccaagaga agaaaagaa gagaaactag     2400 aaacagttaa agtgtctaat aatgctgaag accccaaaga tctcatgtta agtggagaaa    2460
gggttttgca aactgaaaga tctgtagaga gtagcagtat ttcattggta cctggtactg    2520 attatgcac tcaggaaagt atctcgttac tggaagttag cactctaggg aaggcaaaaa     2580
cagaaccaaa taatgtgtg agtcagtgtg cagcatttga aaaccccaag ggactaattc     2640
atggttgttc caaagataat agaaatgaca cagaaggctt taagtatcca ttgggacatg    2700
aagttaacca cagtcgggaa acaagcatag aaatggaaga agtgaacttt gatgctcagt    2760
atttgcagaa tacattcaag gtttcaaagc gccagtcatt tgctccgttt tcaaatccag    2820
gaaatgcaga agaggaatgt gcaacattct ctgcccactc tgggtcctta agaaacaaa     2880 gtccaaaagt cacttttgaa tgtgaacaaa aggaagaaa tcaaggaaag aatgagtcta    2940
atatcaagcc tgtacagaca gttaatatca ctgcaggctt tcctgtggtt ggtcagaaag    3000
ataagccagt tgataatgcc aaatgtagta tcaaaggagg ctctaggttt tgtctatcat    3060
ctcagttcag aggcaacgaa actggactca ttactccaaa taaacatgga cttttacaaa    3120
acccatatcg tataccacca cttttttccca tcaagtcatt tgttaaaact aaatgtaaga     3180
aaaatctgct agaggaaaac tttgaggaac attcaatgtc acctgaaaga gaaatgggaa    3240
atgagaacat tccaagtaca gtgagcacaa ttagccgtaa taacattaga gaaaatgttt    3300
ttaaagaagc cagctcaagc aatattaatg aagtaggttc cagtactaat gaagtgggct    3360
```

```
ccagtattaa tgaaataggt tccagtgatg aaaacattca agcagaacta ggtagaaaca   3420
gagggccaaa attgaatgct atgcttagat tagggttttt gcaacctgag gtctataaac   3480
aaagtcttcc tggaagtaat tgtaagcatc ctgaaataaa aaagcaagaa tatgaagaag   3540
tagttcagac tgttaataca gatttctctc catatctgat ttcagataac ttagaacagc   3600
ctatgggaag tagtcatgca tctcaggttt gttctgagac acctgatgac ctgttagatg   3660
atggtgaaat aaaggaagat actagtttg ctgaaaatga cattaaggaa agttctgctg   3720
tttttagcaa aagcgtccag aaaggagagc ttagcaggag tcctagccct ttcacccata   3780
cacatttggc tcagggttac cgaagagggg ccaagaaatt agagtcctca gaagagaact   3840
tatctagtga ggatgaagag cttccctgct tccaacactt gttatttggt aaagtaaaca   3900
atataccttc tcagtctact aggcatagca ccgttgctac cgagtgtctg tctaagaaca   3960
cagaggagaa tttattatca ttgaagaata gcttaaatga ctgcagtaac caggtaatat   4020
tggcaaaggc atctcaggaa catcacctta gtgaggaaac aaaatgttct gctagcttgt   4080
tttcttcaca gtgcagtgaa ttggaagact tgactgcaaa tacaaacacc caggatcctt   4140
tcttgattgg ttcttccaaa caaatgaggc atcagtctga aagccaggga gttggtctga   4200
gtgacaagga attggtttca gatgatgaag aaagaggaac gggcttggaa gaaaataatc   4260
aagaagagca aagcatggat tcaaacttag gtgaagcagc atctgggtgt gagagtgaaa   4320
caagcgtctc tgaagactgc tcagggctat cctctcagag tgacatttta accactcagc   4380
agagggatac catgcaacat aacctgataa agctccagca ggaaatggct gaactagaag   4440
ctgtgttaga acagcatggg agccagcctt ctaacagcta cccttccatc ataagtgact   4500
cttctgccct tgaggacctg cgaaatccag aacaaagcac atcagaaaaa gcagtattaa   4560
cttcacagaa aagtagtgaa taccctataa gccagaatcc agaaggcctt tctgctgaca   4620
agtttgaggt gtctgcagat agttctacca gtaaaaataa agaaccagga gtggaaaggt   4680
catccccttc taaatgccca tcattagatg ataggtggta catgcacagt tgctctggga   4740
gtcttcagaa tagaaactac ccatctcaag aggagctcat taaggttgtt gatgtggagg   4800
agcaacagct ggaagagtct gggccacacg atttgacgga aacatcttac ttgccaaggc   4860
aagatctaga gggaaccccct tacctggaat ctggaatcag cctcttctct gatgaccctg   4920
aatctgatcc ttctgaagac agagcccag agtcagctcg tgttggcaac ataccatctt   4980
caacctctgc attgaaagtt ccccaattga agttgcaga atctgcccag agtccagctg   5040
ctgctcatac tactgatact gctgggtata atgcaatgga agaaagtgtg agcagggaga   5100
agccagaatt gacagcttca acagaaaggg tcaacaaaag aatgtccatg gtggtgtctg   5160
gcctgacccc agaagaattt atgctcgtgt acaagtttgc cagaaaacac cacatcactt   5220
taactaatct aattactgaa gagactactc atgttgttat gaaaacagat gctgagtttg   5280
tgtgtgaacg gacactgaaa tattttctag gaattgcggg aggaaaatgg gtagttagct   5340
atttctgggt gacccagtct attaaagaaa gaaaaatgct gaatgagcat gattttgaag   5400
tcagaggaga tgtggtcaat ggaagaaacc accaaggtcc aaagcgagca agagaatccc   5460
aggacagaaa gatcttcagg gggctagaaa tctgttgcta tgggcccttc accaacatgc   5520
ccacagatca actggaatgg atggtacagc tgtgtggtgc ttctgtggtg aaggagcttt   5580
catcattcac ccttggcaca ggtgtccacc caattgtggt tgtgcagcca gatgcctgga   5640
cagaggacaa tggcttccat gcaattgggc agatgtgtga ggcacctgtg gtgacccgag   5700
agtgggtgtt ggacagtgta gcactctacc agtgccagga gctggacacc tacctgatac   5760
```

| | | |
|---|---|---|
| cccagatccc ccacagccac tactgactgc agccagccac aggtacagag ccacaggacc | 5820 | |
| ccaagaatga gcttacaaag tggcctttcc aggccctggg agctcctctc actcttcagt | 5880 | |
| ccttctactg tcctggctac taaatatttt atgtacatca gcctgaaaag gacttctggc | 5940 | |
| tatgcaaggg tcccttaaag attttctgct tgaagtctcc cttggaaatc tgccatgagc | 6000 | |
| acaaaattat ggtaattttt cacctgagaa gattttaaaa ccatttaaac gccaccaatt | 6060 | |
| gagcaagatg ctgattcatt atttatcagc cctattcttt ctattcaggc tgttgttggc | 6120 | |
| ttagggctgg aagcacagag tggcttggcc tcaagagaat agctggtttc cctaagttta | 6180 | |
| cttctctaaa accctgtgtt cacaaaggca gagagtcaga cccttcaatg gaaggagagt | 6240 | |
| gcttgggatc gattatgtga cttaaagtca gaatagtcct tgggcagttc tcaaatgttg | 6300 | |
| gagtggaaca ttggggagga aattctgagg caggtattag aaatgaaaag gaaacttgaa | 6360 | |
| acctgggcat ggtggctcac gcctgtaatc ccagcacttt gggaggccaa ggtgggcaga | 6420 | |
| tcactgagg tcaggagttc gaaaccagcc tggccaacat ggtgaaaccc catctctact | 6480 | |
| aaaaatacag aaattagccg gtcatggtgg tggacacctg taatcccagc tactcaggtg | 6540 | |
| gctaaggcag gagaatcact tcagcccggg aggtggaggt tgcagtgagc caagatcata | 6600 | |
| ccacggcact ccagcctggg tgacagtgag actgtggctc aaaaaaaaaa aaaaaaaaag | 6660 | |
| gaaaatgaaa ctagaagaga tttctaaaag tctgagatat atttgctaga tttctaaaga | 6720 | |
| atgtgttcta aaacagcaga gattttcaa gaaccggttt ccaaagacag tcttctaatt | 6780 | |
| cctcattagt aataagtaaa atgtttattg ttgtagctct ggtatataat ccattcctct | 6840 | |
| taaaatataa gacctctggc atgaatattt catatctata aaatgacaga tcccaccagg | 6900 | |
| aaggaagctg ttgctttctt tgaggtgatt ttttccttt gctccctgtt gctgaaacca | 6960 | |
| tacagcttca taaataattt tgcttgctga aggaagaaaa agtgtttttc ataaacccat | 7020 | |
| tatccaggac tgtttatagc tgttggaagg actaggtctt ccctagcccc cccagtgtgc | 7080 | |
| aagggcagtg aagacttgat tgtacaaaat acgttttgta aatgttgtgc tgttaacact | 7140 | |
| gcaaataaac ttggtagcaa acacttcaaa aaaaaaaaaa aaaaa | 7185 | |

<210> SEQ ID NO 4
<211> LENGTH: 6502
<212> TYPE: DNA
<213> ORGANISM: Homo sapien

<400> SEQUENCE: 4

| | | |
|---|---|---|
| cttagcggta gccccttggt ttccgtggca acggaaaagc gcgggaatta cagataaatt | 60 | |
| aaaactgcga ctgcgcggcg tgagctcgct gagacttcct ggacggggga caggctgtgg | 120 | |
| ggtttctcag ataactgggc ccctgcgctc aggaggcctt caccctctgc tctgggtaaa | 180 | |
| gctgcttgtg aattttctga cggatgta acaaatactg aacatcatca acccagtaat | 240 | |
| aatgatttga acaccactga gaagcgtgca gctgagaggc atccagaaaa gtatcagggt | 300 | |
| agttctgttt caaacttgca tgtggagcca tgtggcacaa atactcatgc cagctcatta | 360 | |
| cagcatgaga acagcagttt attactcact aaagacagaa tgaatgtaga aaaggctgaa | 420 | |
| ttctgtaata aaagcaaaca gcctggctta gcaaggagcc aacataacag atgggctgga | 480 | |
| agtaaggaaa catgtaatga taggcggact cccagcacag aaaaaaaggt agatctgaat | 540 | |
| gctgatcccc tgtgtgagag aaaagaatgg aataagcaga aactgccatg ctcagagaat | 600 | |
| cctagagata ctgaagatgt tccttggata acactaaata gcagcattca gaaagttaat | 660 | |
| gagtggtttt ccagaagtga tgaactgtta ggttctgatg actcacatga tgggagtct | 720 | |

```
gaatcaaatg ccaaagtagc tgatgtattg gacgttctaa atgaggtaga tgaatattct    780
ggttcttcag agaaaataga cttactggcc agtgatcctc atgaggcttt aatatgtaaa    840
agtgaaagag ttcactccaa atcagtagag agtaatattg aagacaaaat atttgggaaa    900
acctatcgga agaaggcaag cctccccaac ttaagccatg taactgaaaa tctaattata    960
ggagcatttg ttactgagcc acagataata caagagcgtc ccctcacaaa taaattaaag   1020
cgtaaaagga gacctacatc aggccttcat cctgaggatt ttatcaagaa agcagatttg   1080
gcagttcaaa agactcctga atgataaat cagggaacta accaaacgga gcagaatggt   1140
caagtgatga atattactaa tagtggtcat gagaataaaa caaaggtga ttctattcag    1200 aatgagaaaa atcctaaccc aatagaatca ctcgaaaaag aatctgcttt caaaacgaaa   1260
gctgaaccta taagcagcag tataagcaat atggaactcg aattaaatat ccacaattca   1320
aaagcaccta aaaagaatag gctgaggagg aagtcttcta ccaggcatat tcatgcgctt   1380
gaactagtag tcagtagaaa tctaagccca cctaattgta ctgaattgca aattgatagt   1440
tgttctagca gtgaagagat aaagaaaaaa aagtacaacc aaatgccagt caggcacagc   1500
agaaacctac aactcatgga aggtaaagaa cctgcaactg gagccaagaa gagtaacaag   1560
ccaaatgaac agacaagtaa aagacatgac agcgatactt tcccagagct gaagttaaca   1620
aatgcacctg gttcttttac taagtgttca aataccagtg aacttaaaga atttgtcaat   1680
cctagccttc aagagaaga aaaagaagag aaactagaaa cagttaaagt gtctaataat   1740
gctgaagacc ccaaagatct catgttaagt ggagaaaggg ttttgcaaac tgaaagatct   1800
gtagagagta gcagtatttc attggtacct ggtactgatt atggcactca ggaaagtatc   1860
tcgttactgg aagttagcac tctagggaag gcaaaaacag aaccaaataa atgtgtgagt   1920
cagtgtgcag catttgaaaa ccccaaggga ctaattcatg gttgttccaa agataataga   1980
aatgacacag aaggctttaa gtatccattg ggacatgaag ttaaccacag tcgggaaaca   2040
agcatagaaa tggaagaaag tgaacttgat gctcagtatt gcagaatac attcaaggtt    2100 tcaaagcgcc agtcatttgc tccgttttca aatccaggaa atgcagaaga ggaatgtgca   2160
acattctctg cccactctgg gtccttaaag aaacaaagtc caaagtcac ttttgaatgt    2220 gaacaaaagg aagaaaatca aggaaagaat gagtctaata tcaagcctgt acagacagtt   2280
aatatcactg caggctttcc tgtggttggt cagaaagata agccagttga taatgccaaa   2340
tgtagtatca aggaggctc taggttttgt ctatcatctc agttcagagg caacgaaact    2400
ggactcatta ctccaaataa acatggactt ttacaaaacc catatcgtat accaccactt   2460
tttcccatca agtcatttgt taaaactaaa tgtaagaaaa atctgctaga ggaaacttt    2520 gaggaacatt caatgtcacc tgaaagagaa atgggaaatg agaacattcc aagtacagtg   2580
agcacaatta gccgtaataa cattagagaa atgttttta aagaagccag ctcaagcaat   2640
attaatgaag taggttccag tactaatgaa gtgggctcca gtattaatga atagggttcc    2700
agtgatgaaa acattcaagc agaactaggt agaaacagag ggccaaaatt gaatgctatg   2760
cttagattag gggttttgca acctgaggtc tataaacaaa gtcttcctgg aagtaattgt   2820
aagcatcctg aaataaaaaa gcaagaatat gaagaagtag ttcagactgt taatacagat   2880
ttctctccat atctgattc agataactta gaacagccta tgggaagtag tcatgcatct   2940
caggtttgtt ctgagacacc tgatgacctg ttagatgatg gtgaaataaa ggaagatact   3000
agttttgctg aaaatgacat taaggaaagt tctgctgttt ttagcaaaag cgtccagaaa   3060
ggagagctta gcaggagtcc tagcccttc acccatacac atttggctca gggttaccga   3120
```

-continued

```
agaggggcca agaaattaga gtcctcagaa gagaacttat ctagtgagga tgaagagctt    3180
ccctgcttcc aacacttgtt atttggtaaa gtaaacaata taccttctca gtctactagg    3240
catagcaccg ttgctaccga gtgtctgtct aagaacacag aggagaattt attatcattg    3300
aagaatagct taaatgactg cagtaaccag gtaatattgg caaaggcatc tcaggaacat    3360
caccttagtg aggaaacaaa atgttctgct agcttgtttt cttcacagtg cagtgaattg    3420
gaagacttga ctgcaaatac aaacacccag gatcctttct tgattggttc ttccaaacaa    3480
atgaggcatc agtctgaaag ccagggagtt ggtctgagtg acaaggaatt ggtttcagat    3540
gatgaagaaa gaggaacggg cttggaagaa aataatcaag aagagcaaag catggattca    3600
aacttaggtg aagcagcatc tgggtgtgag agtgaaacaa gcgtctctga agactgctca    3660
gggctatcct ctcagagtga cattttaacc actcagcaga gggataccat gcaacataac    3720
ctgataaagc tccagcagga aatggctgaa ctagaagctg tgttagaaca gcatgggagc    3780
cagccttcta acagctaccc ttccatcata agtgactctt ctgcccttga ggacctgcga    3840
aatccagaac aaagcacatc agaaaaagca gtattaactt cacagaaaag tagtgaatac    3900
cctataagcc agaatccaga aggcctttct gctgacaagt ttgaggtgtc tgcagatagt    3960
tctaccagta aaaataaaga accaggagtg gaaaggtcat cccccttctaa atgcccatca    4020
ttagatgata ggtggtacat gcacagttgc tctgggagtc ttcagaatag aaactaccca    4080
tctcaagagg agctcattaa ggttgttgat gtggaggagc aacagctgga agagtctggg    4140
ccacacgatt tgacggaaac atcttacttg ccaaggcaag atctagaggg aaccccttac    4200
ctggaatctg gaatcagcct cttctctgat gaccctgaat ctgatccttc tgaagacaga    4260
gccccagagt cagctcgtgt tggcaacata ccatcttcaa cctctgcatt gaaagttccc    4320
caattgaaag ttgcagaatc tgcccagagt ccagctgctg ctcatactac tgatactgct    4380
gggtataatg caatggaaga agtgtgagc agggagaagc cagaattgac agcttcaaca    4440
gaaagggtca acaaaagaat gtccatggtg gtgtctggcc tgaccccaga agaatttatg    4500
ctcgtgtaca gtttgccag aaaacaccac atcactttaa ctaatctaat tactgaagag    4560
actactcatg ttgttatgaa aacagatgct gagtttgtgt gtgaacggac actgaaatat    4620
tttctaggaa ttgcgggagg aaaatgggta gttagctatt tctgggtgac ccagtctatt    4680
aaagaaagaa aaatgctgaa tgagcatgat tttgaagtca gaggagatgt ggtcaatgga    4740
agaaaccacc aaggtccaaa gcgagcaaga gaatcccagg acagaaagat cttcaggggg    4800
ctagaaatct gttgctatgg gcccttcacc aacatgccca cagatcaact ggaatggatg    4860
gtacagctgt gtggtgcttc tgtggtgaag gagctttcat cattcaccct tggcacaggt    4920
gtccacccaa ttgtggttgt gcagccagat gcctggacag aggacaatgg cttccatgca    4980
attgggcaga tgtgtgaggc acctgtggtg acccgagagt gggtgttgga cagtgtagca    5040
ctctaccagt gccaggagct ggacacctac ctgatacccc agatccccca cagccactac    5100
tgactgcagc cagccacagg tacagagcca caggacccca agaatgagct tacaaagtgg    5160
cctttccagg ccctgggagc tcctctcact cttcagtcct tctactgtcc tggctactaa    5220
atatttatg tacatcagcc tgaaaaggac ttctggctat gcaagggtcc cttaaagatt    5280
ttctgcttga agtctccctt ggaaatctgc catgagcaca aaattatggt aattttttcac    5340
ctgagaagat tttaaaacca tttaaacgcc accaattgag caagatgctg attcattatt    5400
tatcagccct attctttcta ttcaggctgt tgttggctta gggctggaag cacagagtgg    5460
cttggcctca agagaatagc tggtttccct aagtttactt ctctaaaacc ctgtgttcac    5520
```

```
aaaggcagag agtcagaccc ttcaatggaa ggagagtgct tgggatcgat tatgtgactt      5580
aaagtcagaa tagtccttgg gcagttctca aatgttggag tggaacattg gggaggaaat      5640
tctgaggcag gtattagaaa tgaaaggaa acttgaaacc tgggcatggt ggctcacgcc      5700
tgtaatccca gcactttggg aggccaaggt gggcagatca ctggaggtca ggagttcgaa      5760
accagcctgg ccaacatggt gaaaccccat ctctactaaa aatacagaaa ttagccggtc      5820
atggtggtgg acacctgtaa tcccagctac tcaggtggct aaggcaggag aatcacttca      5880
gcccgggagg tggaggttgc agtgagccaa gatcatacca cggcactcca gcctgggtga      5940
cagtgagact gtggctcaaa aaaaaaaaa aaaaaggaa aatgaaacta gaagagattt         6000
ctaaaagtct gagatatatt tgctagattt ctaaagaatg tgttctaaaa cagcagaaga      6060
ttttcaagaa ccggttttcca aagacagtct tctaattcct cattagtaat aagtaaaatg     6120
tttattgttg tagctctggt ataatccca ttcctcttaa aatataagac ctctggcatg       6180
aatatttcat atctataaaa tgacagatcc caccaggaag gaagctgttg ctttctttga      6240
ggtgattttt ttcctttgct ccctgttgct gaaaccatac agcttcataa ataattttgc      6300
ttgctgaagg aagaaaaagt gttttcata aacccattat ccaggactgt ttatagctgt       6360
tggaaggact aggtcttccc tagccccccc agtgtgcaag ggcagtgaag acttgattgt      6420
acaaaatacg ttttgtaaat gttgtgctgt taacactgca aataaacttg gtagcaaaca      6480
cttcaaaaaa aaaaaaaaa aa                                                 6502

<210> SEQ ID NO 5
<211> LENGTH: 3642
<212> TYPE: DNA
<213> ORGANISM: Homo sapien

<400> SEQUENCE: 5
cttagcggta gccccttggt ttccgtggca acggaaaagc gcgggaatta cagataaatt        60
aaaactgcga ctgcgcggcg tgagctcgct gagacttcct ggacggggga caggctgtgg      120
ggtttctcag ataactgggc ccctgcgctc aggaggcctt caccctctgc tctgggtaaa       180
gttcattgga acagaaagaa atggatttat ctgctcttcg cgttgaagaa gtacaaaatg       240
tcattaatgc tatgcagaaa atcttagagt gtcccatctg tctggagttg atcaaggaac       300
ctgtctccac aaagtgtgac cacatatttt gcaaattttg catgctgaaa cttctcaacc       360
agaagaaagg gccttcacag tgtccttat gtaagaatga tataaccaaa aggagcctac        420
aagaaagtac gagatttagt caacttgttg aagagctatt gaaaatcatt tgtgcttttc       480
agcttgacac aggtttggag tatgcaaaca gctataattt tgcaaaaag gaaaataact        540 ctcctgaaca tctaaaagat gaagtttcta tcatccaaag tatgggctac agaaaccgtg       600
ccaaaagact tctacagagt gaacccgaaa tccttccttt gcaggaaacc agtctcagtg       660
tccaactctc taaccttgga actgtgagaa ctctgaggac aaagcagcgg atacaacctc       720
aaaagacgtc tgtctacatt gaattgggtg aagcagcatc tgggtgtgag agtgaaacaa      780
gcgtctctga agactgctca gggctatcct ctcagagtga cattttaacc actcagcaga      840
gggataccat gcaacataac ctgataaagc tccagcagga aatggctgaa ctagaagctg      900
tgttagaaca gcatgggagc cagccttcta acagctaccc ttccatcata agtgactctt      960
ctgcccttga ggacctgcga aatccagaac aaagcacatc agaaaaagca gtattaactt    1020
cacagaaaag tagtgaatac cctataagcc agaatccaga aggcctttct gctgacaagt    1080
ttgaggtgtc tgcagatagt tctaccagta aaaataaaga accaggagtg gaaaggtcat    1140
```

```
cccctcctaa atgcccatca ttagatgata ggtggtacat gcacagttgc tctgggagtc    1200
ttcagaatag aaaactaccca tctcaagagg agctcattaa ggttgttgat gtggaggagc    1260
aacagctgga agagtctggg ccacacgatt tgacggaaac atcttacttg ccaaggcaag    1320
atctagaggg aaccccttac ctggaatctg gaatcagcct cttctctgat gaccctgaat    1380
ctgatccttc tgaagacaga gccccagagt cagctcgtgt tggcaacata ccatcttcaa    1440
cctctgcatt gaaagttccc caattgaaag ttgcagaatc tgcccagagt ccagctgctg    1500
ctcatactac tgatactgct gggtataatg caatggaaga agtgtgagc agggagaagc    1560 cagaattgac agcttcaaca gaaagggtca acaaaagaat gtccatggtg gtgtctggcc    1620 tgacccccaga agaatttatg ctcgtgtaca agtttgccag aaaacaccac atcactttaa    1680
ctaatctaat tactgaagag actactcatg ttgttatgaa aacagatgct gagtttgtgt    1740
gtgaacggac actgaaatat tttctaggaa ttgcgggagg aaaatgggta gttagctatt    1800
tctgggtgac ccagtctatt aaagaaagaa aaatgctgaa tgagcatgat tttgaagtca    1860
gaggagatgt ggtcaatgga agaaaccacc aaggtccaaa gcgagcaaga gaatcccagg    1920
acagaaagat cttcaggggg ctagaaatct gttgctatgg gcccttcacc aacatgccca    1980
cagatcaact ggaatggatg gtacagctgt gtggtgcttc tgtggtgaag gagcttttcat   2040 cattcaccct tggcacaggt gtccacccaa ttgtggttgt gcagccagat gcctggacag    2100
aggacaatgg cttccatgca attgggcaga tgtgtgaggc acctgtggtg acccgagagt    2160
gggtgttgga cagtgtagca ctctaccagt gccaggagct ggacacctac ctgatacccc    2220 agatcccccca cagccactac tgactgcagc cagccacagg tacagagcca caggaccccca   2280 agaatgagct tacaaagtgg cctttccagg ccctgggagc tcctctcact cttcagtcct    2340
tctactgtcc tggctactaa atattttatg tacatcagcc tgaaaaggac ttctggctat    2400
gcaagggtcc cttaaagatt ttctgcttga agtctccctt ggaaatctgc catgagcaca    2460
aaattatggt aattttcac ctgagaagat tttaaaacca tttaaacgcc accaattgag    2520
caagatgctg attcattatt tatcagcct attctttcta ttcaggctgt tgttggctta    2580
gggctggaag cacagagtgg cttggcctca agagaatagc tggttcccct aagtttactt    2640
ctctaaaacc ctgtgttcac aaaggcagag agtcagaccc ttcaatggaa ggagagtgct    2700
tgggatcgat tatgtgactt aaagtcagaa tagtccttgg gcagttctca atgttggag    2760 tggaacattg gggaggaaat tctgaggcag gtattagaaa tgaaaaggaa acttgaaacc    2820
tgggcatggt ggctcacgcc tgtaatccca gcactttggg aggccaaggt gggcagatca    2880
ctggaggtca ggagttcgaa accagcctgg ccaacatggt gaaaccccat ctctactaaa    2940
aatacagaaa ttagccggtc atggtggtgg acacctgtaa tcccagctac tcaggtggct    3000
aaggcaggag aatcacttca gcccgggagg tggaggttgc agtgagccaa gatcatacca    3060
cggcactcca gcctgggtga cagtgagact gtggctcaaa aaaaaaaaaa aaaaaggaa    3120 aatgaaacta aagagattt ctaaaagtct gagatatatt tgctagattt ctaaagaatg    3180
tgttctaaaa cagcagaaga ttttcaagaa ccggttccca aagacagtct tctaattcct    3240
cattagtaat aagtaaaatg tttattgttg tagctctggt atataatcca ttcctcttaa    3300
aatataagac ctctggcatg aatattcat atctataaaa tgcagatcc caccaggaag    3360 gaagctgttg cttctcttga ggtgatttt ttcctttgct ccctgttgct gaaaccatac    3420
agcttcataa ataattttgc ttgctgaagg aagaaaaagt gtttttcata aacccattat    3480
ccaggactgt ttatagctgt tggaaggact aggtcttccc tagccccccc agtgtgcaag    3540
```

-continued

| | |
|---|---|
| ggcagtgaag acttgattgt acaaaatacg ttttgtaaat gttgtgctgt taacactgca | 3600 |
| aataaacttg gtagcaaaca cttcaaaaaa aaaaaaaaaa aa | 3642 |

<210> SEQ ID NO 6
<211> LENGTH: 6474
<212> TYPE: DNA
<213> ORGANISM: Homo sapien

<400> SEQUENCE: 6

| | |
|---|---|
| cttagcggta gccccttggt ttccgtggca acggaaaagc gcgggaatta cagataaatt | 60 |
| aaaactgcga ctgcgcggcg tgagctcgct gagacttcct ggacggggga caggctgtgg | 120 |
| ggtttctcag ataactgggc ccctgcgctc aggaggcctt caccctctgc tctgggtaaa | 180 |
| gttcattgga acagaaagaa atggatttat ctgctcttcg cgttgaagaa gtacaaaatg | 240 |
| tcattaatgc tatgcagaaa atcttagagt gtcccatctg tctggagttg atcaaggaac | 300 |
| ctgtctccac aaagtgtgac cacatatttt gcaaattttg catgctgaaa cttctcaacc | 360 |
| agaagaaagg gccttcacag tgtcctttat gtaagaatga tataaccaaa aggagcctac | 420 |
| aagaaagtac gagatttagt caacttgttg aagagctatt gaaaatcatt tgtgcttttc | 480 |
| agcttgacac aggtttggag tatgcaaaca gctataattt tgcaaaaaag gaaaataact | 540 |
| ctcctgaaca tctaaaagat gaagtttcta tcatccaaag tatgggctac agaaaccgtg | 600 |
| ccaaaagact tctacagagt gaacccgaaa atccttcctt gcaggaaacc agtctcagtg | 660 |
| tccaactctc taaccttgga actgtgagaa ctctgaggac aaagcagcgg atacaacctc | 720 |
| aaaagacgtc tgtctacatt gaattgggat ctgattcttc tgaagatacc gttaataagg | 780 |
| caacttattg cagtgtggga gatcaagaat tgttacaaat cacccctcaa ggaaccaggg | 840 |
| atgaaatcag tttggattct gcaaaaaagg ctgcttgtga attttctgag acggatgtaa | 900 |
| caaatactga acatcatcaa cccagtaata atgatttgaa caccactgag aagcgtgcag | 960 |
| ctgagaggca tccagaaaag tatcagggta gttctgtttc aaacttgcat gtggagccat | 1020 |
| gtggcacaaa tactcatgcc agctcattac agcatgagaa cagcagttta ttactcacta | 1080 |
| aagacagaat gaatgtagaa aaggctgaat tctgtaataa aagcaaacag cctggcttag | 1140 |
| caaggagcca acataacaga tgggctggaa gtaaggaaac atgtaatgat aggcggactc | 1200 |
| ccagcacaga aaaaaggta gatctgaatg ctgatcccct gtgtgagaga aaagaatgga | 1260 |
| ataagcagaa actgccatgc tcagagaatc ctagagatac tgaagatgtt ccttggataa | 1320 |
| cactaaatag cagcattcag aaagttaatg agtggttttc cagaagtgat gaactgttag | 1380 |
| gttctgatga ctcacatgat ggggagtctg aatcaaatgc caaagtagct gatgtattgg | 1440 |
| acgttctaaa tgaggtagat gaatattctg gttcttcaga gaaaatagac ttactggcca | 1500 |
| gtgatcctca tgaggcttta atatgtaaaa gtgaaagagt tcactccaaa tcagtagaga | 1560 |
| gtaatattga agacaaaata tttgggaaaa cctatcggaa gaaggcaagc ctccccaact | 1620 |
| taagccatgt aactgaaaat ctaattatag gagcatttgt tactgagcca cagataatac | 1680 |
| aagagcgtcc cctcacaaat aaattaaagc gtaaaaggag acctacatca ggccttcatc | 1740 |
| ctgaggattt tatcaagaaa gcagatttgg cagttcaaaa gactcctgaa atgataaatc | 1800 |
| agggaactaa ccaaacggag cagaatggtc aagtgatgaa tattactaat agtggtcatg | 1860 |
| agaataaaac aaaaggtgat tctattcaga atgagaaaaa tcctaaccca atagaatcac | 1920 |
| tcgaaaaaga atctgctttc aaaacgaaag ctgaacctat aagcagcagt ataagcaata | 1980 |
| tggaactcga attaaatatc cacaattcaa aagcacctaa aaagaatagg ctgaggagga | 2040 |

```
agtcttctac caggcatatt catgcgcttg aactagtagt cagtagaaat ctaagcccac   2100
ctaattgtac tgaattgcaa attgatagtt gttctagcag tgaagagata agaaaaaaaa   2160
agtacaacca aatgccagtc aggcacagca gaaacctaca actcatggaa ggtaaagaac   2220
ctgcaactgg agccaagaag agtaacaagc caaatgaaca gacaagtaaa agacatgaca   2280
gcgatacttt cccagagctg aagttaacaa atgcacctgg ttcttttact aagtgttcaa   2340
ataccagtga acttaaagaa tttgtcaatc ctagccttcc aagagaagaa aaagaagaga   2400
aactagaaac agttaaagtg tctaataatg ctgaagaccc caaagatctc atgttaagtg   2460
gagaaagggt tttgcaaact gaaagatctg tagagagtag cagtatttca ttggtacctg   2520
gtactgatta tggcactcag gaaagtatct cgttactgga agttagcact ctagggaagg   2580
caaaaacaga accaaataaa tgtgtgagtc agtgtgcagc atttgaaaac cccaagggac   2640
taattcatgg ttgttccaaa gataatagaa atgacacaga aggctttaag tatccattgg   2700
gacatgaagt taaccacagt cgggaaacaa gcatagaaat ggaagaaagt gaacttgatg   2760
ctcagtattt gcagaataca ttcaaggttt caaagcgcca gtcatttgct ccgttttcaa   2820
atccaggaaa tgcagaagag gaatgtgcaa cattctctgc ccactctggg tccttaaaga   2880
aacaaagtcc aaaagtcact tttgaatgtg aacaaaagga agaaaatcaa ggaaagaatg   2940
agtctaatat caagcctgta cagacagtta atatcactgc aggctttcct gtggttggtc   3000
agaaagataa gccagttgat aatgccaaat gtagtatcaa aggaggctct aggttttgtc   3060
tatcatctca gttcagaggc aacgaaactg gactcattac tccaaataaa catggacttt   3120
tacaaaaccc atatcgtata ccaccacttt ttcccatcaa gtcatttgtt aaaactaaat   3180
gtaagaaaaa tctgctagag gaaaactttg aggaacattc aatgtcacct gaaagagaaa   3240
tgggaaatga gaacattcca agtacagtga gcacaattag ccgtaataac attagagaaa   3300 atgttttaa agaagccagc tcaagcaata ttaatgaagt aggttccagt actaatgaag   3360
tgggctccag tattaatgaa ataggttcca gtgatgaaaa cattcaagca gaactaggta   3420
gaaacagagg gccaaaattg aatgctatgc ttagattagg ggttttgcaa cctgaggtct   3480
ataaacaaag tcttcctgga agtaattgta agcatcctga ataaaaaag caagaatatg   3540 aagaagtagt tcagactgtt aatacagatt tctctccata tctgatttca gataacttag   3600
aacagcctat gggaagtagt catgcatctc aggtttgttc tgagacacct gatgacctgt   3660
tagatgatgg tgaaataaag gaagatacta gttttgctga aaatgacatt aaggaaagtt   3720
ctgctgtttt tagcaaaagc gtccagaaag agagcttag caggagtcct agcccttca   3780 cccatacaca tttggctcag ggttaccgaa gaggggccaa gaaattagag tcctcagaag   3840
agaacttatc tagtgaggat gaagagcttc cctgcttcca acacttgtta tttggtaaag   3900
taaacaatat accttctcag tctactaggc atagcaccgt tgctaccgag tgtctgtcta   3960
agaacacaga ggagaattta ttatcattga agaaatagctt aaatgactgc agtaaccagg   4020
taatattggc aaaggcatct caggaacatc accttagtga ggaaacaaaa tgttctgcta   4080
gcttgttttc ttcacagtgc agtgaattgg aagacttgac tgcaaataca acacccagg   4140 atcctttctt gattggttct tccaaacaaa tgaggcatca gtctgaaagc caggggagttg   4200 gtctgagtga caaggaattg gtttcagatg atgaagaaag aggaacgggc ttggaagaaa   4260
ataatcaaga agagcaaagc atggattcaa acttaggtga agcagcatct gggtgtgaga   4320
gtgaaacaag cgtctctgaa gactgctcag ggctatcctc tcagagtgac attttaacca   4380
ctcagcagag ggataccatg caacataacc tgataaagct ccagcaggaa atggctgaac   4440
```

```
tagaagctgt gttagaacag catgggagcc agccttctaa cagctaccct tccatcataa    4500
gtgactcttc tgcccttgag gacctgcgaa atccagaaca aagcacatca gaaaaagatg    4560
ctgagtttgt gtgtgaacgg acactgaaat attttctagg aattgcggga ggaaaatggg    4620
tagttagcta tttctggggtg acccagtcta ttaaagaaag aaaaatgctg aatgagcatg    4680
attttgaagt cagaggagat gtggtcaatg gaagaaacca ccaaggtcca aagcgagcaa    4740
gagaatccca ggacagaaag atcttcaggg ggctagaaat ctgttgctat gggcccttca    4800
ccaacatgcc cacagatcaa ctggaatgga tggtacagct gtgtggtgct tctgtggtga    4860
aggagctttc atcattcacc cttggcacag gtgtccaccc aattgtggtt gtgcagccag    4920
atgcctggac agaggacaat ggcttccatg caattgggca gatgtgtgag gcacctgtgg    4980
tgacccgaga gtgggtgttg acagtgtag cactctacca gtgccaggag ctggacacct    5040
acctgatacc ccagatcccc cacagccact actgactgca gccagccaca ggtacagagc    5100
cacaggaccc caagaatgag cttacaaagt ggcctttcca ggccctggga gctcctctca    5160
ctcttcagtc cttctactgt cctggctact aaatatttta tgtacatcag cctgaaaagg    5220
acttctggct atgcaagggt cccttaaaga ttttctgctt gaagtctccc ttggaaatct    5280
gccatgagca caaaattatg gtaattttc acctgagaag attttaaaac catttaaacg    5340
ccaccaattg agcaagatgc tgattcatta tttatcagcc ctattctttc tattcaggct    5400
gttgttggct tagggctgga agcacagagt ggcttggcct caagagaata gctggtttcc    5460
ctaagtttac ttctctaaaa ccctgtgttc acaaaggcag agagtcagac ccttcaatgg    5520
aaggagagtg cttgggatcg attatgtgac ttaaagtcag aatagtcctt gggcagttct    5580
caaatgttgg agtggaacat tggggaggaa attctgaggc aggtattaga aatgaaaagg    5640
aaacttgaaa cctgggcatg gtggctcacg cctgtaatcc cagcactttg ggaggccaag    5700
gtgggcagat cactggaggt caggagttcg aaaccagcct ggccaacatg gtgaaacccc    5760
atctctacta aaaatacaga aattagccgg tcatggtggt ggacacctgt aatcccagct    5820
actcaggtgg ctaaggcagg agaatcactt cagcccggga ggtggaggtt gcagtgagcc    5880
aagatcatac cacggcactc cagcctgggt gacagtgaga ctgtggctca aaaaaaaaa    5940 aaaaaaagg aaaatgaaac tagaagagat ttctaaaagt ctgagatata tttgctagat    6000
ttctaaagaa tgtgttctaa aacagcagaa gattttcaag aaccggtttc caagacagt    6060 cttctaattc ctcattagta ataagtaaaa tgtttattgt tgtagctctg gtatataatc    6120
cattcctctt aaaatataag acctctgca tgaatatttc atatctataa aatgacagat    6180
cccaccagga aggaagctgt tgctttcttt gaggtgattt ttttcctttg ctccctgttg    6240
ctgaaaccat acagcttcat aaataatttt gcttgctgaa ggaagaaaaa gtgttttca    6300 taaacccatt atccaggact gtttatagct gttggaagga ctaggtcttc cctagcccccc    6360 ccagtgtgca agggcagtga agacttgatt gtacaaaata cgttttgtaa atgttgtgct    6420
gttaacactg caaataaact tggtagcaaa cacttcaaaa aaaaaaaaaa aaaa          6474
```

<210> SEQ ID NO 7
<211> LENGTH: 6396
<212> TYPE: DNA
<213> ORGANISM: Homo sapien

<400> SEQUENCE: 7

```
cttagcggta gccccttggt ttccgtggca acggaaaagc gcgggaatta cagataaatt      60
aaaactgcga ctgcgcggcg tgagctcgct gagacttcct ggacggggga caggctgtgg     120
```

```
ggtttctcag ataactgggc ccctgcgctc aggaggcctt caccctctgc tctgggtaaa      180
gttcattgga acagaaagaa atggatttat ctgctcttcg cgttgaagaa gtacaaaatg      240
tcattaatgc tatgcagaaa atcttagagt gtcccatctg tctggagttg atcaaggaac      300
ctgtctccac aaagtgtgac cacatatttt gcaaattttg catgctgaaa cttctcaacc      360
agaagaaagg gccttcacag tgtcctttat gtaagaatga tataaccaaa aggagcctac      420
aagaaagtac gagatttagt caacttgttg aagagctatt gaaaatcatt tgtgcttttc      480
agcttgacac aggtttggag tatgcaaaca gctataattt tgcaaaaaag gaaaataact      540
ctcctgaaca tctaaaagat gaagtttcta tcatccaaag tatgggctac agaaaccgtg      600
ccaaaagact tctacagagt gaacccgaaa atccttcctt gcaggaaacc agtctcagtg      660
tccaactctc taaccttgga actgtgagaa ctctgaggac aaagcagcgg atacaacctc      720
aaaagacgtc tgtctacatt gaattgggat ctgattcttc tgaagatacc gttaataagg      780
caacttattg cagtgtggga gatcaagaat tgttacaaat caccccctcaa ggaaccaggg      840 atgaaatcag tttggattct gcaaaaaagg ctgcttgtga attttctgag acggatgtaa      900
caaatactga acatcatcaa cccagtaata atgatttgaa caccactgag aagcgtgcag      960
ctgagaggca tccagaaaag tatcagggta gttctgtttc aaacttgcat gtggagccat     1020
gtggcacaaa tactcatgcc agctcattac agcatgagaa cagcagttta ttactcacta     1080
aagacagaat gaatgtagaa aaggctgaat tctgtaataa aagcaaacag cctggcttag     1140
caaggagcca acataacaga tgggctggaa gtaaggaaac atgtaatgat aggcggactc     1200
ccagcacaga aaaaaaggta gatctgaatg ctgatcccct gtgtgagaga aaagaatgga     1260
ataagcagaa actgccatgc tcagagaatc ctagagatac tgaagatgtt ccttggataa     1320
cactaaatag cagcattcag aaagttaatg agtggttttc cagaagtgat gaactgttag     1380
gttctgatga ctcacatgat ggggagtctg aatcaaatgc caaagtagct gatgtattgg     1440
acgttctaaa tgaggtagat gaatattctg gttcttcaga gaaaatagac ttactggcca     1500
gtgatcctca tgaggcttta atatgtaaaa gtgaaagagt tcactccaaa tcagtagaga     1560
gtaatattga agacaaaata tttgggaaaa cctatcggaa gaaggcaagc ctccccaact     1620
taagccatgt aactgaaaat ctaattatag gagcatttgt tactgagcca cagataatac     1680
aagagcgtcc cctcacaaat aaattaaagc gtaaaaggag acctacatca ggccttcatc     1740
ctgaggattt tatcaagaaa gcagatttgg cagttcaaaa gactcctgaa atgataaatc     1800
agggaactaa ccaaacggag cagaatggtc aagtgatgaa tattactaat agtggtcatg     1860
agaataaaac aaaaggtgat tctattcaga tgagaaaaa tcctaaccca atagaatcac     1920
tcgaaaaaga atctgctttc aaaacgaaag ctgaacctat aagcagcagt ataagcaata     1980
tggaactcga attaaatatc cacaattcaa aagcacctaa aaagaatagg ctgaggagga     2040
agtcttctac caggcatatt catgcgcttg aactagtagt cagtagaaat ctaagcccac     2100
ctaattgtac tgaattgcaa attgatagtt gttctagcag tgaagagata aagaaaaaaa     2160
agtacaacca aatgccagtc aggcacagca gaaacctaca actcatggaa ggtaaagaac     2220
ctgcaactgg agccaagaag agtaacaagc caaatgaaca gacaagtaaa agacatgaca     2280
gcgatacttt cccagagctg aagttaacaa atgcacctgg ttctttttact aagtgttcaa     2340 ataccagtga acttaaagaa tttgtcaatc ctagccttcc aagagaagaa aaagaagaga     2400
aactagaaac agtaaaagtg tctaataatg ctgaagaccc caaagatctc atgttaagtg     2460
gagaaagggt tttgcaaact gaaagatctg tagagagtag cagtatttca ttggtacctg     2520
```

```
gtactgatta tggcactcag gaaagtatct cgttactgga agttagcact ctagggaagg      2580
caaaaacaga accaaataaa tgtgtgagtc agtgtgcagc atttgaaaac cccaagggac      2640
taattcatgg ttgttccaaa gataatagaa atgacacaga aggctttaag tatccattgg      2700
gacatgaagt taaccacagt cgggaaacaa gcatagaaat ggaagaaagt gaacttgatg      2760
ctcagtattt gcagaataca ttcaaggttt caaagcgcca gtcatttgct ccgttttcaa      2820
atccaggaaa tgcagaagag gaatgtgcaa cattctctgc ccactctggg tccttaaaga      2880
aacaaagtcc aaaagtcact tttgaatgtg aacaaaagga agaaaatcaa ggaaagaatg      2940
agtctaatat caagcctgta cagacagtta atatcactgc aggctttcct gtggttggtc      3000
agaaagataa gccagttgat aatgccaaat gtagtatcaa aggaggctct aggttttgtc      3060
tatcatctca gttcagaggc aacgaaactg gactcattac tccaaataaa catggacttt      3120
tacaaaaccc atatcgtata ccaccacttt ttcccatcaa gtcatttgtt aaaactaaat      3180
gtaagaaaaa tctgctagag gaaaactttg aggaacattc aatgtcacct gaaagagaaa      3240
tgggaaatga gaacattcca agtacagtga gcacaattag ccgtaataac attagagaaa      3300 atgttttttaa agaagccagc tcaagcaata ttaatgaagt aggttccagt actaatgaag      3360
tgggctccag tattaatgaa ataggttcca gtgatgaaaa cattcaagca gaactaggta      3420
gaaacagagg gccaaaattg aatgctatgc ttagattagg ggttttgcaa cctgaggtct      3480
ataaacaaag tcttcctgga agtaattgta agcatcctga aataaaaag caagaatatg      3540 aagaagtagt tcagactgtt aatacagatt tctctccata tctgatttca gataacttag      3600
aacagcctat gggaagtagt catgcatctc aggtttgttc tgagacacct gatgacctgt      3660
tagatgatgg tgaaataaag gaagatacta gttttgctga aaatgacatt aaggaaagtt      3720
ctgctgtttt tagcaaaagc gtccagaaag gagagcttag caggagtcct agcccttca      3780 cccatacaca tttggctcag ggttaccgaa gaggggccaa gaattagag tcctcagaag      3840 agaacttatc tagtgaggat gaagagcttc cctgcttcca acacttgtta tttggtaaag      3900
taaacaatat accttctcag tctactaggc atagcaccgt tgctaccgag tgtctgtcta      3960
agaacacaga ggagaatta ttatcattga agaatagctt aaatgactgc agtaaccagg      4020
taatattggc aaaggcatct caggaacatc accttagtga ggaaacaaaa tgttctgcta      4080
gcttgttttc ttcacagtgc agtgaattgg aagacttgac tgcaaataca aacacccagg      4140 atccttctt gattggttct tccaaacaaa tgaggcatca gtctgaaagc cagggagttg      4200
gtctgagtga caaggaattg gtttcagatg atgaagaaag aggaacgggc ttggaagaaa      4260
ataatcaaga agagcaaagc atggattcaa acttaggtga agcagcatct gggtgtgaga      4320
gtgaaacaag cgtctctgaa gactgctcag ggctatcctc tcagagtgac attttaacca      4380
ctcagcagag ggataccatg caacataacc tgataaagct ccagcaggaa atggctgaac      4440
tagaagctgt gttagaacag catgggagcc agccttctaa cagctaccct tccatcataa      4500
gtgactcttc tgcccttgag gacctgcgaa atccagaaca aagcacatca gaaaaggggg      4560
tgacccagtc tattaaagaa agaaaaatgc tgaatgagca tgattttgaa gtcagaggag      4620
atgtggtcaa tggaagaaac caccaaggtc caaagcgagc aagagaatcc aggacagaa      4680 agatcttcag ggggctagaa atctgttgct atgggccctt caccaacatg cccacagatc      4740
aactggaatg gatggtacag ctgtgtggtg cttctgtggt gaaggagctt tcatcattca      4800
cccttggcac aggtgtccac ccaattgtgg ttgtgcagcc agatgcctgg acagaggaca      4860
atggcttcca tgcaattggg cagatgtgtg aggcacctgt ggtgacccga gagtgggtgt      4920
```

| | |
|---|---|
| tggacagtgt agcactctac cagtgccagg agctggacac ctacctgata ccccagatcc | 4980 |
| cccacagcca ctactgactg cagccagcca caggtacaga gccacaggac cccaagaatg | 5040 |
| agcttacaaa gtggcctttc caggccctgg gagctcctct cactcttcag tccttctact | 5100 |
| gtcctggcta ctaaatattt tatgtacatc agcctgaaaa ggacttctgg ctatgcaagg | 5160 |
| gtcccttaaa gattttctgc ttgaagtctc ccttggaaat ctgccatgag cacaaaatta | 5220 |
| tggtaatttt tcacctgaga agattttaaa accatttaaa cgccaccaat tgagcaagat | 5280 |
| gctgattcat tatttatcag ccctattctt tctattcagg ctgttgttgg cttagggctg | 5340 |
| gaagcacaga gtggcttggc ctcaagagaa tagctggttt ccctaagttt acttctctaa | 5400 |
| aaccctgtgt tcacaaaggc agagagtcag acccttcaat ggaaggagag tgcttgggat | 5460 |
| cgattatgtg acttaaagtc agaatagtcc ttgggcagtt ctcaaatgtt ggagtggaac | 5520 |
| attggggagg aaattctgag gcaggtatta gaaatgaaaa ggaaacttga aacctgggca | 5580 |
| tggtggctca cgcctgtaat cccagcactt gggaggcca aggtgggcag atcactggag | 5640 |
| gtcaggagtt cgaaccagc ctggccaaca tggtgaaacc ccatctctac taaaaataca | 5700 |
| gaaattagcc ggtcatggtg gtggacacct gtaatcccag ctactcaggt ggctaaggca | 5760 |
| ggagaatcac ttcagcccgg gaggtggagg ttgcagtgag ccaagatcat accacggcac | 5820 |
| tccagcctgg gtgacagtga gactgtggct caaaaaaaaa aaaaaaaaaa ggaaaatgaa | 5880 |
| actagaagag atttctaaaa gtctgagata tatttgctag atttctaaag aatgtgttct | 5940 |
| aaaacagcag aagattttca agaaccggtt tccaaagaca gtcttctaat tcctcattag | 6000 |
| taataagtaa aatgtttatt gttgtagctc tggtatataa tccattcctc ttaaaatata | 6060 |
| agacctctgg catgaatatt tcatatctat aaaatgacag atcccaccag gaaggaagct | 6120 |
| gttgctttct ttgaggtgat ttttttcctt tgctccctgt tgctgaaacc atacagcttc | 6180 |
| ataaataatt ttgcttgctg aaggaagaaa aagtgttttt cataaaccca ttatccagga | 6240 |
| ctgtttatag ctgttggaag gactaggtct tccctagccc ccccagtgtg caagggcagt | 6300 |
| gaagacttga ttgtacaaaa tacgttttgt aaatgttgtg ctgttaacac tgcaaataaa | 6360 |
| cttggtagca aacacttcaa aaaaaaaaaa aaaaaa | 6396 |

<210> SEQ ID NO 8
<211> LENGTH: 7068
<212> TYPE: DNA
<213> ORGANISM: Homo sapien

<400> SEQUENCE: 8

| | |
|---|---|
| cttagcggta gccccttggt ttccgtggca acggaaaagc gcgggaatta cagataaatt | 60 |
| aaaactgcga ctgcgcggcg tgagctcgct gagacttcct ggacggggga caggctgtgg | 120 |
| ggtttctcag ataactgggc ccctgcgctc aggaggcctt caccctctgc tctgggtaaa | 180 |
| gttcattgga acagaaagaa atggatttat ctgctcttcg cgttgaagaa gtacaaaatg | 240 |
| tcattaatgc tatgcagaaa atcttagagt gtcccatctg tctggagttg atcaaggaac | 300 |
| ctgtctccac aaagtgtgac cacatatttt gcaaattttg catgctgaaa cttctcaacc | 360 |
| agaagaaagg gccttcacag tgtccttat gtaagaatga tataaccaaa aggagcctac | 420 |
| aagaaagtac gagatttagt caacttgttg aagagctatt gaaaatcatt tgtgcttttc | 480 |
| agcttgacac aggtttggag tatgcaaaca gctataattt tgcaaaaaag gaaaataact | 540 |
| ctcctgaaca tctaaaagat gaagtttcta tcatccaaag tatgggctac agaaaccgtg | 600 |
| ccaaaagact tctacagagt gaacccgaaa atccttcctt gcaggaaacc agtctcagtg | 660 |

```
tccaactctc taaccttgga actgtgagaa ctctgaggac aaagcagcgg atacaacctc    720
aaaagacgtc tgtctacatt gaattggctg cttgtgaatt ttctgagacg gatgtaacaa    780
atactgaaca tcatcaaccc agtaataatg atttgaacac cactgagaag cgtgcagctg    840
agaggcatcc agaaaagtat cagggtagtt ctgtttcaaa cttgcatgtg gagccatgtg    900
gcacaaatac tcatgccagc tcattacagc atgagaacag cagtttatta ctcactaaag    960
acagaatgaa tgtagaaaag gctgaattct gtaataaaag caaacagcct ggcttagcaa   1020
ggagccaaca taacagatgg gctggaagta aggaaacatg taatgatagg cggactccca   1080
gcacagaaaa aaaggtagat ctgaatgctg atcccctgtg tgagagaaaa gaatggaata   1140
agcagaaact gccatgctca gagaatccta gagatactga agatgttcct tggataacac   1200
taaatagcag cattcagaaa gttaatgagt ggttttccag aagtgatgaa ctgttaggtt   1260
ctgatgactc acatgatggg gagtctgaat caaatgccaa agtagctgat gtattggacg   1320
ttctaaatga ggtagatgaa tattctggtt cttcagagaa aatagactta ctggccagtg   1380
atcctcatga ggctttaata tgtaaaagtg aaagagttca ctccaaatca gtagagagta   1440
atattgaaga caaatatttt gggaaaacct atcggaagaa ggcaagcctc cccaacttaa   1500
gccatgtaac tgaaaatcta attataggag catttgttac tgagccacag ataatacaag   1560
agcgtcccct cacaaataaa ttaaagcgta aaaggagacc tacatcaggc cttcatcctg   1620
aggattttat caagaaagca gatttggcag ttcaaaagac tcctgaaatg ataaatcagg   1680
gaactaacca aacggagcag aatggtcaag tgatgaatat tactaatagt ggtcatgaga   1740
ataaaacaaa aggtgattct attcagaatg agaaaaatcc taacccaata gaatcactcg   1800
aaaaagaatc tgcttttcaa acgaaagctg aacctataag cagcagtata agcaatatgg   1860
aactcgaatt aaatatccac aattcaaaag cacctaaaaa gaataggctg aggaggaagt   1920
cttctaccag gcatattcat gcgcttgaac tagtagtcag tagaaatcta agcccaccta   1980
attgtactga attgcaaatt gatagttgtt ctagcagtga agagataaag aaaaaaaagt   2040
acaaccaaat gccagtcagg cacagcgaaa acctacaact catggaaggt aaagaacctg   2100
caactggagc caagaagagt aacaagccaa atgaacagac aagtaaaaga catgacagcg   2160
atactttccc agagctgaag ttaacaaatg cacctggttc ttttactaag tgttcaaata   2220
ccagtgaact taaagaattt gtcaatccta gccttccaag agaagaaaaa gaagagaaac   2280
tagaaacagt taaagtgtct aataatgctg aagaccccaa agatctcatg ttaagtggag   2340
aaagggtttt gcaaactgaa agatctgtag agagtagcag tatttcattg gtacctggta   2400
ctgattatgg cactcaggaa agtatctcgt tactggaagt tagcactcta gggaaggcaa   2460
aaacagaacc aaataaatgt gtgagtcagt gtgcagcatt tgaaaacccc aagggactaa   2520
ttcatggttg ttccaaagat aatagaaatg acacagaagg ctttaagtat ccattgggac   2580
atgaagttaa ccacagtcgg gaaacaagca tagaaatgga agaaagtgaa cttgatgctc   2640
agtatttgca gaatacattc aaggtttcaa agcgccagtc atttgctccg ttttcaaatc   2700
caggaaatgc agaagaggaa tgtgcaacat tctctgccca ctctgggtcc ttaaagaaac   2760
aaagtccaaa agtcactttt gaatgtgaac aaaaggaaga aatcaagga aagaatgagt   2820 ctaatatcaa gcctgtacag acagttaata tcactgcagg cttttcctgtg gttggtcaga   2880 aagataagcc agttgataat gccaaatgta gtatcaaagg aggctctagg ttttgtctat   2940
catctcagtt cagaggcaac gaaactggac tcattactcc aaataaacat ggactttttac   3000 aaaacccata tcgtatacca ccacttttttc ccatcaagtc atttgttaaa actaaatgta   3060
```

```
agaaaaatct gctagaggaa aactttgagg aacattcaat gtcacctgaa agagaaatgg    3120
gaaatgagaa cattccaagt acagtgagca caattagccg taataacatt agagaaaatg    3180
tttttaaaga agccagctca agcaatatta atgaagtagg ttccagtact aatgaagtgg    3240
gctccagtat taatgaaata ggttccagtg atgaaaacat tcaagcagaa ctaggtagaa    3300
acagagggcc aaaattgaat gctatgctta gattaggggt tttgcaacct gaggtctata    3360
aacaaagtct tcctggaagt aattgtaagc atcctgaaat aaaaaagcaa gaatatgaag    3420
aagtagttca gactgttaat acagatttct ctccatatct gatttcagat aacttagaac    3480
agcctatggg aagtagtcat gcatctcagg tttgttctga cacctgat gacctgttag      3540 atgatggtga aataaaggaa gatactagtt ttgctgaaaa tgacattaag gaaagttctg    3600 ctgttttag caaaagcgtc cagaaaggag agcttagcag gagtcctagc cctttcaccc      3660
atacacattt ggctcagggt taccgaagag gggccaagaa attagagtcc tcagaagaga    3720
acttatctag tgaggatgaa gagcttccct gcttccaaca cttgttattt ggtaaagtaa    3780
acaatatacc ttctcagtct actaggcata gcaccgttgc taccgagtgt ctgtctaaga    3840
acacagagga gaatttatta tcattgaaga atagcttaaa tgactgcagt aaccaggtaa    3900
tattggcaaa ggcatctcag gaacatcacc ttagtgagga aacaaaatgt tctgctagct    3960
tgttttcttc acagtgcagt gaattggaag acttgactgc aaatacaaac acccaggatc    4020
ctttcttgat tggttcttcc aaacaaatga ggcatcagtc tgaaagccag ggagttggtc    4080
tgagtgacaa ggaattggtt tcagatgatg aagaagagg aacgggcttg gaagaaaata     4140
atcaagaaga gcaaagcatg gattcaaact taggtgaagc agcatctggg tgtgagagtg    4200
aaacaagcgt ctctgaagac tgctcagggc tatcctctca gagtgacatt ttaaccactc    4260
agcagaggga taccatgcaa cataacctga taaagctcca gcaggaaatg gctgaactag    4320
aagctgtgtt agaacagcat gggagccagc cttctaacag ctaccttcc atcataagtg      4380 actcttctgc ccttgaggac ctgcgaaatc cagaacaaag cacatcagaa aaagcagtat    4440
taacttcaca gaaagtagt gaataccta taagccagaa tccagaaggc ctttctgctg       4500
acaagtttga ggtgtctgca gatagttcta ccagtaaaaa taaagaacca ggagtggaaa    4560
ggtcatcccc ttctaaatgc ccatcattag atgataggtg gtacatgcac agttgctctg    4620
ggagtcttca gaatagaaac tacccatctc aagaggagct cattaaggtt gttgatgtgg    4680
aggagcaaca gctggaagag tctgggccac acgatttgac ggaaacatct tacttgccaa    4740
ggcaagatct agagggaacc ccttacctgg aatctggaat cagcctcttc tctgatgacc    4800
ctgaatctga tccttctgaa gacagagccc cagagtcagc tcgtgttggc aacataccat    4860
cttcaacctc tgcattgaaa gttccccaat tgaaagttgc agaatctgcc cagagtccag    4920
ctgctgctca tactactgat actgctgggt ataatgcaat ggaagaaagt gtgagcaggg    4980
agaagccaga attgacagct tcaacagaaa gggtcaacaa agaatgtcc atggtggtgt      5040 ctggcctgac cccagaagaa tttatgctcg tgtacaagtt tgccagaaaa caccacatca    5100
ctttaactaa tctaattact gaagagacta ctcatgttgt tatgaaaaca gatgctgagt    5160
ttgtgtgtga acggacactg aaatattttc taggaattgc gggaggaaaa tgggtagtta    5220
gctatttctg ggtgacccag tctattaaag aagaaaaat gctgaatgag catgattttg      5280
aagtcagagg agatgtggtc aatggaagaa accaccaagg tccaaagcga gcaagagaat    5340
cccaggacag aaagatcttc aggggggctag aaatctgttg ctatgggccc ttcaccaaca    5400
tgcccacaga tcaactggaa tggatggtac agctgtgtgg tgcttctgtg gtgaaggagc    5460
```

-continued

| | |
|---|---|
| tttcatcatt caccctggc acaggtgtcc acccaattgt ggttgtgcag ccagatgcct | 5520 |
| ggacagagga caatggcttc catgcaattg ggcagatgtg tgaggcacct gtggtgaccc | 5580 |
| gagagtgggt gttggacagt gtagcactct accagtgcca ggagctggac acctacctga | 5640 |
| taccccagat cccccacagc cactactgac tgcagccagc cacaggtaca gagccacagg | 5700 |
| accccaagaa tgagcttaca aagtggcctt tccaggccct gggagctcct ctcactcttc | 5760 |
| agtccttcta ctgtcctggc tactaaatat tttatgtaca tcagcctgaa aaggacttct | 5820 |
| ggctatgcaa gggtccctta aagattttct gcttgaagtc tcccttggaa atctgccatg | 5880 |
| agcacaaaat tatggtaatt tttcacctga aagattttta aaaccattta aacgccacca | 5940 |
| attgagcaag atgctgattc attatttatc agccctattc tttctattca ggctgttgtt | 6000 |
| ggcttagggc tggaagcaca gagtggcttg gcctcaagag aatagctggt ttccctaagt | 6060 |
| ttacttctct aaaaccctgt gttcacaaag gcagagagtc agacccttca atggaaggag | 6120 |
| agtgcttggg atcgattatg tgacttaaag tcagaatagt ccttgggcag ttctcaaatg | 6180 |
| ttggagtgga acattgggga ggaaattctg aggcaggtat tagaaatgaa aaggaaactt | 6240 |
| gaaacctggg catggtggct cacgcctgta atcccagcac tttgggaggc caaggtgggc | 6300 |
| agatcactgg aggtcaggag ttcgaaacca gcctggccaa catggtgaaa ccccatctct | 6360 |
| actaaaaata cagaaattag ccggtcatgg tggtggacac ctgtaatccc agctactcag | 6420 |
| gtggctaagg caggagaatc acttcagccc gggaggtgga ggttgcagtg agccaagatc | 6480 |
| ataccacggc actccagcct gggtgacagt gagactgtgg ctcaaaaaaa aaaaaaaaaa | 6540 |
| aaggaaaatg aaactagaag agatttctaa aagtctgaga tatatttgct agatttctaa | 6600 |
| agaatgtgtt ctaaaacagc agaagatttt caagaaccgg tttccaaaga cagtcttcta | 6660 |
| attcctcatt agtaataagt aaaatgttta ttgttgtagc tctggtatat aatccattcc | 6720 |
| tcttaaaata taagacctct ggcatgaata tttcatatct ataaaatgac agatcccacc | 6780 |
| aggaaggaag ctgttgcttt ctttgaggtg attttttttcc tttgctccct gttgctgaaa | 6840 |
| ccatacagct tcataaataa ttttgcttgc tgaaggaaga aaaagtgttt ttcataaacc | 6900 |
| cattatccag gactgtttat agctgttgga aggactaggt cttccctagc cccccagtg | 6960 |
| tgcaagggca gtgaagactt gattgtacaa aatacgtttt gtaaatgttg tgctgttaac | 7020 |
| actgcaaata aacttggtag caaacacttc aaaaaaaaaa aaaaaaaa | 7068 |

<210> SEQ ID NO 9
<211> LENGTH: 3765
<212> TYPE: DNA
<213> ORGANISM: Homo sapien

<400> SEQUENCE: 9

| | |
|---|---|
| cttagcggta gccccttggt ttccgtggca acggaaaagc gcgggaatta cagataaatt | 60 |
| aaaactgcga ctgcgcggcg tgagctcgct gagacttcct ggacggggga caggctgtgg | 120 |
| ggtttctcag ataactgggc ccctgcgctc aggaggcctt caccctctgc tctgggtaaa | 180 |
| gttcattgga acagaaagaa atggatttat ctgctcttcg cgttgaagaa gtacaaaatg | 240 |
| tcattaatgc tatgcagaaa atcttagagt gtcccatctg tctggagttg atcaaggaac | 300 |
| ctgtctccac aaagtgtgac cacatatttt gcaaattttg catgctgaaa cttctcaacc | 360 |
| agaagaaagg gccttcacag tgtccttat gtaagaatga tataaccaaa aggagcctac | 420 |
| aagaaagtac gagatttagt caacttgttg aagagctatt gaaaatcatt tgtgcttttc | 480 |
| agcttgacac aggtttggag tatgcaaaca gctataattt tgcaaaaaag gaaaataact | 540 |

```
ctcctgaaca tctaaaagat gaagtttcta tcatccaaag tatgggctac agaaaccgtg    600
ccaaaagact tctacagagt gaacccgaaa atccttcctt gcaggaaacc agtctcagtg    660
tccaactctc taaccttgga actgtgagaa ctctgaggac aaagcagcgg atacaacctc    720
aaaagacgtc tgtctacatt gaattgggat ctgattcttc tgaagatacc gttaataagg    780
caacttattg cagtgtggga gatcaagaat tgttacaaat cacccctcaa ggaaccaggg    840
atgaaatcag tttggattct gcaaaaaagg gtgaagcagc atctgggtgt gagagtgaaa    900
caagcgtctc tgaagactgc tcagggctat cctctcagag tgacatttta accactcagc    960
agagggatac catgcaacat aacctgataa agctccagca ggaaatggct gaactagaag   1020
ctgtgttaga acagcatggg agccagcctt ctaacagcta cccttccatc ataagtgact   1080
cttctgccct tgaggacctg cgaaatccag aacaaagcac atcagaaaaa gcagtattaa   1140
cttcacagaa aagtagtgaa taccctataa gccagaatcc agaaggcctt tctgctgaca   1200
agtttgaggt gtctgcagat agttctacca gtaaaaataa agaaccagga gtggaaaggt   1260
catcccttc taaatgccca tcattagatg ataggtggta catgcacagt tgctctggga   1320
gtcttcagaa tagaaactac ccatctcaag aggagctcat taaggttgtt gatgtggagg   1380
agcaacagct ggaagagtct gggccacacg atttgacgga acatcttac ttgccaaggc    1440
aagatctaga gggaaccct tacctggaat ctggaatcag cctcttctct gatgaccctg    1500
aatctgatcc ttctgaagac agagccccag agtcagctcg tgttggcaac ataccatctt   1560
caacctctgc attgaaagtt ccccaattga agttgcaga atctgcccag agtccagctg    1620
ctgctcatac tactgatact gctgggtata atgcaatgga agaaagtgtg agcagggaga   1680
agccagaatt gacagcttca acagaaaggg tcaacaaaag aatgtccatg gtggtgtctg   1740
gcctgacccc agaagaattt atgctcgtgt acaagtttgc cagaaaacac cacatcactt   1800
taactaatct aattactgaa gagactactc atgttgttat gaaaacagat gctgagtttg   1860
tgtgtgaacg gacactgaaa tatttctag gaattgcggg aggaaaatgg gtagttagct   1920
atttctgggt gacccagtct attaaagaaa gaaaaatgct gaatgagcat gattttgaag   1980
tcagaggaga tgtggtcaat ggaagaaacc accaaggtcc aaagcgagca agagaatccc   2040
aggacagaaa gatcttcagg gggctagaaa tctgttgcta tgggcccttc accaacatgc   2100
ccacagatca actggaatgg atggtacagc tgtgtggtgc ttctgtggtg aaggagcttt   2160
catcattcac ccttggcaca ggtgtccacc caattgtggt tgtgcagcca gatgcctgga   2220
cagaggacaa tggcttccat gcaattgggc agatgtgtga ggcacctgtg gtgacccgag   2280
agtgggtgtt ggacagtgta gcactctacc agtgccagga gctggacacc tacctgatac   2340
cccagatccc ccacagccac tactgactgc agccagccac aggtacagag ccacaggacc   2400
ccaagaatga gcttacaaag tggcctttcc aggccctggg agctcctctc actcttcagt   2460
ccttctactg tcctggctac taaatatttt atgtacatca gcctgaaaag acttctggc    2520
tatgcaaggg tcccttaaag attttctgct tgaagtctcc cttggaaatc tgccatgagc   2580
acaaaattat ggtaattttt cacctgagaa gattttaaaa ccatttaaac gccaccaatt   2640
gagcaagatg ctgattcatt atttatcagc cctattcttt ctattcaggc tgttgttggc   2700
ttagggctgg aagcacagag tggcttggcc tcaagagaat agctggtttc cctaagttta   2760
cttctctaaa accctgtgtt cacaaaggca gagagtcaga cccttcaatg gaaggagagt   2820
gcttgggatc gattatgtga cttaaagtca gaatagtcct tggcagttc tcaaatgttg    2880
gagtggaaca ttggggagga aattctgagg caggtattag aaatgaaaag gaaacttgaa   2940
```

-continued

| | |
|---|---|
| acctgggcat ggtggctcac gcctgtaatc ccagcacttt gggaggccaa ggtgggcaga | 3000 |
| tcactggagg tcaggagttc gaaaccagcc tggccaacat ggtgaaaccc catctctact | 3060 |
| aaaaatacag aaattagccg gtcatggtgg tggacacctg taatcccagc tactcaggtg | 3120 |
| gctaaggcag gagaatcact tcagcccggg aggtggaggt tgcagtgagc caagatcata | 3180 |
| ccacggcact ccagcctggg tgacagtgag actgtggctc aaaaaaaaaa aaaaaaaaag | 3240 |
| gaaaatgaaa ctagaagaga tttctaaaag tctgagatat atttgctaga tttctaaaga | 3300 |
| atgtgttcta aaacagcaga agattttcaa gaaccggttt ccaaagacag tcttctaatt | 3360 |
| cctcattagt aataagtaaa atgtttattg ttgtagctct ggtatataat ccattcctct | 3420 |
| taaaatataa gacctctggc atgaatattt catatctata aaatgacaga tcccaccagg | 3480 |
| aaggaagctg ttgctttctt tgaggtgatt ttttcctttt gctccctgtt gctgaaacca | 3540 |
| tacagcttca taaataattt tgcttgctga aggaagaaaa agtgtttttc ataaacccat | 3600 |
| tatccaggac tgtttatagc tgttggaagg actaggtctt ccctagcccc cccagtgtgc | 3660 |
| aagggcagtg aagacttgat tgtacaaaat acgttttgta aatgttgtgc tgttaacact | 3720 |
| gcaaataaac ttggtagcaa acacttcaaa aaaaaaaaaa aaaaa | 3765 |

<210> SEQ ID NO 10
<211> LENGTH: 3879
<212> TYPE: DNA
<213> ORGANISM: Homo sapien

<400> SEQUENCE: 10

| | |
|---|---|
| cttagcggta gccccttggt ttccgtggca acggaaaagc gcgggaatta cagataaatt | 60 |
| aaaactgcga ctgcgcggcg tgagctcgct gagacttcct ggacggggga caggctgtgg | 120 |
| ggtttctcag ataactgggc ccctgcgctc aggaggcctt cacccctctgc tctgggtaaa | 180 |
| gttcattgga acagaaagaa atggatttat ctgctcttcg cgttgaagaa gtacaaaatg | 240 |
| tcattaatgc tatgcagaaa atcttagagt gtcccatctg tctggagttg atcaaggaac | 300 |
| ctgtctccac aaagtgtgac cacatatttt gcaaattttg catgctgaaa cttctcaacc | 360 |
| agaagaaagg gccttcacag tgtccttat gtaagaatga tataaccaaa aggagcctac | 420 |
| aagaaagtac gagatttagt caacttgttg aagagctatt gaaaatcatt tgtgcttttc | 480 |
| agcttgacac aggtttggag tatgcaaaca gctataattt tgcaaaaaag gaaaataact | 540 |
| ctcctgaaca tctaaaagat gaagtttcta tcatccaaag tatgggctac agaaaccgtg | 600 |
| ccaaaagact tctacagagt gaacccgaaa atccttcctt gcaggaaacc agtctcagtg | 660 |
| tccaactctc taaccttgga actgtgagaa ctctgaggac aaagcagcgg atacaacctc | 720 |
| aaaagacgtc tgtctacatt gaattgggat ctgattcttc tgaagatacc gttaataagg | 780 |
| caacttattg cagtgtggga gatcaagaat tgttacaaat cacccctcaa ggaaccaggg | 840 |
| atgaaatcag tttggattct gcaaaaaagg ctgcttgtga attttctgag acggatgtaa | 900 |
| caaatactga acatcatcaa cccagtaata atgatttgaa caccactgag aagcgtgcag | 960 |
| ctgagaggca tccagaaaag tatcagggtg aagcagcatc tggtgtgag agtgaaacaa | 1020 |
| gcgtctctga agactgctca gggctatcct ctcagagtga cattttaacc actcagcaga | 1080 |
| gggataccat gcaacataac ctgataaagc tccagcagga aatggctgaa ctagaagctg | 1140 |
| tgttagaaca gcatgggagc cagccttcta acagctaccc ttccatcata agtgactctt | 1200 |
| ctgcccttga ggacctgcga aatccagaac aaagcacatc agaaaagta ttaacttcac | 1260 |
| agaaaagtag tgaataccct ataagccaga atccagaagg cctttctgct gacaagtttg | 1320 |

```
aggtgtctgc agatagttct accagtaaaa ataaagaacc aggagtggaa aggtcatccc    1380
cttctaaatg cccatcatta gatgataggt ggtacatgca cagttgctct gggagtcttc    1440
agaatagaaa ctacccatct caagaggagc tcattaaggt tgttgatgtg gaggagcaac    1500
agctggaaga gtctgggcca cacgatttga cggaaacatc ttacttgcca aggcaagatc    1560
tagagggaac cccttacctg gaatctggaa tcagcctctt ctctgatgac cctgaatctg    1620
atccttctga agacagagcc ccagagtcag ctcgtgttgg caacatacca tcttcaacct    1680
ctgcattgaa agttccccaa ttgaaagttg cagaatctgc ccagagtcca gctgctgctc    1740
atactactga tactgctggg tataatgcaa tggaagaaag tgtgagcagg gagaagccag    1800
aattgacagc ttcaacagaa agggtcaaca aaagaatgtc catggtggtg tctggcctga    1860
ccccagaaga atttatgctc gtgtacaagt ttgccagaaa acaccacatc actttaacta    1920
atctaattac tgaagagact actcatgttg ttatgaaaac agatgctgag tttgtgtgtg    1980
aacggacact gaaatatttt ctaggaattg cgggaggaaa atgggtagtt agctatttct    2040
gggtgaccca gtctattaaa gaaagaaaaa tgctgaatga gcatgatttt gaagtcagag    2100
gagatgtggt caatggaaga aaccaccaag gtccaaagcg agcaagagaa tcccaggaca    2160
gaaagatctt caggggcta gaaatctgtt gctatgggcc cttcaccaac atgcccacag    2220
atcaactgga atggatggta cagctgtgtg gtgcttctgt ggtgaaggag ctttcatcat    2280
tcacccttgg cacaggtgtc cacccaattg tggttgtgca gccagatgcc tggacagagg    2340
acaatggctt ccatgcaatt gggcagatgt gtgaggcacc tgtggtgacc cgagagtggg    2400
tgttggacag tgtagcactc taccagtgcc aggagctgga cacctacctg ataccccaga    2460 tccccacag ccactactga ctgcagccag ccacaggtac agagccacag gaccccaaga    2520
atgagcttac aaagtggcct ttccaggccc tgggagctcc tctcactctt cagtccttct    2580
actgtcctgg ctactaaata ttttatgtac atcagcctga aaaggacttc tggctatgca    2640
agggtccctt aaagattttc tgcttgaagt ctcccttgga aatctgccat gagcacaaaa    2700
ttatggtaat ttttcacctg agaagatttt aaaaccattt aaacgccacc aattgagcaa    2760
gatgctgatt cattatttat cagccctatt cttttctattc aggctgttgt tggcttaggg    2820
ctggaagcac agagtggctt ggcctcaaga gaatagctgg tttccctaag tttacttctc    2880
taaaaccctg tgttcacaaa ggcagagagt cagacccttc aatggaagga gagtgcttgg    2940
gatcgattat gtgacttaaa gtcagaatag tccttgggca gttctcaaat gttggagtgg    3000
aacattgggg aggaaattct gaggcaggta ttagaaatga aaggaaact tgaaacctgg    3060 gcatggtggc tcacgcctgt aatcccagca ctttgggagg ccaaggtggg cagatcactg    3120
gaggtcagga gttcgaaacc agcctggcca acatggtgaa accccatctc tactaaaaat    3180
acagaaatta gccggtcatg gtggtggaca cctgtaatcc cagctactca ggtggctaag    3240
gcaggagaat cacttcagcc cgggaggtgg aggttgcagt gagccaagat cataccacgg    3300
cactccagcc tgggtgacag tgagactgtg gctcaaaaaa aaaaaaaaa aaaggaaaat    3360 gaaactagaa gagatttcta aaagtctgag atatatttgc tagatttcta aagaatgtgt    3420
tctaaaacag cagaagattt tcaagaaccg gtttccaaag acagtcttct aattcctcat    3480
tagtaataag taaaatgttt attgttgtag ctctggtata taatccattc ctcttaaaat    3540
ataagacctc tggcatgaat atttcatatc tataaaatga cagatcccac caggaaggaa    3600
gctgttgctt tctttgaggt gatttttttc ctttgctccc tgttgctgaa accatacagc    3660
ttcataaata atttttgcttg ctgaaggaag aaaaagtgtt tttcataaac ccattatcca    3720
```

| | | |
|---|---|---|
| ggactgttta tagctgttgg aaggactagg tcttccctag ccccccagt gtgcaagggc | 3780 | |
| agtgaagact tgattgtaca aaatacgttt tgtaaatgtt gtgctgttaa cactgcaaat | 3840 | |
| aaacttggta gcaaacactt caaaaaaaaa aaaaaaaa | 3879 | |

<210> SEQ ID NO 11
<211> LENGTH: 3759
<212> TYPE: DNA
<213> ORGANISM: Homo sapien

<400> SEQUENCE: 11

| | |
|---|---|
| cttagcggta gccccttggt ttccgtggca acggaaaagc gcgggaatta cagataaatt | 60 |
| aaaactgcga ctgcgcggcg tgagctcgct gagacttcct ggacggggga caggctgtgg | 120 |
| ggtttctcag ataactgggc ccctgcgctc aggaggcctt caccctctgc tctgggtaaa | 180 |
| gttcattgga acagaaagaa atggatttat ctgctcttcg cgttgaagaa gtacaaaatg | 240 |
| tcattaatgc tatgcagaaa atcttagagt gtcccatctg tctggagttg atcaaggaac | 300 |
| ctgtctccac aaagtgtgac cacatatttt gcaaattttg catgctgaaa cttctcaacc | 360 |
| agaagaaagg gccttcacag tgtccttat gtaagaatga taaccaaa aggagcctac | 420 |
| aagaaagtac gagatttagt caacttgttg aagagctatt gaaaatcatt tgtgcttttc | 480 |
| agcttgacac aggtttggag tatgcaaaca gctataattt tgcaaaaaag gaaaataact | 540 |
| ctcctgaaca tctaaaagat gaagtttcta tcatccaaag tatgggctac agaaaccgtg | 600 |
| ccaaaagact tctacagagt gaacccgaaa atcccttcctt gcaggaaacc agtctcagtg | 660 |
| tccaactctc taaccttgga actgtgagaa ctctgaggac aaagcagcgg atacaacctc | 720 |
| aaaagacgtc tgtctacatt gaattggctg cttgtgaatt ttctgagacg gatgtaacaa | 780 |
| atactgaaca tcatcaaccc agtaataatg atttgaacac cactgagaag cgtgcagctg | 840 |
| agaggcatcc agaaaagtat cagggtgaag cagcatctgg gtgtgagagt gaaacaagcg | 900 |
| tctctgaaga ctgctcaggg ctatcctctc agagtgacat tttaaccact cagcagaggg | 960 |
| ataccatgca ataacctg ataaagctcc agcaggaaat ggctgaacta gaagctgtgt | 1020 |
| tagaacagca tgggagccag ccttctaaca gctacccttc catcataagt gactcttctg | 1080 |
| ccccttgagga cctgcgaaat ccagaacaaa gcacatcaga aaaagcagta ttaacttcac | 1140 |
| agaaaagtag tgaataccct ataagccaga tccagaagg cctttctgct gacaagtttg | 1200 |
| aggtgtctgc agatagttct accagtaaaa ataaagaacc aggagtggaa aggtcatccc | 1260 |
| cttctaaatg cccatcatta gatgataggg ggtacatgca cagttgctct gggagtcttc | 1320 |
| agaatagaaa ctacccatct caagaggagc tcattaaggt tgttgatgtg gaggagcaac | 1380 |
| agctggaaga gtctgggcca cacgatttga cggaaacatc ttacttgcca aggcaagatc | 1440 |
| tagagggaac cccttacctg gaatctggaa tcagcctctt ctctgatgac cctgaatctg | 1500 |
| atccttctga agacagagcc ccagagtcag ctcgtgttgg caacatacca tcttcaacct | 1560 |
| ctgcattgaa agttccccaa ttgaaagttg cagaatctgc ccagagtcca gctgctgctc | 1620 |
| atactactga tactgctggg tataatgcaa tggaagaaag tgtgagcagg gagaagccag | 1680 |
| aattgacagc ttcaacagaa agggtcaaca aaagaatgtc catggtggtg tctggcctga | 1740 |
| ccccagaaga atttatgctc gtgtacaagt ttgccagaaa acaccacatc actttaacta | 1800 |
| atctaattac tgaagagact actcatgttg ttatgaaaac agatgctgag tttgtgtgtg | 1860 |
| aacggacact gaaatatttt ctaggaattg cgggaggaaa atgggtagtt agctatttct | 1920 |
| gggtgaccca gtctattaaa gaaagaaaaa tgctgaatga gcatgatttt gaagtcagag | 1980 |

-continued

| | |
|---|---|
| gagatgtggt caatggaaga aaccaccaag gtccaaagcg agcaagagaa tcccaggaca | 2040 |
| gaaagatctt caggggcta gaaatctgtt gctatgggcc cttcaccaac atgcccacag | 2100 |
| atcaactgga atggatggta cagctgtgtg gtgcttctgt ggtgaaggag ctttcatcat | 2160 |
| tcacccttgg cacaggtgtc cacccaattg tggttgtgca gccagatgcc tggacagagg | 2220 |
| acaatggctt ccatgcaatt gggcagatgt gtgaggcacc tgtggtgacc cgagagtggg | 2280 |
| tgttggacag tgtagcactc taccagtgcc aggagctgga cacctacctg ataccccaga | 2340 |
| tcccccacag ccactactga ctgcagccag ccacaggtac agagccacag gaccccaaga | 2400 |
| atgagcttac aaagtggcct ttccaggccc tgggagctcc tctcactctt cagtccttct | 2460 |
| actgtcctgg ctactaaata tttatgtac atcagcctga aaaggacttc tggctatgca | 2520 |
| agggtcccctt aaagattttc tgcttgaagt ctcccttgga aatctgccat gagcacaaaa | 2580 |
| ttatggtaat ttttcacctg agaagatttt aaaaccattt aaacgccacc aattgagcaa | 2640 |
| gatgctgatt cattatttat cagccctatt ctttctattc aggctgttgt tggcttaggg | 2700 |
| ctggaagcac agagtggctt ggcctcaaga gaatagctgg tttccctaag tttacttctc | 2760 |
| taaaaccctg tgttcacaaa ggcagagagt cagacccttc aatggaagga gagtgcttgg | 2820 |
| gatcgattat gtgacttaaa gtcagaatag tccttgggca gttctcaaat gttggagtgg | 2880 |
| aacattgggg aggaaattct gaggcaggta ttagaaatga aaggaaact tgaaacctgg | 2940 |
| gcatggtggc tcacgcctgt aatcccagca ctttgggagg ccaaggtggg cagatcactg | 3000 |
| gaggtcagga gttcgaaacc agcctggcca acatggtgaa accccatctc tactaaaaat | 3060 |
| acagaaatta gccggtcatg gtggtggaca cctgtaatcc cagctactca ggtggctaag | 3120 |
| gcaggagaat cacttcagcc cgggaggtgg aggttgcagt gagccaagat cataccacgg | 3180 |
| cactccagcc tgggtgacag tgagactgtg gctcaaaaaa aaaaaaaaa aaaggaaaat | 3240 |
| gaaactagaa gagatttcta aaagtctgag atatatttgc tagatttcta aagaatgtgt | 3300 |
| tctaaaacag cagaagattt tcaagaaccg gtttccaaag acagtcttct aattcctcat | 3360 |
| tagtaataag taaatgtttt attgttgtag ctctggtata taatccattc ctcttaaaat | 3420 |
| ataagacctc tggcatgaat atttcatatc tataaaatga cagatcccac caggaaggaa | 3480 |
| gctgttgctt tctttgaggt gatttttttc ctttgctccc tgttgctgaa accatacagc | 3540 |
| ttcataaata attttgcttg ctgaaggaag aaaaagtgtt tttcataaac ccattatcca | 3600 |
| ggactgttta tagctgttgg aaggactagg tcttccctag cccccccagt gtgcaagggc | 3660 |
| agtgaagact tgattgtaca aaatacgttt tgtaaatgtt gtgctgttaa cactgcaaat | 3720 |
| aaacttggta gcaaacactt caaaaaaaaa aaaaaaaa | 3759 |

<210> SEQ ID NO 12
<211> LENGTH: 3271
<212> TYPE: DNA
<213> ORGANISM: Homo sapien

<400> SEQUENCE: 12

| | |
|---|---|
| cttagcggta gccccttggt ttccgtggca acggaaaagc gcgggaatta agataaatta | 60 |
| aaactgcgac tgcgcggcgt gagctcgctg agacttcctg gacggggac aggctgtggg | 120 |
| gtttctcaga taactgggcc cctgcgctca ggaggccttc accctctgct ctggttcatt | 180 |
| ggaacagaaa gaaatggatt tatctgctct tcgcgttgaa gaagtacaaa atgtcattaa | 240 |
| tgctatgcag aaaatcttag agtgtccat ctgtctggag ttgatcaaga acctgtctcc | 300 |
| acaaagtgtg accacatatt ttgcaaattt tgcatgctga aacttctcaa ccagaagaaa | 360 |

```
gggccttcac agtgtccttt atgtaagaat gatataacca aaaggagcct acaagaaagt    420
acgagattta gtcaacttgt tgaagagcta ttgaaaatca tttgtgcttt tcagcttgac    480
acaggtttgg agtatgcaaa cagctataat tttgcaaaaa aggaaaataa ctctcctgaa    540
catctaaaag atgaagtttc tatcatccaa agtatgggct acagaaaccg tgccaaaaga    600
cttctacaga gtgaacccga aaatccttcc ttgcaggaaa ccagtctcag tgtccaactc    660
tctaaccttg gaactgtgag aactctgagg acaaagcagc ggatacaacc tcaaaagacg    720
tctgtctaca ttgaattggg atctgattct tctgaagata ccgttaataa ggcaacttat    780
tgcagtgtgg gagatcaaga attgttacaa atcacccctc aaggaaccag ggatgaaatc    840
agtttggatt ctgcaaaaaa ggctgcttgt gaattttctg agacggatgt aacaaatact    900
gaacatcatc aacccagtaa taatgatttg aacaccactg agaagcgtgc agctgagagg    960
catccagaaa agtatcaggg tgaagcagca tctgggtgtg agagtgaaac aagcgtctct   1020
gaagactgct cagggctatc ctctcagagt gacattttaa ccactcagca gagggatacc   1080
atgcaacata acctgataaa gctccagcag gaaatggctg aactagaagc tgtgttagaa   1140
cagcatggga gccagccttc taacagctac ccttccatca taagtgactc ttctgccctt   1200
gaggacctgc gaaatccaga acaaagcaca tcagaaaaag tattaacttc acagaaaagt   1260
agtgaatacc ctataagcca gaatccgaaa ggcctttctg ctgacaagtt tgaggtgtct   1320
gcagatagtt ctaccagtaa aaataaagaa ccaggagtgg aaaggtcatc cccttctaaa   1380
tgcccatcat tagatgatag gtggtacatg cacagttgct ctgggagtct tcagaataga   1440
aactacccat ctcaagagga gctcattaag gttgttgatg tggaggagca acagctggaa   1500
gagtctgggc cacacgattt gacggaaaca tcttacttgc caaggcaaga tctagaggga   1560
accccttacc tggaatctgg aatcagcctc ttctctgatg accctgaatc tgatccttct   1620
gaagacagag ccccagagtc agctcgtgtt ggcaacatac catcttcaac ctctgcattg   1680
aaagttcccc aattgaaagt tgcagaatct gcccagagtc cagctgctgc tcatactact   1740
gatactgctg gtataatgc aatggaagaa agtgtgagca gggagaagcc agaattgaca   1800
gcttcaacag aaagggtcaa caaaagaatg tccatggtgg tgtctggcct gaccccagaa   1860
gaatttatgc tcgtgtacaa gtttgccaga aaacaccaca tcactttaac taatctaatt   1920
actgaagaga ctactcatgt tgttatgaaa acagatgctg agtttgtgtg tgaacggaca   1980
ctgaaatatt ttctaggaat tgcgggagga aaatgggtag ttagctattt ctgggtgacc   2040
cagtctatta agaaagaaa aatgctgaat gagcatgatt ttgaagtcag aggagatgtg   2100
gtcaatggaa gaaaccacca aggtccaaag cgagcaagag aatcccagga cagaaagatc   2160 ttcaggggggc tagaaatctg ttgctatggg cccttcacca acatgcccac agggtgtcca   2220
cccaattgtg gttgtgcagc cagatgcctg gacagaggac aatggcttcc atgcaattgg   2280
gcagatgtgt gaggcacctg tggtgacccg agagtgggtg ttggacagtg tagcactcta   2340
ccagtgccag gagctggaca cctacctgat accccagatc ccccacagcc actactgact   2400
gcagccagcc acaggtacag agccacagga ccccaagaat gagcttacaa agtggccttt   2460
ccaggccctg ggagctcctc tcactcttca gtccttctac tgtcctggct actaaatatt   2520
ttatgtacat cagcctgaaa aggacttctg gctatgcaag ggtcccttaa agatttctg    2580 cttgaagtct cccttggaaa tctgccatga gcacaaaatt atggtaattt ttcacctgag   2640
aagattttaa aaccatttaa acgccaccaa ttgagcaaga tgctgattca ttatttatca   2700
gccctattct ttctattcag gctgttgttg gcttagggct ggaagcacag agtggcttgg   2760
```

```
cctcaagaga atagctggtt tccctaagtt tacttctcta aaaccctgtg ttcacaaagg    2820
cagagagtca gacccttcaa tggaaggaga gtgcttggga tcgattatgt gacttaaagt    2880
cagaatagtc cttgggcagt tctcaaatgt tggagtggaa cattggggag gaaattctga    2940
ggcaggtatt agaaatgaaa aggaaacttg aaacctgggc atggtggctc acgcctgtaa    3000
tcccagcact ttgggaggcc aaggtgggca gatcactgga ggtcaggagt tcgaaaccag    3060
cctggccaac atggtgaaac cccatctcta ctaaaaatac agaaattagc cggtcatggt    3120
ggtggacacc tgtaatccca gctactcggg tggctaaggc aggagaatca cttcagcccg    3180
ggaggtggag gttgcagtga gccaagatca taccacggca ctccagcctg ggtgacagtg    3240
agactgtggc tcaaaaaaaa aaaaaaaaaa a                                    3271

<210> SEQ ID NO 13
<211> LENGTH: 21
<212> TYPE: DNA
<213> ORGANISM: Artificial sequence
<220> FEATURE:
<223> OTHER INFORMATION: Synthetic

<400> SEQUENCE: 13
ctgggtagtt tgtaagcatg c                                                21

<210> SEQ ID NO 14
<211> LENGTH: 21
<212> TYPE: DNA
<213> ORGANISM: Artificial sequence
<220> FEATURE:
<223> OTHER INFORMATION: Synthetic

<400> SEQUENCE: 14
caataaactg ctggttctag g                                                21

<210> SEQ ID NO 15
<211> LENGTH: 21
<212> TYPE: DNA
<213> ORGANISM: Artificial sequence
<220> FEATURE:
<223> OTHER INFORMATION: Synthetic

<400> SEQUENCE: 15
ctgcgagcag tcttcagaaa g                                                21

<210> SEQ ID NO 16
<211> LENGTH: 26
<212> TYPE: DNA
<213> ORGANISM: Artificial sequence
<220> FEATURE:
<223> OTHER INFORMATION: Synthetic

<400> SEQUENCE: 16
atgacagaca gatccctcct atctcc                                           26

<210> SEQ ID NO 17
<211> LENGTH: 21
<212> TYPE: DNA
<213> ORGANISM: Artificial sequence
<220> FEATURE:
<223> OTHER INFORMATION: Synthetic

<400> SEQUENCE: 17
ctcatcactc gttgcatcga c                                                21

<210> SEQ ID NO 18
```

```
<211> LENGTH: 20
<212> TYPE: DNA
<213> ORGANISM: Artificial sequence
<220> FEATURE:
<223> OTHER INFORMATION: Synthetic

<400> SEQUENCE: 18
atctgccgtc caaattcaag                                                  20

<210> SEQ ID NO 19
<211> LENGTH: 21
<212> TYPE: DNA
<213> ORGANISM: Artificial sequence
<220> FEATURE:
<223> OTHER INFORMATION: Synthetic

<400> SEQUENCE: 19
ttccaaacag atcggacact c                                                21

<210> SEQ ID NO 20
<211> LENGTH: 24
<212> TYPE: DNA
<213> ORGANISM: Artificial sequence
<220> FEATURE:
<223> OTHER INFORMATION: Synthetic

<400> SEQUENCE: 20
aacagctacc cttccatcat aagt                                             24

<210> SEQ ID NO 21
<211> LENGTH: 27
<212> TYPE: DNA
<213> ORGANISM: Artificial sequence
<220> FEATURE:
<223> OTHER INFORMATION: Synthetic

<400> SEQUENCE: 21
gggtattcac tacttttctg tgaagtt                                          27

<210> SEQ ID NO 22
<211> LENGTH: 21
<212> TYPE: DNA
<213> ORGANISM: Artificial sequence
<220> FEATURE:
<223> OTHER INFORMATION: Synthetic

<400> SEQUENCE: 22
tggatgcagg gatgatgttc t                                                21

<210> SEQ ID NO 23
<211> LENGTH: 21
<212> TYPE: DNA
<213> ORGANISM: Artificial sequence
<220> FEATURE:
<223> OTHER INFORMATION: Synthetic

<400> SEQUENCE: 23
tgcaccacca actgcttagc c                                                21

<210> SEQ ID NO 24
<211> LENGTH: 20
<212> TYPE: DNA
<213> ORGANISM: Artificial sequence
<220> FEATURE:
<223> OTHER INFORMATION: Synthetic

<400> SEQUENCE: 24
```

```
tgatgggcag tcaacagcta                                        20

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25
agggtaaggt tcttgcccac                                        20

<210> SEQ ID NO 26
<211> LENGTH: 22
<212> TYPE: DNA
<213> ORGANISM: Artificial sequence
<220> FEATURE:
<223> OTHER INFORMATION: Synthetic

<400> SEQUENCE: 26
tgggaaaaac agaaaagagg tg                                     22

<210> SEQ ID NO 27
<211> LENGTH: 20
<212> TYPE: DNA
<213> ORGANISM: Artificial sequence
<220> FEATURE:
<223> OTHER INFORMATION: Synthetic

<400> SEQUENCE: 27
gtctccaatc tgagcagcaa                                        20

<210> SEQ ID NO 28
<211> LENGTH: 20
<212> TYPE: DNA
<213> ORGANISM: Artificial sequence
<220> FEATURE:
<223> OTHER INFORMATION: Synthetic

<400> SEQUENCE: 28
aagccttgaa tcagacggaa                                        20

<210> SEQ ID NO 29
<211> LENGTH: 20
<212> TYPE: DNA
<213> ORGANISM: Artificial sequence
<220> FEATURE:
<223> OTHER INFORMATION: Synthetic

<400> SEQUENCE: 29
tccctctagt tccccagatg                                        20

<210> SEQ ID NO 30
<211> LENGTH: 20
<212> TYPE: DNA
<213> ORGANISM: Artificial sequence
<220> FEATURE:
<223> OTHER INFORMATION: Synthetic

<400> SEQUENCE: 30
ctacctccac catgccaagt                                        20

<210> SEQ ID NO 31
<211> LENGTH: 20
<212> TYPE: DNA
<213> ORGANISM: Artificial sequence
<220> FEATURE:
```

```
<223> OTHER INFORMATION: Synthetic

<400> SEQUENCE: 31
agctgcgctg atagacatcc                                              20

<210> SEQ ID NO 32
<211> LENGTH: 26
<212> TYPE: DNA
<213> ORGANISM: Artificial sequence
<220> FEATURE:
<223> OTHER INFORMATION: Synthetic

<400> SEQUENCE: 32
caccagggct gcttttaact ctggta                                       26

<210> SEQ ID NO 33
<211> LENGTH: 24
<212> TYPE: DNA
<213> ORGANISM: Artificial sequence
<220> FEATURE:
<223> OTHER INFORMATION: Synthetic

<400> SEQUENCE: 33
ccttgacggt gccatggaat ttgc                                         24
```

METHOD FOR PREVENTING AND TREATING CARDIOVASCULAR DISEASES WITH BRCA1

This patent application is a continuation of U.S. Ser. No. 12/572,518 filed Oct. 2, 2009 now U.S. Pat. No. 8,110,185, which claims the benefit of priority from U.S. Provisional Application Ser. No. 61/102,609, filed Oct. 3, 2008, teachings of which are herein incorporated by reference in their entireties.

FIELD OF THE INVENTION

The present invention relates to methods for use of BRCA1 in prevention and treatment of cardiovascular diseases (CVD).

BACKGROUND OF THE INVENTION

BRCA1 (breast cancer susceptibility gene 1 (NM_007294.2)), is a tumor suppressor gene implicated in the hereditary predisposition to familial breast and ovarian cancers. A mutation in the BRCA1 gene significantly increases the risk of developing breast and ovarian cancer (Ford et al. Am J Hum Genet. 1998 62:676-689). Multiple references describe methods for treatment and/or diagnosis and/or prognosis of cancer based on BRCA1. See, e.g. U.S. Pat. No. 5,747,282.

BRCA1 is also involved in DNA repair and genome integrity (Scully and Livingston Nature 2000 408, 429-432). This nuclear protein has a role in DNA repair, transcription, ubiquitylation and cell cycle regulation (Deng et al. Bioessays 2000 22(8):728-737). BRCA1 potently inhibits genome instability by regulating expression of genes that are involved in DNA damage repair pathways (Deng et al. Hum Mol Genet. 2003 12 Spec No 1:R113-123). Murine embryos carrying a BRCA1-null mutation exhibit hypersensitivity to DNA damage and chromosomal abnormalities likely due to defective G2/M checkpoint control and improper centrosome duplication (Scully et al. Mol Cell. 1999 4(6):1093-1099; Somasundaram et al. Oncogene 1999 18(47):6605-6614). BRCA1-nullizygous mice show embryonic lethality in early stages of development that are associated with a proliferation deficit (Hakem et al. J Mammary Gland Biol Neoplasia 1998 3(4):431-445).

BRCA1 interacts directly and/or indirectly with many other proteins and signaling hubs including p53, which have been implicated in cardiac remodeling (Deng et al. Bioessays 2000 22(8):728-737). Although this relationship is complex, and contextual, recent studies demonstrate that BRCA1 exon11-knockout embryos die late in gestation as a result of widespread apoptosis but elimination of one p53 allele rescues this embryonic lethality (Xu et al. Nat Genet. 2001 28(3):266-271; Xu et al. Nat Genet. 1999 22(1):37-43).

BRCA1-deficient cells have been shown to have increased sensitivity to apoptosis induction in the presence of BARD1 and doxorubicin (Irminger-Finger et al. Molecular Cell 2001 8: 1255-1266; EP 1321522). Use of a BRCA1 construct in combination with BARD1 antisense to treat ischemic stroke or heart failure is suggested (EP 1321522).

WO 2006/015127 A2 describes using stem cells expressing at least one polypeptide selected from the group consisting of Oct4; DEK; BRCA1; Ect2; and MYC; at least one polypeptide selected from the group consisting of Fosb; NRAP; MEF2A; Furin; and TGFβ1; and at least one polypeptide selected from the group consisting of integral membrane protein 2A; insulin-like growth factor binding protein 4; thymus cell antigen 1, theta; selenoprotein P, plasma 1; and glycoprotein 38, for repairing cardiovascular tissue. The stem cells are administered to cardiovascular tissue and more specifically heart tissue.

Published U.S. Patent Application US 2006/0154252 discloses upregulation of BRCA1 during progression of an atherosclerotic plaque.

WO 2002/46466 describes use of a BRCA/STAT complex modulating compound comprising a STAT activating agent and a BRCA polypeptide or functional fragment thereof to inhibit cellular proliferation mediated by a BRCA/STAT complex. BRCA/STAT complex modulating compounds are suggested to reduce the rate or extent of proliferation useful in treating an individual having a vascular proliferative disorder such as atherosclerosis (WO 2002/46466).

SUMMARY OF THE INVENTION

An aspect of the present invention relates to use of BRCA1 to inhibit cardiomyocyte apoptosis and/or to improve cardiac function in a subject.

Another aspect of the present invention relates to use of BRCA1 in a subject at high risk or very high risk of developing cardiovascular disease, for example a subject with familial hypercholesterolemia.

Another aspect of the present invention relates to use of BRCA1 in a subject with peripheral artery disease wherein BRCA1 increase tissue neovascularization and enhances collateral blood flow of the tissue or limbs, i.e. extremities.

Another aspect of the present invention relates to use of BRCA1 in a subject having suffered a first acute coronary event to protect or inhibit the subject from suffering a second or subsequent coronary events.

Another aspect of the present invention relates to use of BRCA1 to inhibit or decrease cardiotoxicity in a subject receiving a cardiotoxic chemotherapeutic agent.

Another aspect of the present invention relates to use of BRCA1 to enhance efficacy of cardiotoxic chemotherapeutic agents by delivering to a subject receiving a cardiotoxic chemotherapeutic agent BRCA1 so that higher doses of the chemotherapeutic agent can be administered.

Another aspect of the present invention relates to use of BRCA1 to inhibit inflammation-induced apoptosis in endothelial cells. BRCA1 delivery is expected to be useful in the treatment of disorders linked to endothelial dysfunction including, but not limited to, pulmonary artery hypertension, systemic hypertension, diabetes, insulin resistance, sepsis, acute respiratory distress syndrome, and pregnancy induced hypertension, as well as atherosclerosis.

Another aspect of the present invention relates to use of BRCA1 to protect against or inhibit development of transplant atherosclerosis in response to immunosuppressants in a subject at risk.

Another aspect of the present invention relates to use of BRCA1 in a subject to prevent or reduce cardiac remodeling.

Another aspect of the present invention relates to use of BRCA1 in subject to treat diseases including, but not limited to coronary heart disease, coronary artery disease, peripheral artery disease, intermittent claudication and/or cerebral vascular disease, i.e. ischemic stroke.

Another aspect of the present invention relates to use of BRCA1 to decrease free fatty acid oxidation and fatty acid synthesis thereby treating dyslipidemia in a subject.

Another aspect of the present invention relates to assessing expression of BRCA1 or a BRCA1 mutant in a subject suffering from cancer to provide a pharmacogenomic basis to guide chemotherapeutic decision making.

BRIEF DESCRIPTION OF THE FIGURES

FIG. 2A is a bar graph showing levels of RNA isolated from the indicated organs, reverse transcribed and analyzed by real-time PCR. GADPH was used as an internal control (n=3 per group). FIG. 2B shows the PCR products run on an agarose gel. FIG. 2C is a bar graph showing the change in BRCA1 expression in remote myocardial tissue post-myocardial infarction over time. "*" is indicative of p<0.05 and "**" is indicative of p<0.01 vs sham operated mice (n=4 per group).

FIG. 4B shows results of nuclear protein extracted and resolved by SDS-PAGE and probed with anti-BRCA1 antibodies to determine the exogenous expression of BRCA1 in cultured cardiomyocytes. FIG. 4C shows an image at 200×magnification of cardiomyocytes transfected with ad-GFP (10 MOI). TFIIB was used as the loading control. "**" is indicative of p<0.01 vs GFP.

In FIG. 5A apoptosis in control, BRCA1-overexpressing, doxorubicin-treated and doxorubicin-treated-BRCA1-overexpressing neonatal rat ventricular cardiomyocytes (NRVCM) was assessed by Annexin V-FITC and propidium iodide staining coupled with flow cytometry. Quadrants S1, S2, S3 and S4 respectively represent necrotic, late apoptotic, viable live and early apoptotic NRVCM. FIG. 5B is a representative western blot of cleaved caspase-3 and α-actin proteins in NRVCM infected with either 10 MOI Ad-hBRCA1 or Ad-null vector for 48 hours before being exposed to 2 µM doxorubicin for 24 hours. Data are expressed as mean±SD. n=3. *P<0.05 vs untreated control group. †P<0.01 vs doxorubicin group. FIG. 5C is a representative western blot of Bax and α-actin proteins in murine hearts harvested 7 days after concomitant administration of Ad-hBRCA1 (40 µl of $10^{10}$ PFU, i.v.) and doxorubicin (10 mg/kg, i.p.).

FIG. 12A is a diagram depicting the positions of loxP sites flanking exon 11 of mouse BRCA1 gene and primer binding sites for polymerase chain reaction. Exon 11 is the largest exon of BRCA1 in the mouse and spans about 3.4 kb. As shown in FIG. 12B, Cre-mediated deletion of exon 11 of BRCA1 was predominantly detected only in the hearts of 12 week old mice, due to primer set 004 and 006, while in other organs except the heart, undeleted BRCA1 was detected due to primer set 004 and 005. In flox heterozygotes ($\alpha$MHC-Cre$^{tg/+}$; BRCA1$^{fl/+}$), where Cre transgene was present, partial deletion of BRCA1 alleles was detected as marked by the arrow.

FIG. 13A shows post-MI left ventricular infarct size of hearts from CM-BRCA1$^{+/-}$ and CM-BRCA1$^{-/-}$ as compared to WT mice. Representative H&E stained photomicrographs of LV sections from WT, CM-BRCA1$^{+/-}$ and CM-BRCA1$^{-/-}$ male mice 4 weeks after MI induction are provided. The scatter plot of LV infarct sizes is expressed as percent of infarcted endocardial perimeter to total endocardial perimeter (n=6-9, *$p<0.05$ vs WT). FIG. 13B shows the cross sectional area (CSA) of septal cardiomyocytes 4 weeks after MI induction. The scatter plot depicts the mean of approximately 300 transversely sectioned cardiomyocytes from the septal region of each heart, **$p<0.01$ vs WT. CM-BRCA1$^{+/-}$ and CM-BRCA1$^{-/-}$ mice, relative to WT mice. FIG. 13C shows heart to body weight (HW/BW) ratios. FIG. 13D shows left-ventricular radius-to-septum thickness (r/h) ratios (n=6-9, *$p<0.05$ vs WT). FIG. 13E shows LV compliance, as determined by the slope of the end-diastolic-pressure-volume relationship (EDPVR) in CM-BRCA1$^{+/-}$ and CM-BRCA1$^{-/-}$ mice compared to WT mice 4 weeks post-MI. FIG. 13F shows LV performance (ejection fraction and fractional shortening) 4 weeks post-MI induction, as measured by 2D-echocardiography in CM-BRCA1$^{+/-}$ and CM-BRCA1$^{-/-}$ mice relative to WT mice. n=4-6, **$p<0.01$, *$p<0.05$ vs WT. FIG. 13G shows M-mode representative photographs obtained after echocardiography from infarcted mice.

FIG. 14A provides Kaplan-Meier curves demonstrating the increased susceptibility of mice with cardiomyocyte (CM)-specific BRCA1 deletion to mortality related to MI. Left anterior descending coronary arteries were ligated to induce MI in 10-12 week old male WT (n=39), CM-BRCA1$^{+/-}$ (n=19) and CM-BRCA1$^{-/-}$ (n=18) mice. Loss of CM BRCA1 expression increased MI-associated mortality. *$p<0.05$ vs WT. FIG. 14B shows representative photographs of unruptured ventricles from WT mice and ruptured left ventricle (arrow) from CM-BRCA1$^{-/-}$ mice 2 days after coronary ligation.

FIG. 15A shows representative H&E stained sections of hearts from 10-12 week old male WT, CM-BRCA1$^{+/-}$ and CM-BRCA1$^{-/-}$ mice. FIG. 15B shows a cross sectional area (CSA) of septal cardiomyocytes, FIG. 15C shows heart weight-to-body weight (HW/BW) ratio. FIG. 15D shows LV radius-to-septum thickness (r/h).

FIG. 16A shows representative micrographs and the quantification of TUNEL-positive nuclei (arrowheads) in LV sections obtained from male CM-BRCA1$^{+/-}$ and CM-BRCA1$^{-/-}$ mice 4 weeks post-MI induction (n=4, approximately 1000 nuclei were counted over several fields of the remote myocardium. Data are mean±SD, **$p<0.01$ and *$p<0.05$ vs WT). FIG. 16B shows Bax and Bcl-2 levels 4 weeks post-MI. Values represent the changes in Bax/Bcl-2 ratios after normalization to GAPDH. n=3, *$p<0.05$ vs WT. FIG. 16C shows representative high resolution micrographs of TUNEL-positive nuclei (arrows) in the LV sections of male WT, CM-BRCA1$^{+/-}$ and CM-BRCA1$^{-/-}$ mice 4 weeks after MI induction. Nuclei and cardiomyocytes were visualized using Topro-3a staining and an Alexa-555-tagged $\alpha$-Myosin heavy chain antibody, respectively.

FIG. 21D). Positive values indicate fold increases and negative values indicate fold decreases relative to the control WT group. *$p<0.05$, **$p<0.01$ vs. WT.

In FIG. 23A ad-null or ad-BRCA1 infected HUVECs were treated with TNF$\alpha$ (20 ng/ml) for 24 hours. Cells were harvested for Annexin V-FITC and Propidium Iodide staining followed by flow cytometry. Total apoptotic cells are shown as mean±SD (n=3 in triplicate, p<0.01). In FIG. 23B, HUVECs were treated with either siBRCA1 (10 nM) or scrambled siRNA (10 nM) for 24 hours. BRCA1-silenced and control HUVECs were treated with TNFα (20 ng/ml), stained with Annexin V-FITC and Propidium Iodide, and analyzed by flow cytometry. The percentage of total apoptotic cells are presented as mean±SD (n=3 in triplicate, p<0.01). In FIG. 23C lysates from adenovirus-infected HUVECs treated with TNFα (20 ng/ml, 24 hours) were collected for cleaved caspase-3 and GAPDH western blot analysis. In FIG. 23D DNA extracted from ad-null or ad-BRCA1 infected HUVECs that had been treated with TNFα (20 ng/ml) for 24 hours was used for DNA fragmentation assay (M: Marker, lane 1: ad-null, lane 2: Ad-null+TNFα, lane 3: ad-BRCA1, lane 4: Ad-BRCA1+TNFα). In FIG. 23E ad-null or ad-BRCA1 infected HUVECs were treated with 2 µM doxorubicin for 24 hours before flow cytometry analysis was performed using Annexin V-FITC and Propidium Iodide staining. Data was calculated as the percentage of total apoptotic cells and presented as mean±SD (n=3 in triplicate, **p<0.01).

In FIG. 24A ad-null or ad-BRCA1 infected cells were trypsinized and seeded in the presence and absence of TNFα (20 ng/ml) on coated inserts and a colorimetric assay was performed after 24 hours. Migration was calculated as a percentage of ad-null controls. (n=4, **p<0.01). In FIG. 24B, ad-null or ad-BRCA1 infected HUVECs were seeded onto matrigel in the presence or absence of TNFα (20 ng/ml). Images were taken 5 hours after seeding (original magnification 20×). In FIG. 24C data was semi-quantitatively analyzed by counting tubular structures in four fields per group. Data is presented as mean±SD (n=3 in triplicate, *p<0.05, p<0.01). HUVECs infected with ad-null or ad-BRCA1 were treated for 24 hours with TNFα (20 ng/ml). VCAM1 (FIG. 24D, FIG. 24E), ICAM1 (FIG. 24F, FIG. 24G) and E-selectin (FIG. 24H, FIG. 24I) protein and transcript expression were determined in cell extracts via western blots and real-time PCR, respectively. GAPDH was used as a loading control for western blots and as a housekeeping gene for real-time PCR. Data are expressed as mean±SD (n=3, p<0.01).

In FIG. 25A cell cycle progression was assessed after adenoviral (ad-null or ad-BRCA1) infection of HUVECs and 24 hours of TNFα (20 ng/ml) treatment followed by Propidium Iodide staining coupled with flow cytometry. The percent of cells in $G_0/G_1$, S and $G_2$ phases are respectively indicated as C, E and I. FIG. 25B shows western blot analyses of GADD45, p21 and p53 from HUVEC extracts. GAPDH was used as a loading control.

FIG. 27B is a bar graph depicting data calculated as the recovery of blood flow to the ischemic foot normalized to the contralateral foot. Values are shown as mean±SEM (n=6), *p<0.05. FIG. 27C shows a time course for recovery of blood flow in the ischemic hind limb. Values are shown as mean±SEM (n=4-8), *p<0.05. FIG. 27D shows capillary density as determined in frozen gastrocnemius sections by rhodamine-conjugated isolectin-B4 (arrowheads). Arterioles were discriminated with FITC-conjugated smooth muscle α-actin (arrows). Quantitative results are represented as mean±SEM.

As shown in FIGS. 28A and 28C, TNFα markedly elevated eNOS protein levels in BRCA1-overexpressing cells. As shown in FIGS. 28B and 28D, TNFα significantly raised Akt activation in BRCA1-overexpressing cells as determined by western blotting. As shown in FIG. 28E VEGFa expression, as quantified by real-time PCR, was significantly increased in TNFα-treated BRCA1-overexpressing cells. Data are presented as mean±SEM of three independent experiments (*p<0.05, **p<0.01).

In FIG. 29A, HUVECs were treated with 10 ng/ml, 20 ng/ml or 50 ng/ml of TNFα for 24 hours before the extent of apoptosis was analyzed by flow cytometry coupled with Annexin V-FITC and propidium iodide staining. Quadrants S2 (Annexin V-FITC and PI positive cells) and S4 (Annexin V-FITC positive only) show early and late apoptotic endothelial cells, respectively. The percent of total apoptotic cells (S2+S4) are presented and represent three independent experiments performed in triplicates. **p<0.01 In FIG. 29B, proteins were extracted from HUVECs treated for 24 hours with TNFα (10 ng/ml, 20 ng/ml and 50 ng/ml). Cleaved caspase-3 and GAPDH (loading control) levels were determined by western blotting.

FIG. 30A shows GFP expression in HUVECs 24 hours after transfection with ad-GFP (20 MOI). Approximately 80% of the cells were positive for the green fluorescent protein. In FIG. 30B HUVECs were infected for 24 hours with 20 MOI of ad-null or ad-BRCA1. Proteins extracted from cell lysates were collected and subjected to western blotting. Immunoblots were probed with antibodies directed against BRCA1 and actin which acted as the loading control.

FIG. 32A is a representative micrograph of oil red O-defined atherosclerotic lesions and FIG. 32C shows quantification graphically of bordeaux-stained plaque areas in the aortic roots of individual ApoE$^{-/-}$ mice fed the Western diet for 4 weeks. N=5; *, P<0.01 vs. ad-null group. FIG. 32B shows representative oil red O-defined atherosclerotic lesions in en face preparations of descending aortas and FIG. 32D shows macrophage sequestration as defined by F4/80 staining in the aortic roots of ApoE$^{-/-}$ mice maintained on the Western diet for 16 weeks. Mice were administered ad-null or ad-BRCA1 every second week. N=6.

FIG. 33A is an illustration detailing where plaque containing and "normal" control sections were collected from carotid endarterectomy samples. FIG. 33B shows results of analysis of BRCA1 transcript levels in these samples. FIG. 33C shows results of analysis of BRCA1 protein levels in these samples. FIG. 33D shows results of BRCA1 immunohistochemical staining in these samples. N=3-4; *, P<0.05 vs. control group.

DETAILED DESCRIPTION OF THE INVENTION

Figure 1:
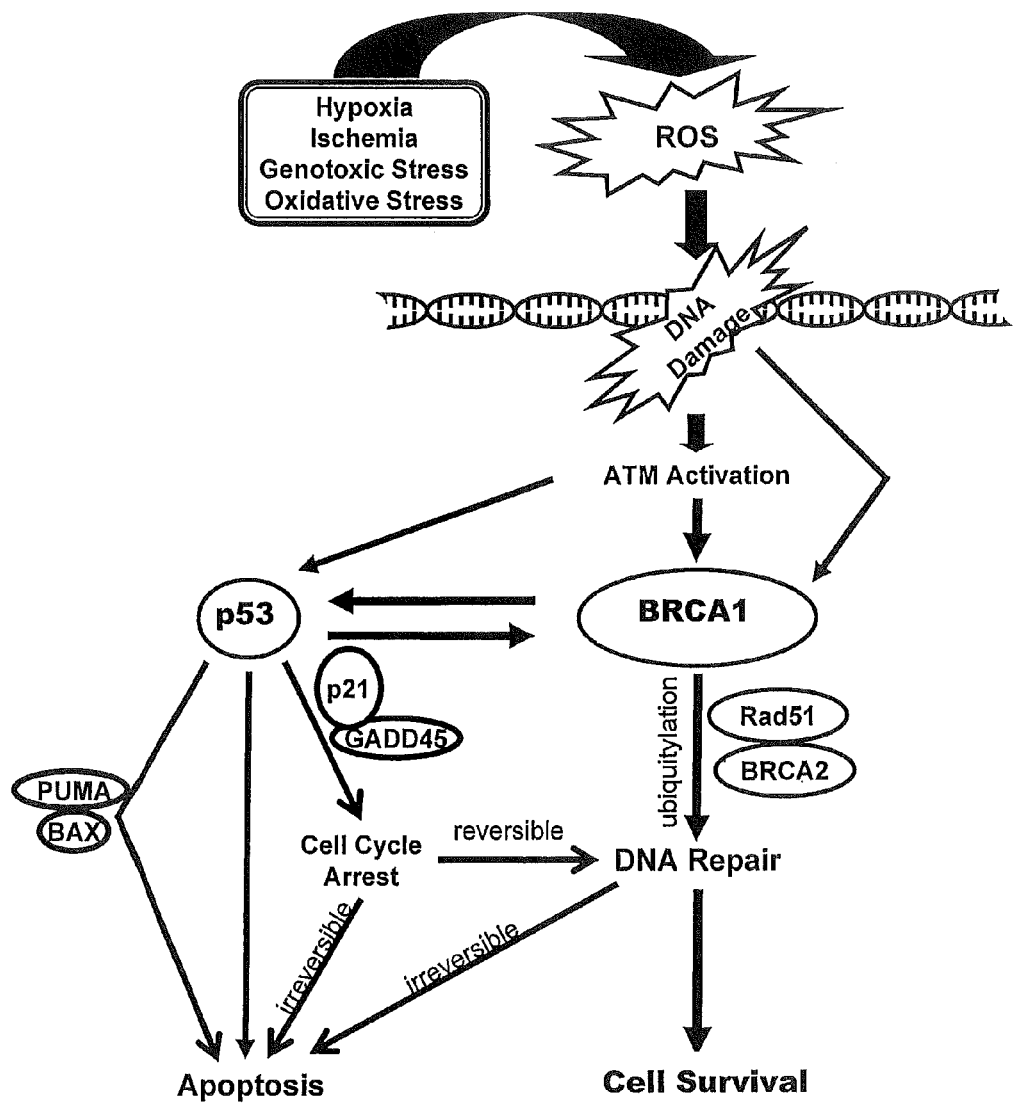
FIG. 1 is a diagram depicting BRCA1 and p53 Pathway as a Signaling Hub for Cell Survival and/or Death. Both BRCA1 and p53 can be phosphorylated by the ataxia telangiectasia mutated (ATM) kinases in response to DNA breaks caused by stressors that generate reactive oxygen species (ROS). DNA damage also directly causes BRCA1 to bind to a number of proteins (Rad51 and BRCA2), activate/co-activate p53 and promote protein ubiquitylation. Through its interaction with activated p53, BRCA1 can co-activate transcription of pro-apoptotic genes (Bax and PUMA) and/or cell cycle regulatory genes (p21 & Gadd45) resulting in apoptosis, cell cycle arrest or cell survival. Our preliminary data suggest that BRCA1 downregulates p53 in cardiomyocytes that have been subjected to hypoxic, genotoxic or ROS-induced stress thereby shifting the flux from apoptosis to cell survival.

Cardiovascular disease (CVD) is the single largest killer of adults in North America (Heart Disease and Stroke Statistics—2008 Update. A Report from the American Heart Association Statistics Committee and Stroke Statistics Subcommittee). CVD includes diseases caused by atherosclerosis, such as coronary heart disease (CHD), ischemic stroke and peripheral arterial disease (PAD). Atherosclerosis is a disease of the arterial blood vessel walls, resulting from endothelial cell dysfunction, high plasma cholesterol levels, foam cell formation and local inflammation. CHD is caused by the development and progression of atherosclerotic lesions in coronary arteries which results in acute coronary syndrome (ACS; i.e. unstable angina & myocardial infarction). In 2005 there were estimated to be 772,000 ACS patients in the U.S. (Heart Disease and Stroke Statistics—2008 Update. A Report from the American Heart Association Statistics Committee and Stroke Statistics Subcommittee). Approximately 1 in 5 deaths in 2004 were due to CHD, with a total U.S. and Canadian mortality of over 500,000 individuals. It is estimated that over 100 million North Americans have high blood cholesterol levels placing them in a border-line high risk, or high risk category of developing CHD. The total U.S. prevalence of ischemic stroke in 2005 was approximately 4.6 million and the annual incidence for both first time and recurrent attacks was around 780,000 (Abramson and Huckell, Can J Cardiol 2005 21(2): 997-1006). PAD is characterized by restricted blood flow to the extremities (e.g. legs, feet) resulting in cramping and in severe cases loss of the limb. According to the Society of Interventional Radiology, people over the age of 50 who smoke or have diabetes are at increased risk of developing PAD. Sixteen percent of individuals in North America have PAD. There are about 30 million people worldwide with PAD, half of which are asymptomatic. The estimated prevalence for PAD is 4% of the population over the age of 40 (Abramson and Huckell, Can J Cardiol 2005 21(2): 997-1006). The survival rate for severe symptomatic patients is approximately 25% (Abramson and Huckell Can J Cardiol 2005 21(2): 997-1006).

Changes in diet and increased aerobic exercise can significantly reduce the risk factors associated with CVD (Green et al. J Appl Physiol. 2008 105(2): 766-768). However, most individuals do not significantly change their life style habits but instead rely primarily upon pharmaceutical intervention for the alleviation of CVD (Kim and Beckles Am J Prev Med. 2004 27(1):1-7). There are a number of different classes of drugs to treat the different types of CVD. These include antihypertensives (e.g. COZAAR®; pharmaceutical preparation used in the treatment of hypertension; E.I. du Pont de Nemours and Company, Wilmington, Del.), antiplatelet agents (e.g. PLAVIX® (pharmaceutical preparations for the treatment of cardiovascular diseases; Sanofi-Aventis Corporation, Paris, France), anticoagulants (e.g. COUMADIN®; Hemorrhagic Producing Drug; Bristol-Myers Squibb Pharma Company Corporation, Wilmington, Del.), thrombolytics (Activase®; a tissue plasminogen activator; Genentech, Inc. Corporation South San Francisco, Calif.) and antihyperlipidemics (e.g. Lipitor®; pharmaceutical preparations for use in the treatment of cardiovascular disorders and cholesterol reduction; Pfizer Ireland Pharmaceuticals General Partnership, Dublin, Ireland).

When pharmaceutical intervention is unsuccessful in treating CVD, invasive medical procedures may be required. For example, severe atherosclerotic blockage of the coronary blood vessels may require treatment via percutaneous transluminal angioplasty (PTA) and/or coronary artery stent placement, or coronary artery bypass graft surgery (CABG). These procedures are not without significant risk (Raja and Dreyfus, J Card Surg. 2006 21(6):605-12; Smith et al. J ACC 2001 37(8):3019-3041). For example, there is a 1% to 2% chance of death resulting from CABG (Raja and Dreyfus, J Card Surg. 2006 21(6):605-12). Further, a significant percentage of patients will likely need a secondary procedure within a few years (e.g. due to restenosis; Raja and Dreyfus, J Card Surg. 2006 21(6):605-12; Kipshidze et al. Curr Pharm Des. 2004 10(4): 337-348).

Diverse cardiac insults, including hypoxia, ischemia, genotoxic stress and myocardial infarction, result in complex structural alterations, inciting both early and late adverse remodeling, heart failure and death (MacLellan and Schneider, Circ Res. 1997; 81(2):137-144; Kumar and Jugdutt, J Lab Clin Med. 2003; 142(5):288-297; Jessup and Brozena, N Engl J. Med. 2003; 348(20):2007-2018). These diverse pathophysiological stressors evoke marked changes in local and systemic signaling pathways, which in turn promote rapid cardiomyocyte apoptosis, a common pathway of cell death in this setting (Feuerstein, G. Z. Cardiovasc Drugs Ther. 1999; 13(4):289-294; Dorn and Brown, Trends Cardiovasc Med. 1999; 9(1-2):26-34; Bishopric et al. Curr Opin Pharmacol. 2001; 1(2):141-150). An imbalance between activation of apoptotic pathways and cell survival factors either through genetic and/or epigenetic pathways, determines the fate of cardiomyocytes, and their resistance to apoptosis. Preservation of structure and function of the myocardium is critically dependent upon improving the survival of existing cardiomyocytes, through strategies that limit cardiomyocyte apoptosis and DNA damage.

The inventors have now found that BRCA1 can be used to limit cardiomyocyte apoptosis, and prevent aberrant cardiac remodeling.

Figure 2A:
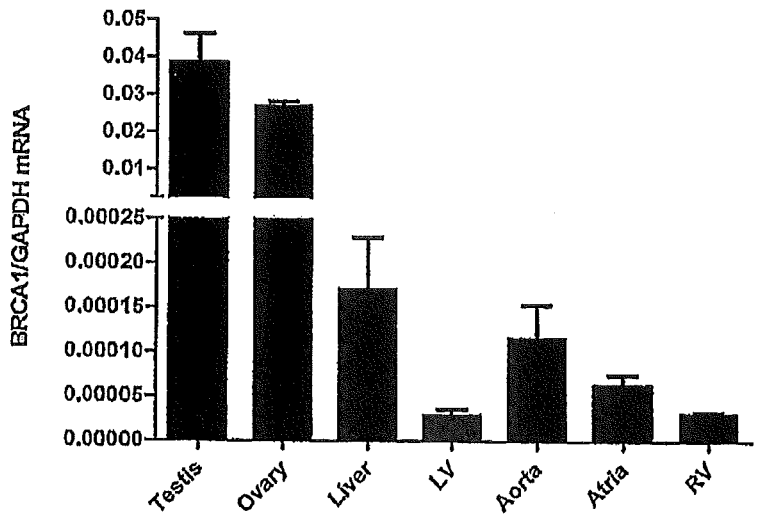
FIGS. 2A through 2C show results from experiments determining BRCA1 expression in the heart under basal conditions post myocardial infarction (MI) in mice.
Figure 2B:
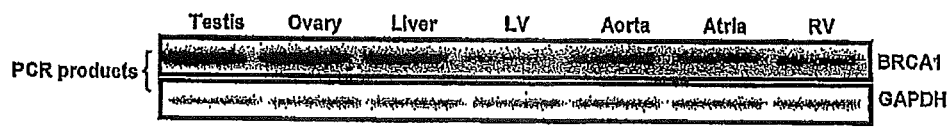
Figure 2C:
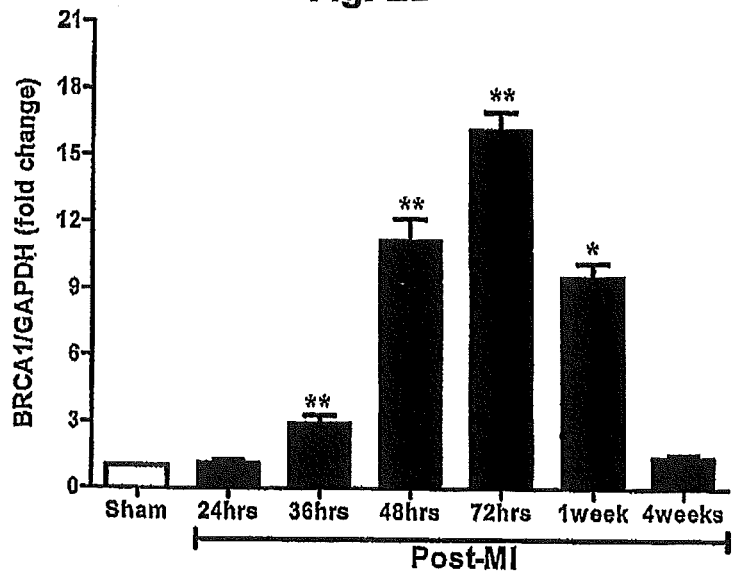

The inventors determined that BRCA1 is expressed in the heart under basal conditions and is markedly upregulated post myocardial infarction (MI). In these experiments, BRCA1 transcript expression in the ventricles, atria, aortas, livers, testes and ovaries of naïve wild-type mice as well as wild-type mice that had undergone experimental MI were evaluated by real-time PCR (n=3 per organ). Under basal conditions, BRCA1 was highly expressed in the testes and ovaries, and at a low level in left ventricular tissues (see FIGS. 2A and 2B). Post MI, the expression of endogenous BRCA1 mRNA in remote myocardial tissues rose significantly at 36 hours (3.1±1.0 fold, p<0.01), peaked at 72 hours (16.2±1.8 fold, p<0.01), declined at 1 week and returned to basal levels after 4 weeks compared with sham-operated mice (see FIG. 2C).

Figure 3A:
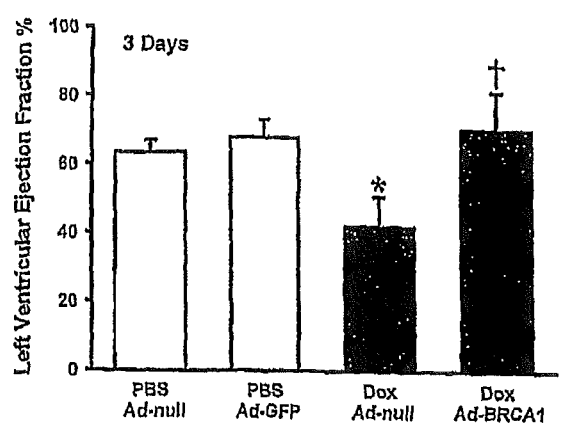
FIGS. 3A through 3C provide data from experiments demonstrating cardiac function is preserved after co-administration of Ad-hBRCA1 and doxorubicin in mice. Left ventricular function was assessed by echocardiography measuring percent systolic ejection fraction 3 days (FIG. 3A) or 7 days (FIG. 3B) after administration of vehicle, Ad-null vector (40 µl of $10^{10}$ PFU, i.v.), Ad-GFP (40 µl of $10^{10}$ PFU, i.v.), doxorubicin (10 mg/kg, i.p.) or doxorubicin (10 mg/kg, i.p.) with Ad-hBRCA1 (40 µl of $10^{10}$ PFU, i.v.). Left ventricular function was also assessed by measuring fractional shortening values 3 days (FIG. 3C) after administration of vehicle, Ad-null vector (40 µl of $10^{10}$ PFU, i.v.), Ad-GFP (40 µl of $10^{10}$ PFU, i.v.), doxorubicin (10 mg/kg, i.p.) or doxorubicin (10 mg/kg, i.p.) with Ad-hBRCA1 (40 µl of $10^{10}$ PFU, i.v.). *P<0.01 vs corresponding PBS group. †P<0.01 vs corresponding doxorubicin group. # p<0.01 vs. PBS+ad-GFP, ## p<0.001 vs. Dox+ad-BRCA1. n=3 for PBS and GFP groups; n=7 for doxorubicin and doxorubicin-BRCA1 groups.
Figure 3B:
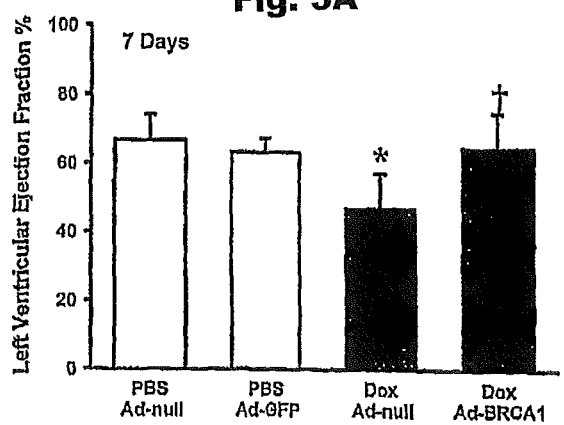
Figure 3C:
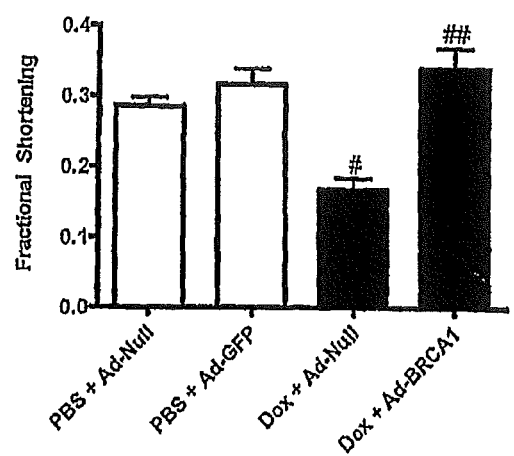
Figure 3D:
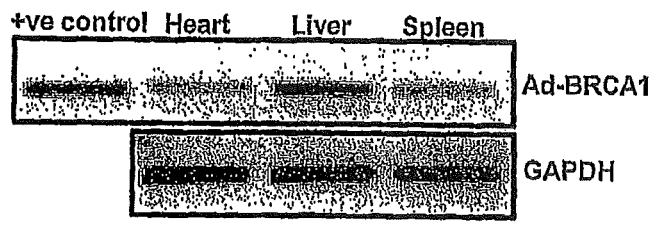
FIG. 3D shows exogenous expression of the human variant of BRCA1 in the left ventricle, liver and spleen by real-time PCR. PCR products were resolved on agarose gel with GAPDH used as the internal control. The plasmid containing the human variant of BRCA1 was used as the positive control.

The potential of systemic Ad-BRCA1 delivery to attenuate doxorubicin-induced cardiac dysfunction in mice was evaluated. Wild-type mice were treated with either Ad-null and phosphate buffered saline (PBS) (n=3), Ad-green fluorescent protein (GFP) and PBS (n=3), Ad-null and doxorubicin (10 mg/kg), or Ad-BRCA1 (401.11 of $10^{10}$ PFU/ml) and doxorubicin (n=7). Ad-null or Ad-BRCA1 was administered intravenously via the tail vein, whereas doxorubicin was administered intraperitoneally. Intravenous delivery of Ad-BRCA1 resulted in an increased myocardial expression of BRCA1. Echocardiography was performed by a double-blinded investigator at day 3 and day 7, post surgery, respectively, in all groups. Whereas doxorubicin resulted in an impairment in cardiac function, as assessed by percent systolic ejection fraction (FIG. 3A (day 3) and FIG. 3B (day 7)) and fractional shortening (FIG. 3C), Ad-BRCA1 systemic delivery completely prevented these phenotypes, as early as 3-days post-doxorubicin treatment.

Figure 4A:
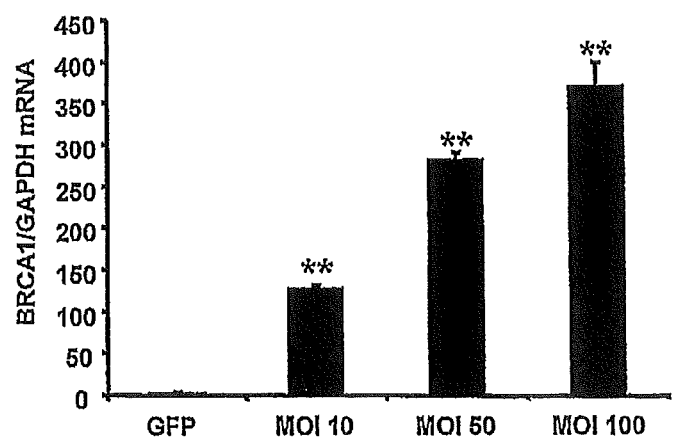
FIGS. 4A through 4C show optimization of adenoviral transfection. In the bar graph of FIG. 4A, RNA was isolated from culture cardiomyocytes after adenoviral transfection and examined for the expression of exogenous BRCA1. GAPDH was used as the internal control.
Figure 4B:
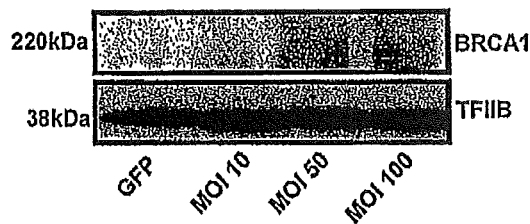
Figure 4C:
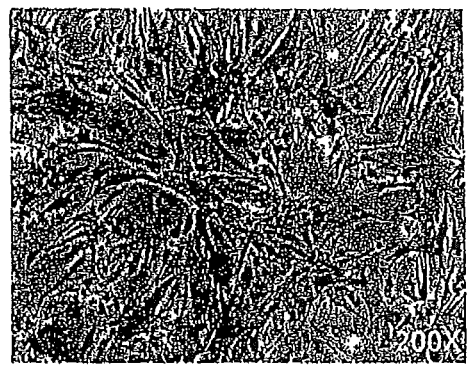
Figure 5A:
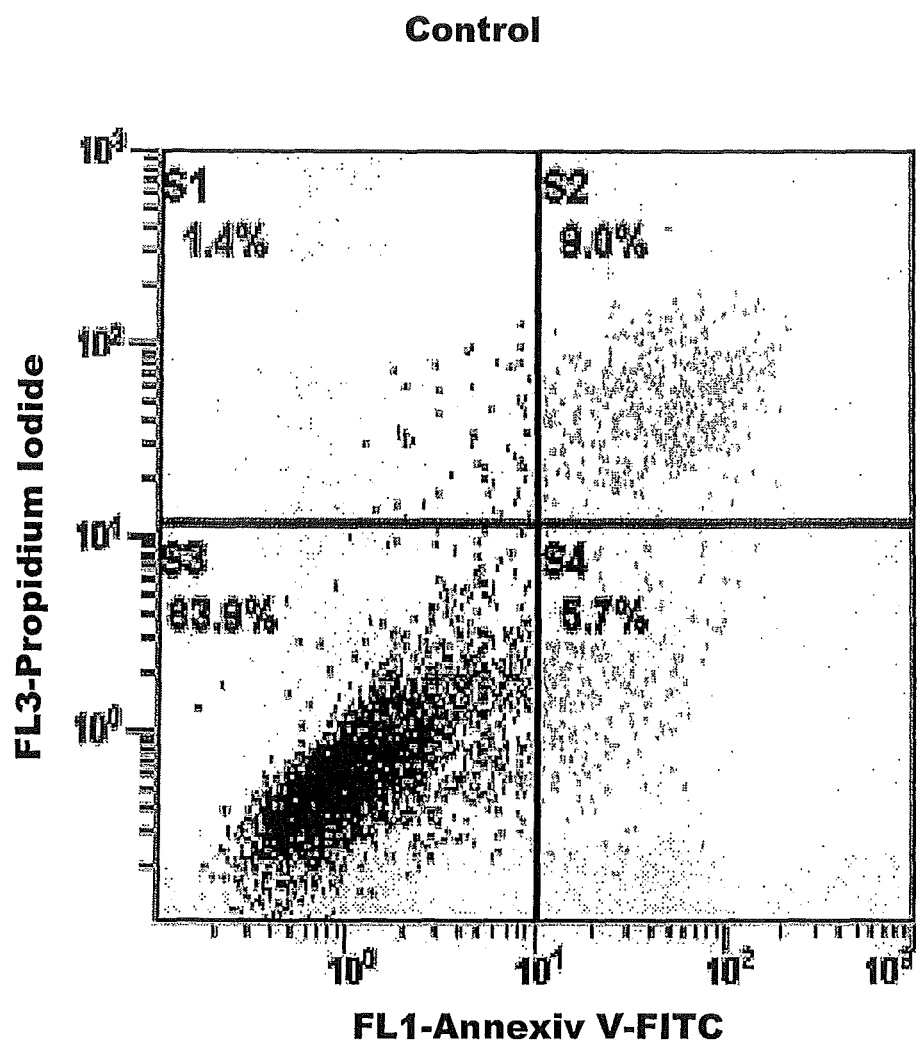
FIGS. 5A through 5C show results from experiments demonstrating BRCA1 overexpression confers protection against doxorubicin-induced myocyte apoptosis in mice.
Figure 5A:
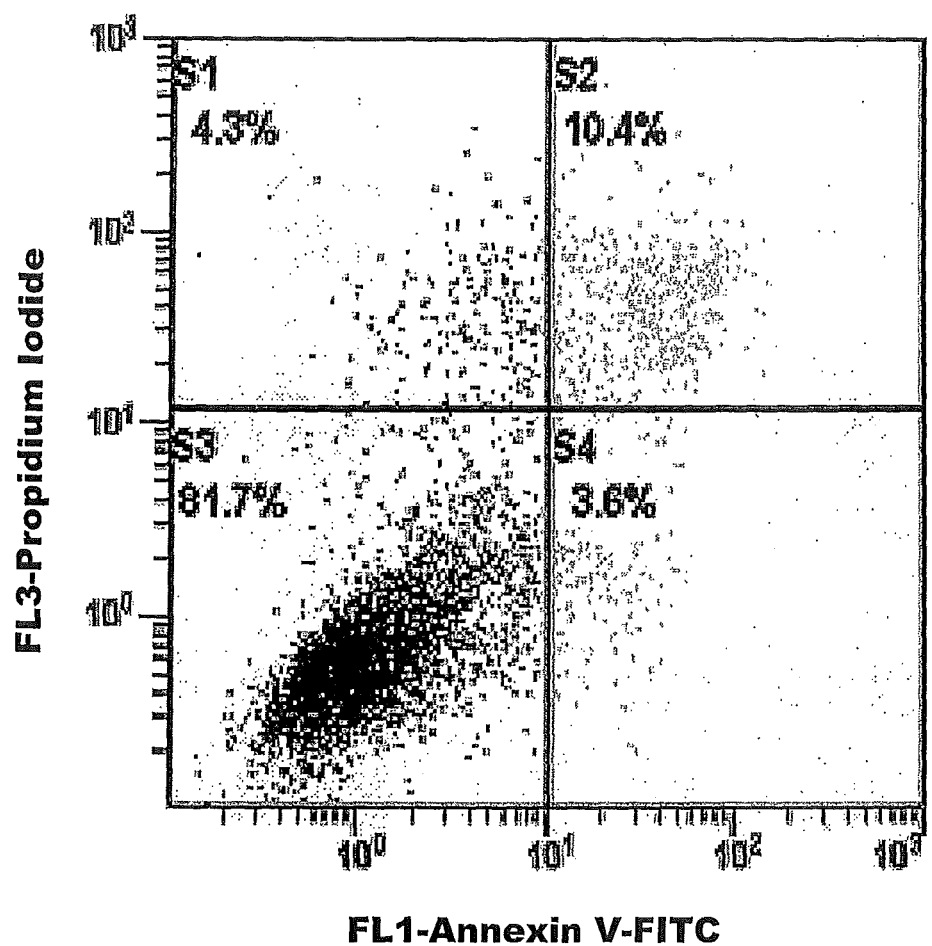
Figure 5A:
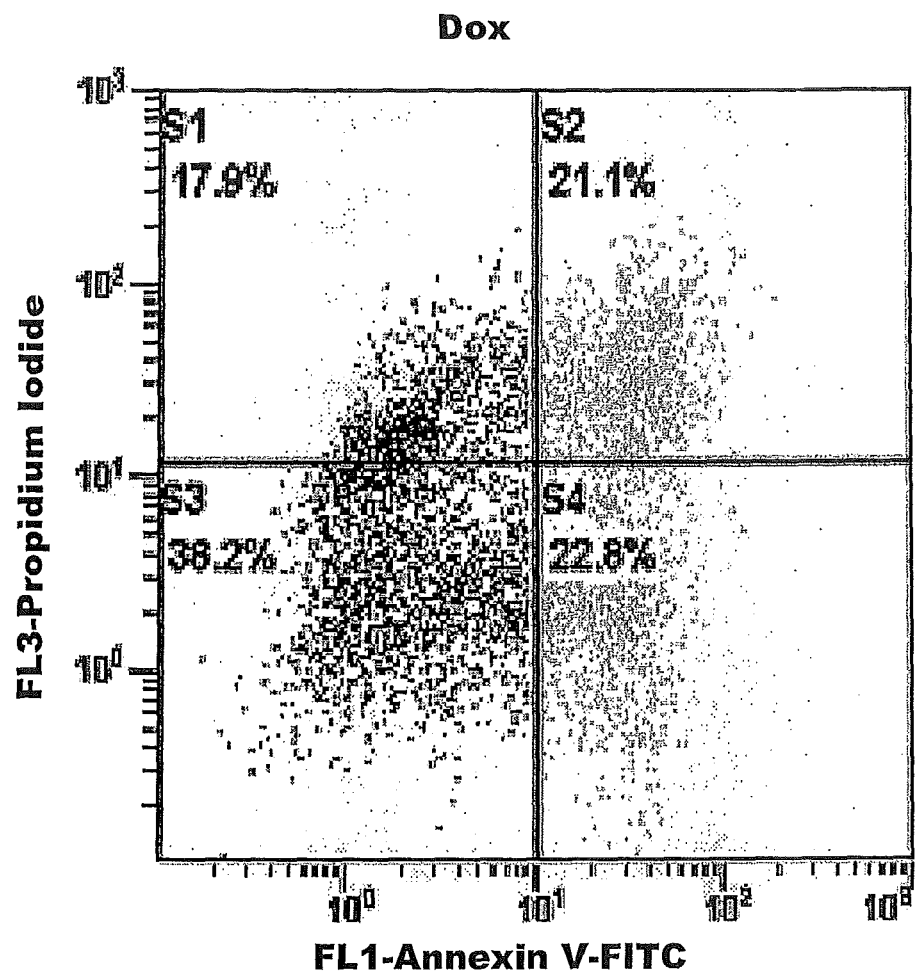
Figure 5A:
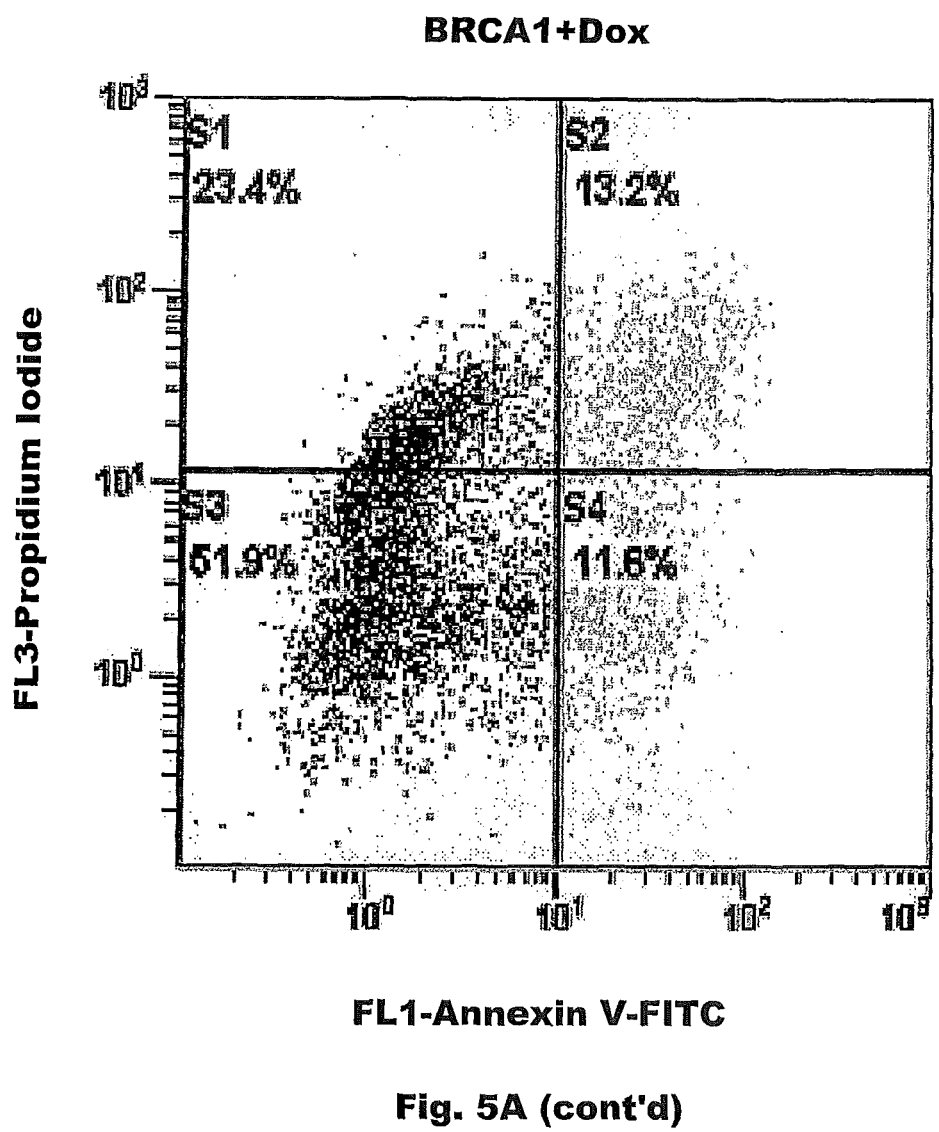
Figure 5C:
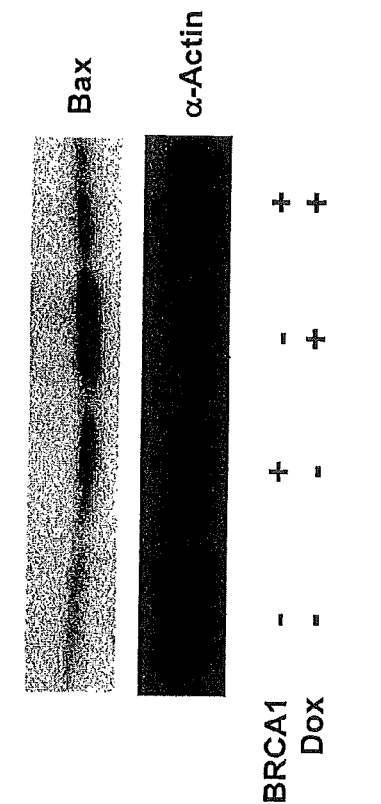
Figure 5B:
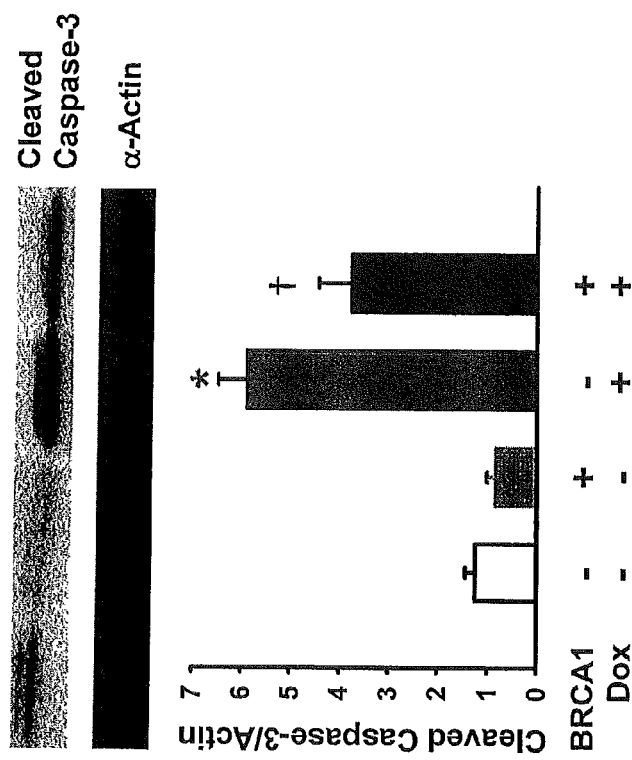
Figure 6:
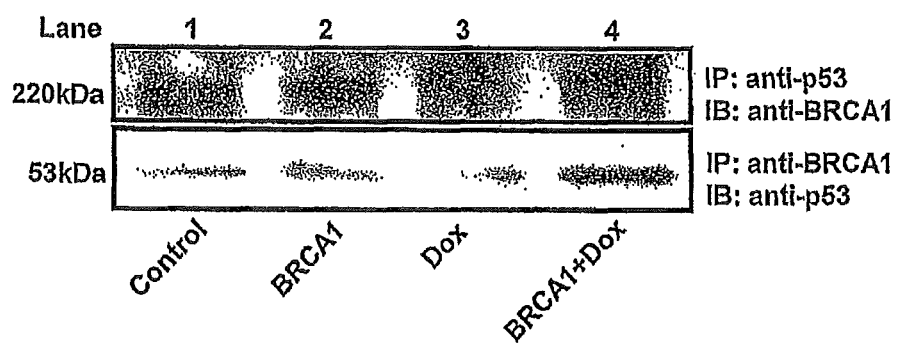
FIG. 6 shows results from co-immunoprecipitation analysis for BRCA1 and p53 interaction. BRCA1 physically interacts with p53 in order to regulate p53 activity in a context dependent manner. Proteins were extracted after treatment and equal amounts (100 µg) of lysates were resolved by SDS PAGE. The upper panel shows the immunoprecipitation with anti-p53 antibody and immunoblotting for BRCA1. The lower panel shows immunoprecipitation with anti-BRCA1 antibodies and immunoblotting for p53.

BRCA-1 induced gain of function and protection against genotoxic and oxidative stress-induced apoptosis was also examined in vitro. Cultured rat neonatal ventricular cardiomyocytes (NRVMs) were infected with 10, 50 and 100 MOIs of adenoviral construct to determine the optimum viral titer. Ad-GFP was used as a reporter construct. Cardiomyocytes were incubated with the virus (human BRCA1 or GFP) for 48 hours after which expression of human BRCA1 or GFP were determined. Expression of BRCA1 was analyzed by real-time PCR and western blotting (see FIGS. 4A and 4B) and expression of GFP was analyzed by live cell video microscopy. GFP expressing cells were found to comprise 95-980 of the total cell population and were beating at the time of imaging (see FIG. 4C). Based on this observation, 10 MOI was determined to be the best of the three tested concentrations of the adenoviral construct. Ad-BRCA1 overexpressing NRVMs were treated with either doxorubicin or hydrogen peroxide. Measurement of cardiomyocyte apoptosis was performed by flow cytometry (AnnexinV-FITC and PI staining) and western blotting (cleaved caspase-3). Ad-BRCA1 overexpressing NRVMs demonstrated a profound reduction in doxorubicin- and $H_2O_2$-induced apoptosis. See FIGS. 5A through 5C.

p53 has been suggested to play an important role in aberrant cardiac remodeling. Experiments were performed to access the interaction of BRCA1 with p53 in cardiomyocytes. A co-immunoprecipitation assay, which indicated that BRCA1 physically interacts with p53 in cardiomyocytes was performed. Overexpression of BRCA1 alone in cardiomyocytes upregulated BRCA1 and p53 association (lane 2, FIG. 6), while treatment of cardiomyocytes with doxorubicin alone led to a decline in this association (lane 3, FIG. 6). Additionally, doxorubicin treatment, in the presence of overexpressing BRCA1 strengthened this association (lane 4, FIG. 6). These data suggest that in cardiomyocytes, in response to doxorubicin, BRCA1 decreases the levels of p53 by physically associating with it.

Figure 7:
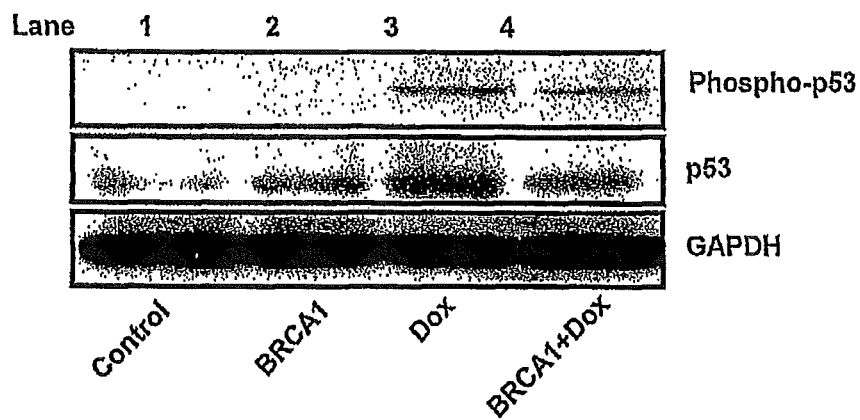
FIG. 7 shows results of western blot analysis for phosphorylated p53 and total p53 levels in cultured cardiomyocytes. GAPDH was used as loading control. Phospho-p53 antibodies were directed against serine 15 of p53 protein.

BRCA1 was demonstrated to protect NRVM via inhibition of p53 and phosphorylated p53. BRCA1 and doxorubicin, on their own, both upregulated p53 in a nearly identical manner (lane 2 and 3, FIG. 7). However, in BRCA1-overexpressing NRVMs, doxorubicin treatment resulted in significant reduction of total p53 expression (lane 4, FIG. 7) and a concomitant reduction in cardiomyocyte apoptosis (see FIG. 5). Doxorubicin also activated serine-15 phosphorylation of p53 and in the presence of BRCA1, a reduction in phospho-p53 was observed (lane 4, FIG. 7).

Figure 8A:
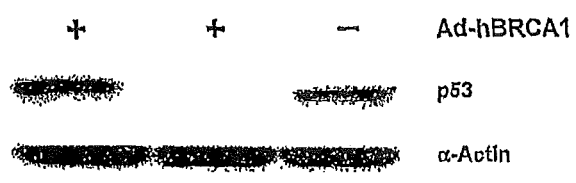
FIGS. 8A and 8B show representative western blots of p53 and α-actin in neonatal rat ventricular cardiomyocytes (NRVCM) infected with either 10 MOI AdhBRCA1 or Ad-null vector for 48 hours before being exposed for 24 hours to (FIG. 8A) a hypoxic environment (1% O2) or (FIG. 8B) $H_2O_2$ (50 µM). There was minimal expression of p53 in untreated control cells.
Figure 8B:
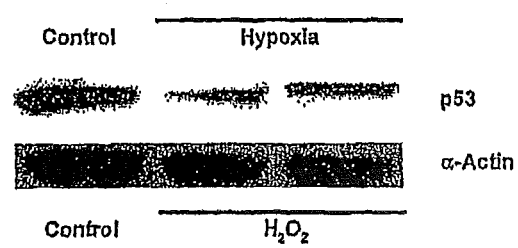

BRCA1 overexpressing neonatal rat ventricular cardiomyocytes (NRVCM) markedly limited the increase in p53 protein levels evoked by hypoxic stress or H2O2 (see FIGS. 8A and 8B).

Figure 9:
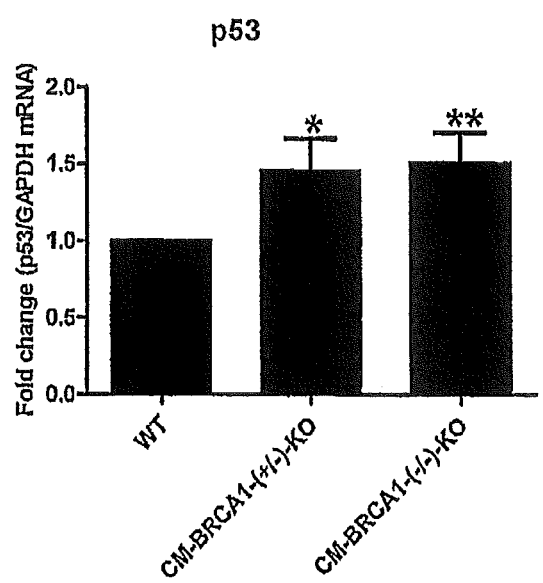
FIG. 9 shows results of cardiomyocyte (CM)-specific BRCA1 deletion on p53 expression in the heart. Total RNA was extracted from the hearts of 32-week old female mice (n=3 per group) to determine transcript levels of p53. *p<0.05, **p<0.01 vs. WT. GAPDH was used as internal control.

Cardiomyocyte (CM)-specific BRCA1 deletion induced p53 expression in the mouse heart (see FIG. 9) as measured by real-time PCR.

Figure 10:
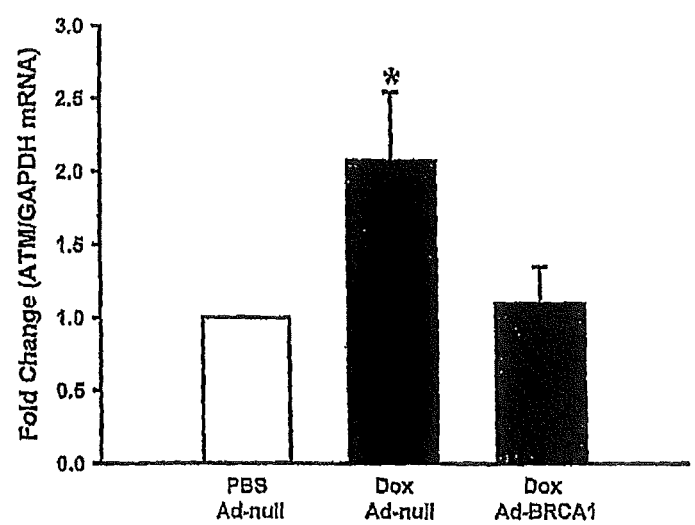
FIG. 10 is a bar graph depicting data from experiments demonstrating suppression of doxorubicin-evoked increase in cardiac ataxia-telangiectasia mutated (ATM) expression by Ad-hBRCA1 in mice. RNA was isolated from murine hearts 24 hours after administration of PBS, doxorubicin (10 mg/kg, i.p.) alone or in combination with Ad null vector (40 µl of $10^{10}$ PFU, i.v.) or Ad-hBRCA1 (40 µl of $10^{10}$ PFU, i.v.). ATM expression was determined by real-time PCR and normalized against corresponding GAPDH levels. Data are presented as mean±SD. n=3; *P<0.05 vs PBS group.

As shown in FIG. 10, ad-hBRCA1 also suppressed of doxorubicin-evoked increase in cardiac ataxia-telangiectasia mutated (ATM) expression by Ad-hBRCA1.

Figure 11:
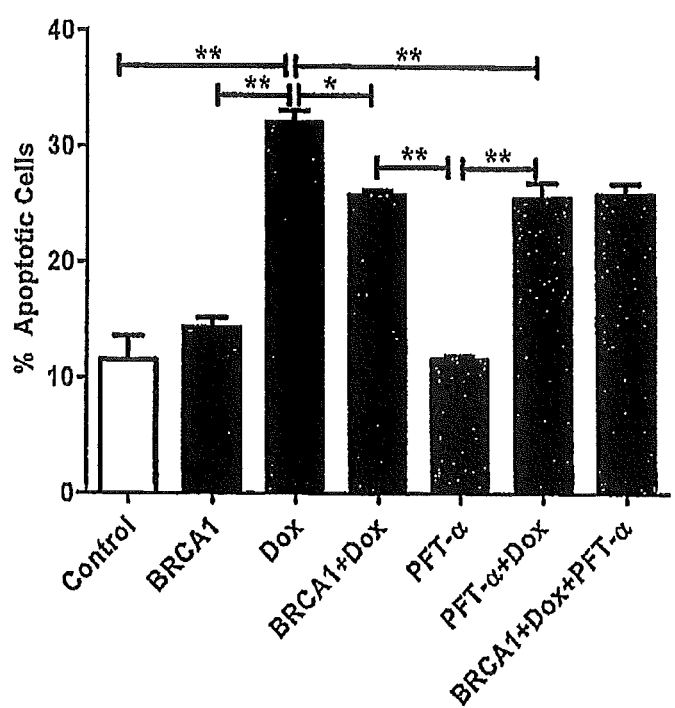
FIG. 11 shows results of flow cytometric analysis of AnnexinV positive cardiomyocytes after various treatments. The effect of pifithrin-α on doxorubicin-induced cardiomyocyte apoptosis, with or without overexpression of BRCA1 was examined. Three independent experiments were performed in triplicate. "*" is indicative of p<0.05 and "**" is indicative of p<0.01.

To further evaluate the potential role of BRCA1 to modulate p53 as a mechanism of cardioprotection, a chemical inhibitor of p53, pifithrin-α (PFT-α), which has been shown to inhibit p53-dependent apoptosis (Komarov et al. Science. 1999; 285(5434):1733-1737) was used. The addition of PFT-α to cardiomyocytes treated with doxorubicin led to significant reductions in the number of apoptotic cells (FIG. 11, $p<0.01$ vs doxorubicin only), indicating that doxorubicin-induced apoptosis is dependent on p53. BRCA1-overexpressing cardiomyocytes, when treated with doxorubicin and PFT-α both, showed no further reduction in number of apoptotic cardiomyocytes (see FIG. 11), quantitatively similar to the BRCA1 overexpression with doxorubicin treatment group respectively (see FIG. 11). These results indicate that BRCA1 mediated cardiomyocyte protection against doxorubicin requires p53.

Figure 12A:
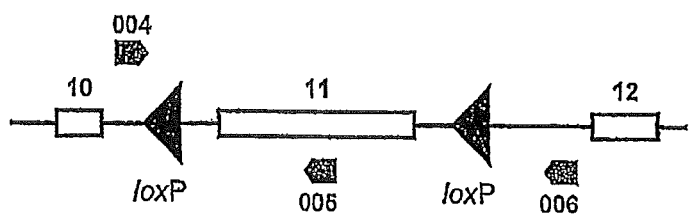
FIGS. 12A and 12B show results of cardiomyocyte specific inactivation of BRCA1 in mice.
Figure 12B:
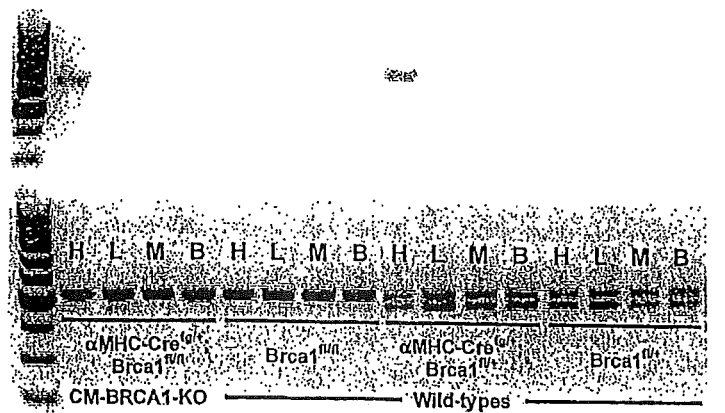
Figure 13A:
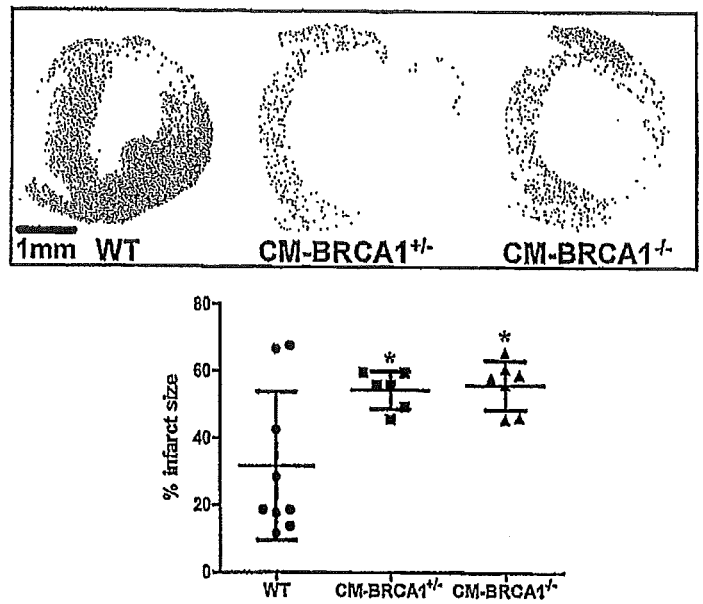
FIGS. 13A through 13G show results of cardiac remodeling and ventricular function in mice with cardiomyocyte (CM)-specific BRCA1 deletion following myocardial infarction (MI).
Figure 13B:
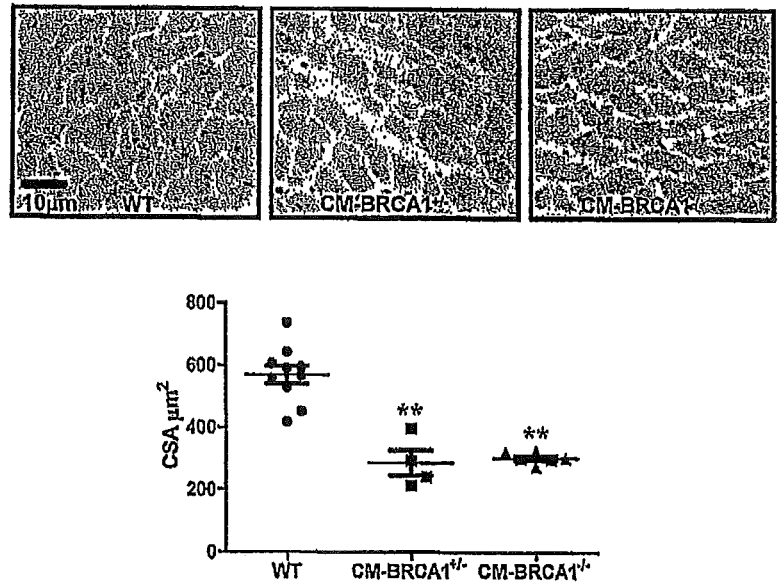
Figure 13C:
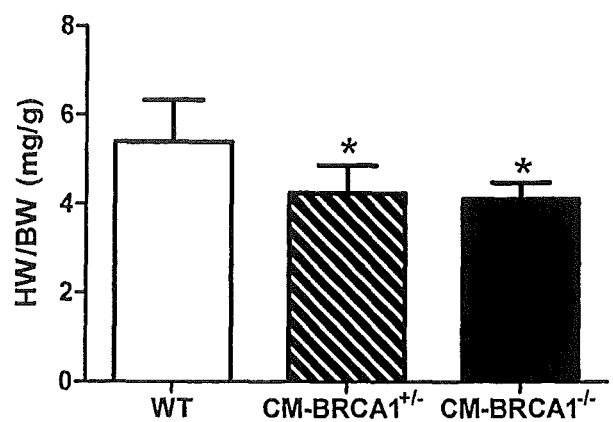
Figure 13D:
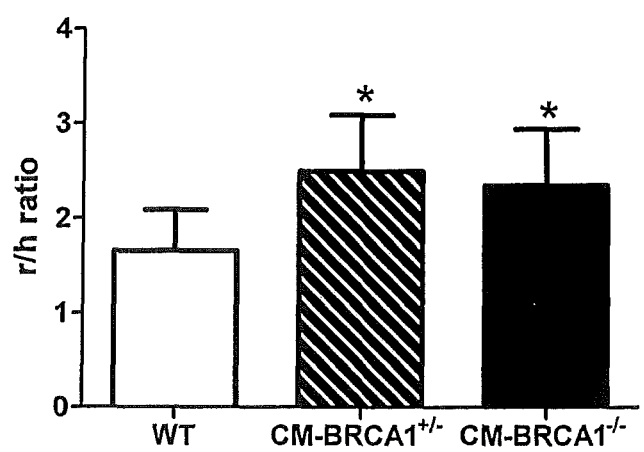
Figure 13E:
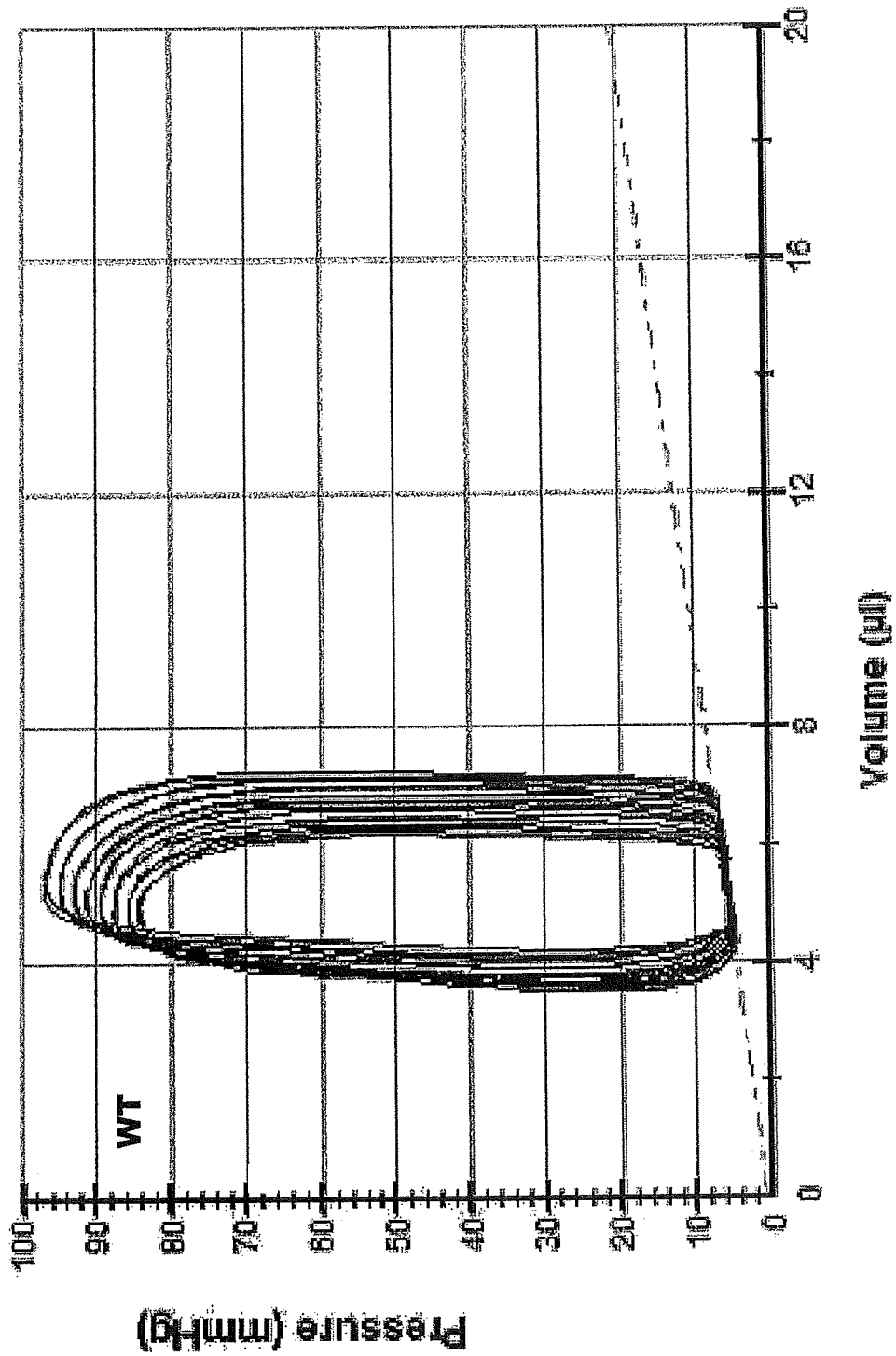
Figure 13E:
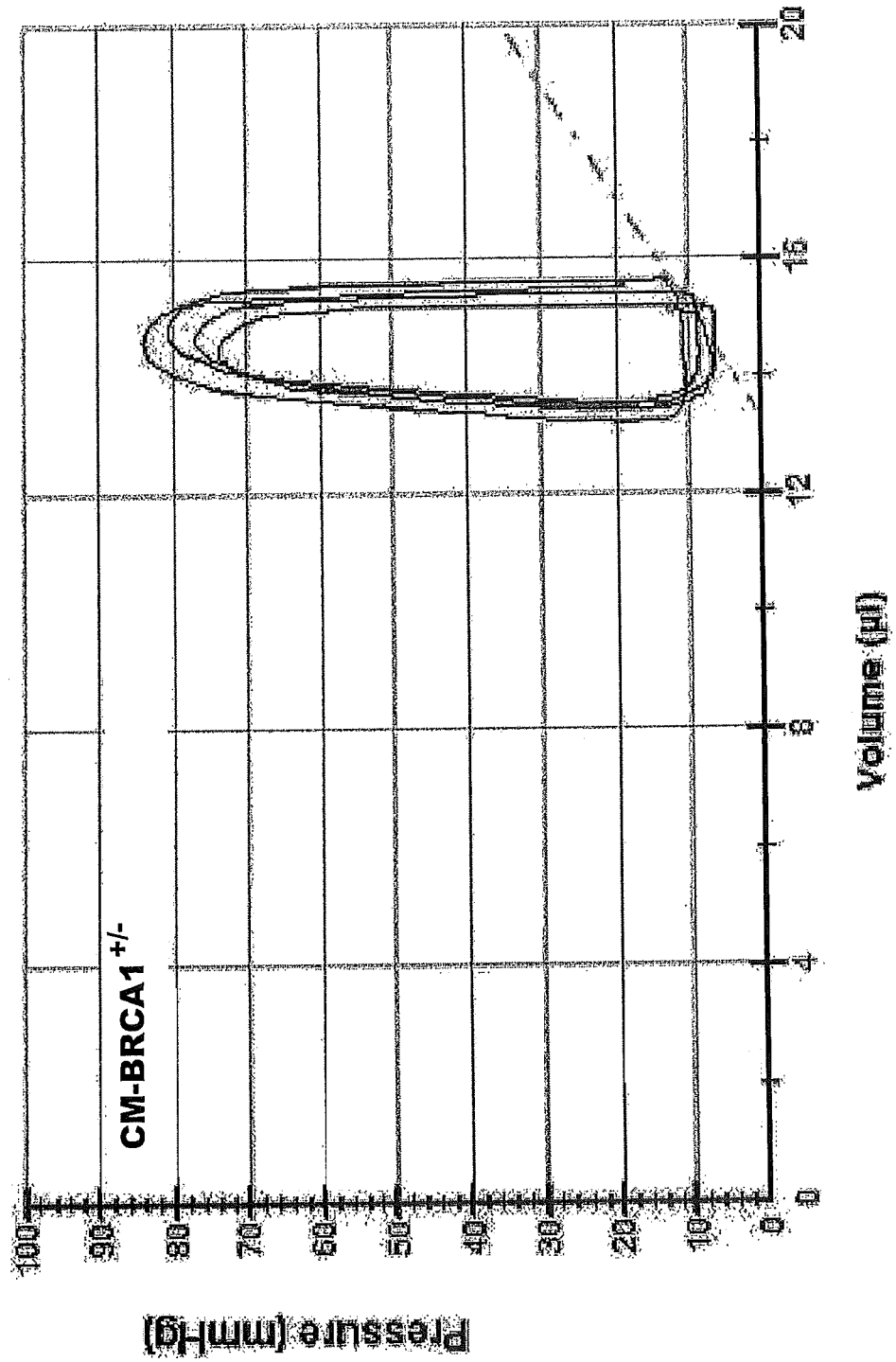
Figure 13E:
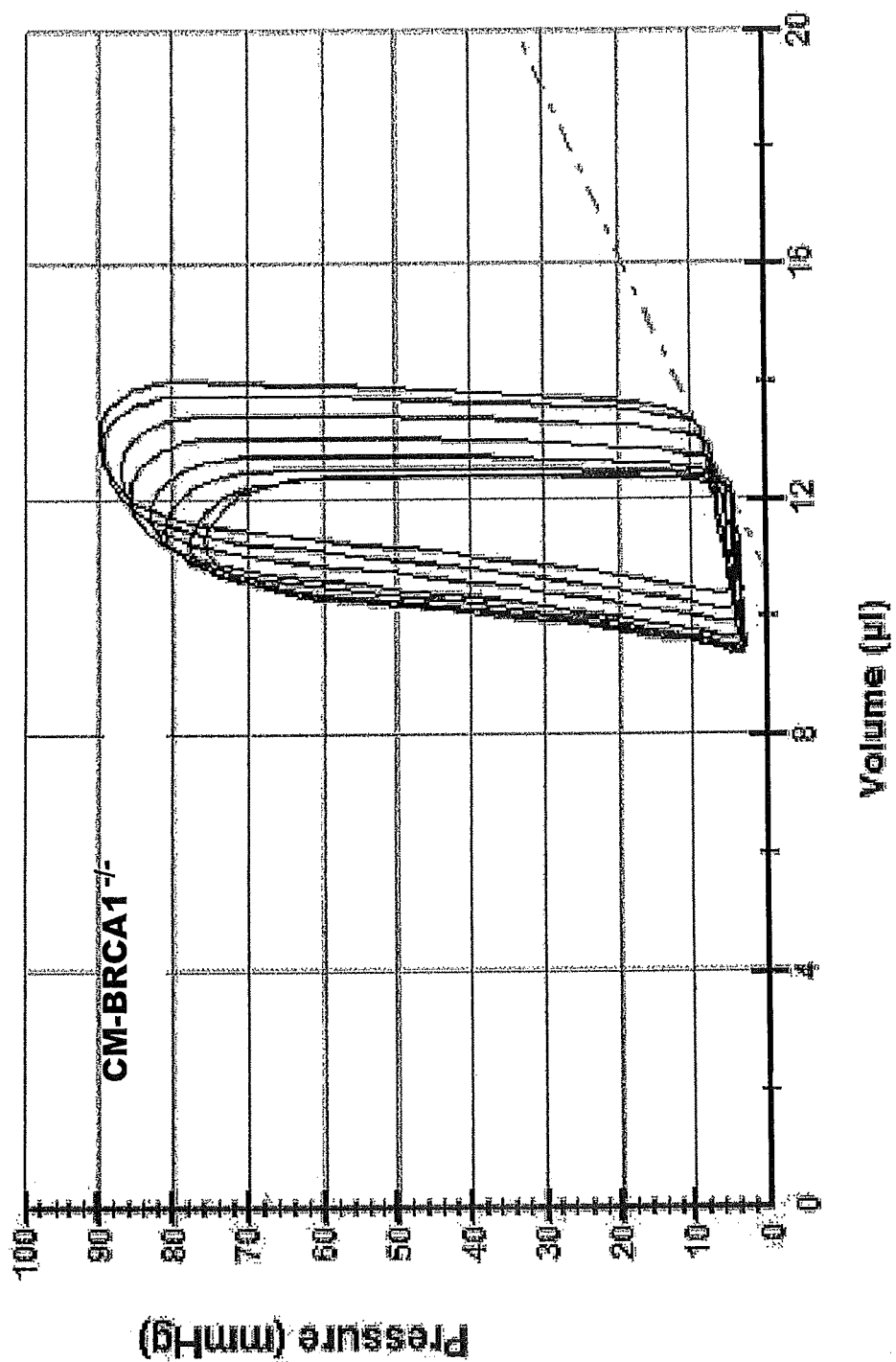
Figure 13F:
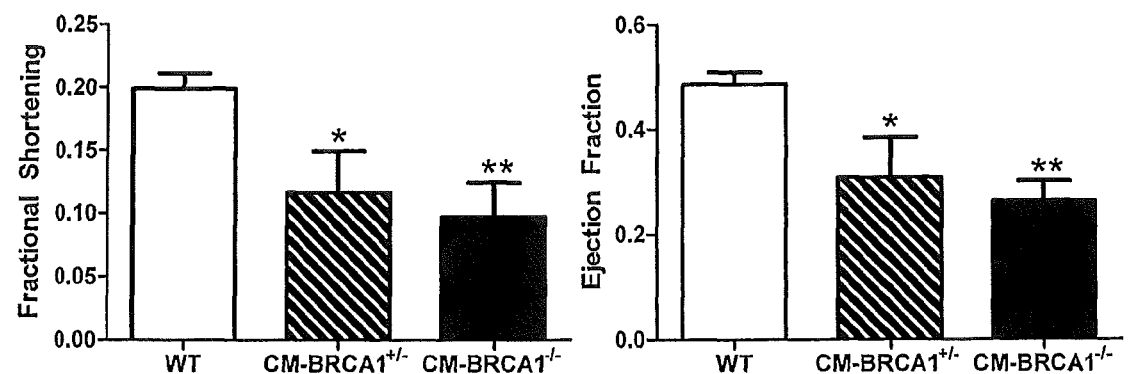
Figure 13G:
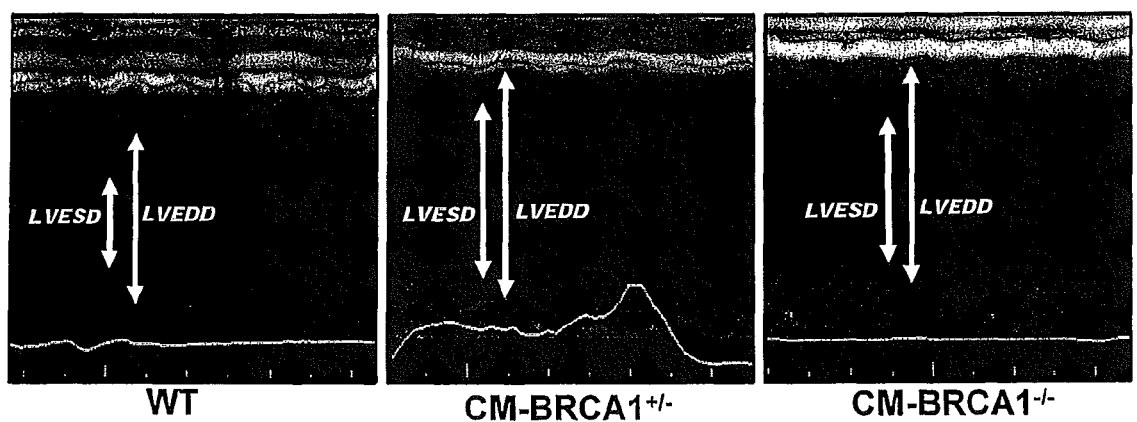

Cre-loxP technology was used to generate BRCA1-cardiac specific knockout mice. Specifically, mice wherein the expression of Cre recombinase is driven by cardiomyocyte specific α-Myosin Heavy Chain promoter (αMHC-Cre$^{tg/+}$) were crossed with mice whereby BRCA1 exon-11 was flanked by two loxP sites (BRCA1$^{fl/fl}$), thus giving rise to cardiomyocyte specific BRCA1 knockout (CM-BRCA1-KO) mice (αMHC-Cre$^{tg/+}$; BRCA1$^{fl/fl}$) (see FIGS. 12A and 12B). There was no basal adverse cardiac phenotype in these mice, as assessed by echocardiography, up to 12 weeks of age. Survival was similar at this age.

Figure 15A:
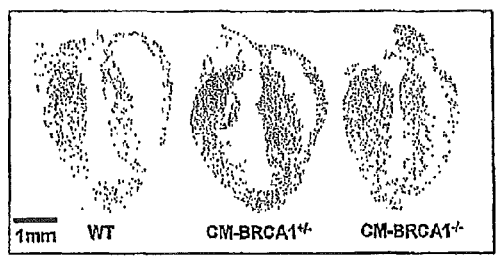
FIGS. 15A through 15D show the cardiac phenotype of mice with cardiomyocyte (CM)-specific BRCA1 deletion.
Figure 15B:
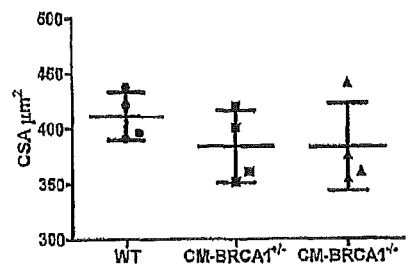
Figure 15C:
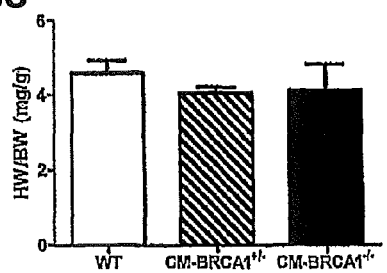
Figure 15D:
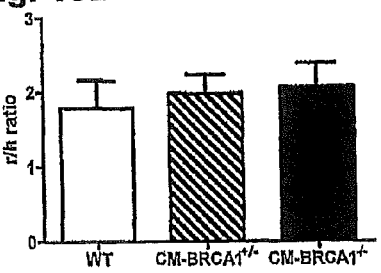

Mice with cardiomyocyte (CM)-specific BRCA1 deletion do not display any adverse cardiac phenotype as measured by H&E staining of heart sections from 10-12 week old male WT, CM-BRCA1$^{+/-}$ and CM-BRCA1$^{-/-}$ mice (FIG. 15A), comparison of cross sectional area (CSA) of septal cardiomyocytes (FIG. 15B), heart weight-to-body weight (HW/BW) ratios (FIG. 15C) and LV radius-to-septum thickness (r/h) (FIG. 15D).

Also see Tables 1 and 2.

TABLE 1

Baseline echocardiographic measurements performed on 10-12 week old male mice

| Cardiac Parameter | WT | CM-BRCA1$^{+/-}$ | CM-BRCA1$^{-/-}$ |
|---|---|---|---|
| Heart rate (bpm) | 445 ± 25 | 433 ± 65 | 410 ± 29 |
| LVEDD (cm) | 0.376 ± 0.051 | 0.350 ± 0.046 | 0.390 ± 0.039 |
| LVESD (cm) | 0.274 ± 0.050 | 0.239 ± 0.037 | 0.279 ± 0.041 |
| LVEDA (cm$^2$) | 0.116 ± 0.02 | 0.091 ± 0.008 | 0.118 ± 0.02 |
| LVESA (cm$^2$) | 0.061 ± 0.020 | 0.045 ± 0.017 | 0.058 ± 0.021 |
| Fractional Area Change | 0.48 ± 0.06 | 0.50 ± 0.17 | 0.50 ± 0.10 |
| LVEF | 0.61 ± 0.07 | 0.65 ± 0.20 | 0.62 ± 0.10 |
| LV Posterior Wall Thickness (cm) | 0.062 ± 0.004 | 0.060 ± 0.002 | 0.063 ± 0.004 |

LVEDD; left ventricular end-diastolic dimension
LVESD; left ventricular end-systolic dimension
LVEDA; left ventricular end-diastolic area
LVESA; left ventricular end-systolic area
LVEF; left ventricular ejection fraction

TABLE 2

Baseline Hemodynamic Assessment of Ventricular Performance in 10-12 week old male mice

| Cardiac Parameter | WT | CM-BRCA1$^{+/-}$ | CM-BRCA1$^{-/-}$ |
|---|---|---|---|
| LV End Systolic Volume (μl) | 6.2 ± 0.9 | 7.5 ± 0.8 | 8.3 ± 1.1 |
| LV End Diastolic Volume (μl) | 6.4 ± 2.1 | 8.5 ± 1.4 | 9.28 ± 1.1 |
| LV End Systolic Pressure (mmHG) | 99 ± 26 | 111 ± 6 | 95 ± 12 |
| LV End Diastolic Pressure (mmHG) | 5.4 ± 8.8 | 6.2 ± 4.7 | 12.6 ± 8.0 |
| Stroke Volume (μl) | 3.1 ± 0.13 | 3.7 ± 0.58 | 3.5 ± 0.9 |
| LV Ejection Fraction (%) | 41.9 ± 3.6 | 40.7 ± 7.7 | 35.5 ± 6.6 |
| Cardiac Output (μl/min) | 1760 ± 381 | 1506 ± 355 | 1599 ± 250 |
| Stroke Work (mmHg * μl) | 99 ± 21 | 112 ± 26 | 134 ± 50 |
| +dP/dt (mmHg/sec) | 6838 ± 293 | 5560 ± 929 | 6216 ± 908 |
| −dP/dt (mmHg/sec) | −6587 ± 2105 | −5079 ± 1113 | −5623 ± 585 |

However, mice with cardiomyocyte (CM)-specific BRCA1 deletion displayed adverse cardiac remodeling and poor ventricular function following myocardial infarction (MI; see FIGS. 13A through 13G). Specifically, post-MI left ventricular infarct size of hearts from CM-BRCA1$^{+/-}$ and CM-BRCA1$^{-/-}$ was greater than those from WT mice (see FIG. 13A). CSA of septal cardiomyocytes 4 weeks after MI induction were smaller in CM-BRCA1 and CM-BRCA1$^{-/-}$ mice relative to their WT littermates (see FIG. 13B). CM-BRCA1$^{+/-}$ and CM-BRCA1$^{-/-}$ mice also exhibited lower HW/BW ratios (see FIG. 13C) and greater LV radius-to-septum thickness (r/h) ratios (see FIG. 13D) relative to WT mice. LV compliance, as determined by the slope of the end-diastolic-pressure-volume relationship (EDPVR), was lower in CM-BRCA1$^{+/-}$ and CM-BRCA1$^{-/-}$ mice compared to WT mice 4 weeks post-MI (see FIG. 13E). LV performance, in particular ejection fraction and fractional shortening, 4 weeks post-MI induction, as measured by 2D-echocardiography, was lower in CM-BRCA1$^{+/-}$ and CM-BRCA1$^{-/-}$ mice relative to WT mice (see FIG. 13F). M-mode representative photographs obtained after echocardiography from infarcted mice also showed a marked increase in LV dilation, indicating poor LV function in CM-BRCA1$^{+/-}$ and CM-BRCA1$^{-/-}$ compared to WT mice (see FIG. 13G). Also see Table 3.

TABLE 3

Hemodynamic Assessment of Ventricular Performance in anesthetize mice after 4 weeks of MI using Millar catheter

| Cardiac Parameter | WT | CM-BRCA1$^{+/-}$ | CM-BRCA1$^{-/-}$ |
|---|---|---|---|
| LV End Systolic Volume (μl) | 6.51 ± 2.11 | 14.73 ± 6.1* | 11.53 ± 3.8* |
| LV End Diastolic Volume (μl) | 7.98 ± 4.2 | 16.23 ± 5.56* | 13.32 ± 3.5* |
| LV End Systolic Pressure (mmHG) | 104 ± 14 | 83 ± 15* | 89 ± 6* |
| LV End Diastolic Pressure (mmHG) | 21 ± 8 | 19 ± 14 | 22 ± 5 |
| Stroke Volume (μl) | 4.75 ± 1.4 | 2.3 ± 1.3* | 2.97 ± 0.6* |
| LV Ejection Fraction (%) | 46.3 ± 4.0 | 21.0 ± 11.4** | 23.16 ± 4.9** |
| Cardiac Output (μl/min) | 2169 ± 819 | 1105 ± 577* | 1497 ± 330 |
| Stroke Work (mmHg * μl) | 302 ± 111 | 138 ± 90* | 155 ± 57* |
| +dP/dt (mmHg/sec) | 6820 ± 1226 | 4173 ± 1021** | 4890 ± 813* |
| −dP/dt (mmHg/sec) | −5747 ± 1183 | −3553 ± 833* | −4240 ± 1035* |

**p < 0.01 Vs WT,
*p < 0.05 Vs WT.
(n = 5-6/group).

LV hemodynamics were measured with a 1.4 F micromanometer conductance catheter inserted in the LV cavity via the right carotid artery. The conductance volume is expressed in relative volume units (RVU). The ejection fraction (EF) was computed via the formula [(stroke volume/volume at dp/dtmax)×100] using RVU.

Figure 14A:
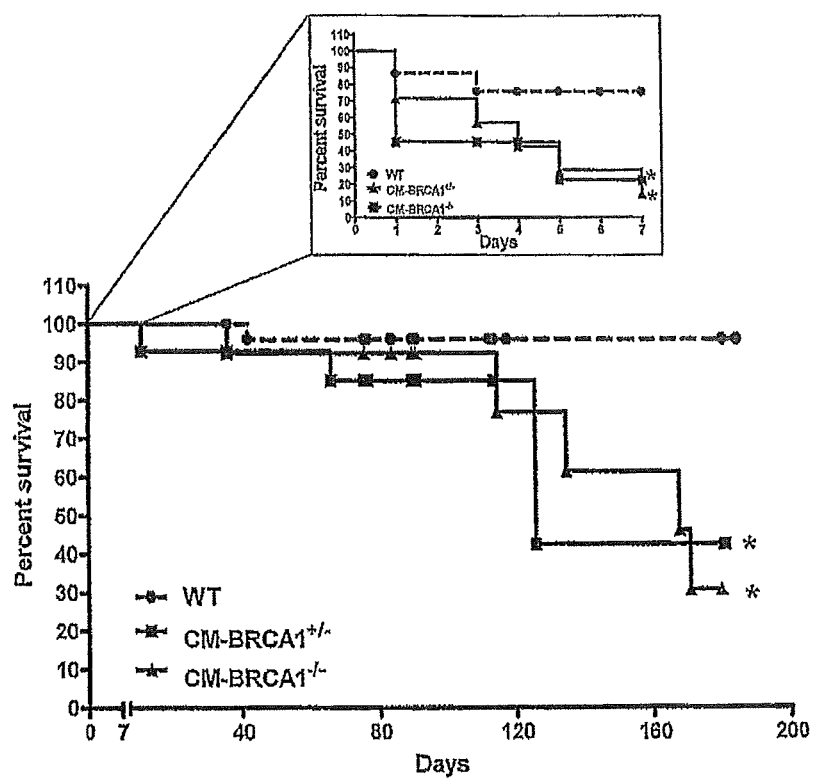
FIGS. 14A and 14B show susceptibility of mice with cardiomyocyte (CM)-specific BRCA1 deletion to mortality related to myocardial infarction (MI).
Figure 14B:
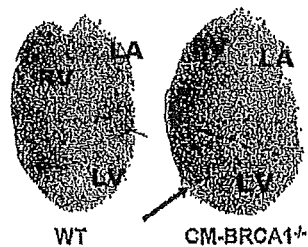

Mice with cardiomyocyte (CM)-specific BRCA1 deletion were also found to exhibit increased susceptibility to mortality related to myocardial infarction (MI). See Kaplan curves of FIG. 14A. In these experiments, the left anterior descending coronary arteries were ligated to induce MI in 10-12 week old male WT (n=39), CM-BRCA1$^{+/-}$ (n=19) and CM-BRCA1$^{-/-}$ (n=18) mice. Representative photographs of unruptured ventricles from WT mice and ruptured left ventricle (arrow) from CM-BRCA1$^{-/-}$ mice 2 days after coronary ligation are shown in FIG. 14B.

Figure 16A:
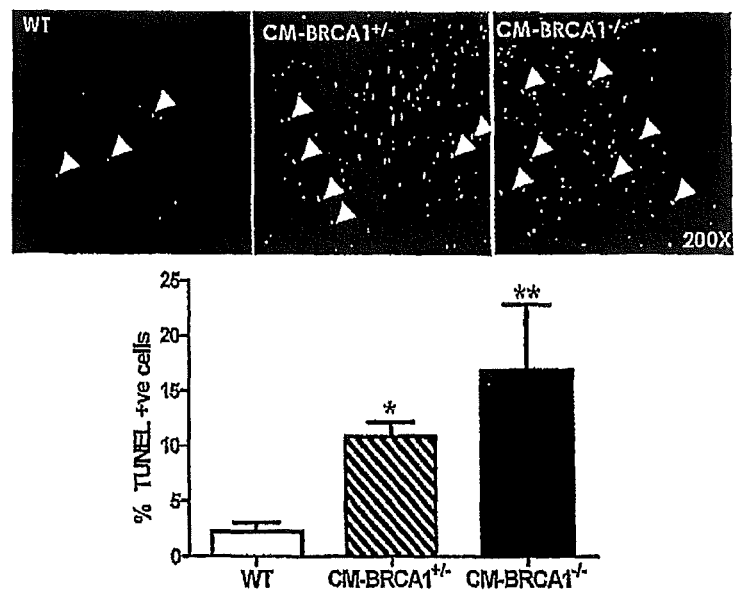
FIGS. 16A through 16C show results of cardiomyocyte (CM)-specific BRCA1 deletion on pro-apoptotic signaling in the heart after MI.
Figure 16B:
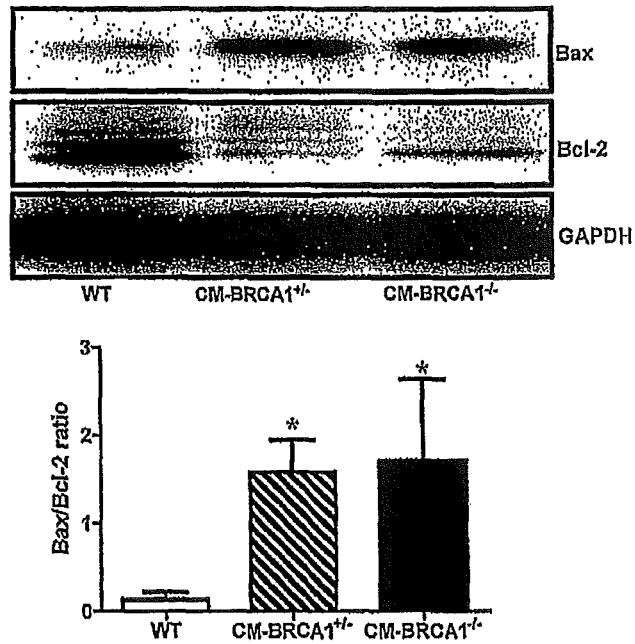
Figure 16C:
Figure 17A:
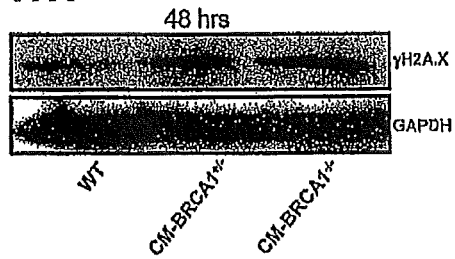
FIGS. 17A though D show repair of MI-induced double-stranded DNA breaks (DSBs) in mice with cardiomyocyte (CM)-specific BRCA1 deletion. Total whole heart protein was extracted 48 hours (FIGS. 17A and 17C) and 72 hours (FIGS. 17B and 17D) after MI induction to determine the levels of the DSB marker $\gamma$ H2A.X. n=3; *$p<0.05$ vs WT, **$p<0.01$ vs. WT.
Figure 17B:
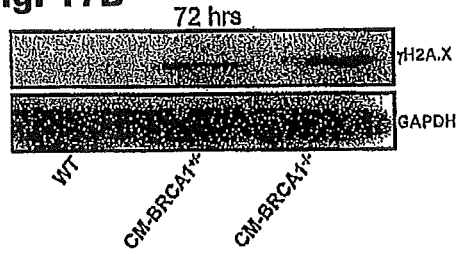
Figure 17C:
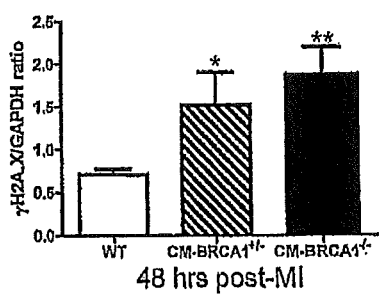
Figure 17D:
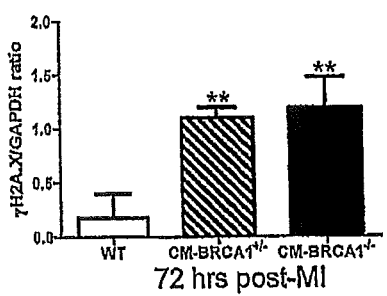

Cardiomyocyte (CM)-specific BRCA1 deletion was shown to activate pro-apoptotic signaling in the heart after MI (see FIGS. 16A through 16C) as indicated by western blotting.

Cardiomyocyte (CM)-specific BRCA1 deletion was found to impair repair of MI-induced double-stranded DNA breaks (DSBs (FIGS. 17A through D) as indicated by western blotting.

Figure 18:
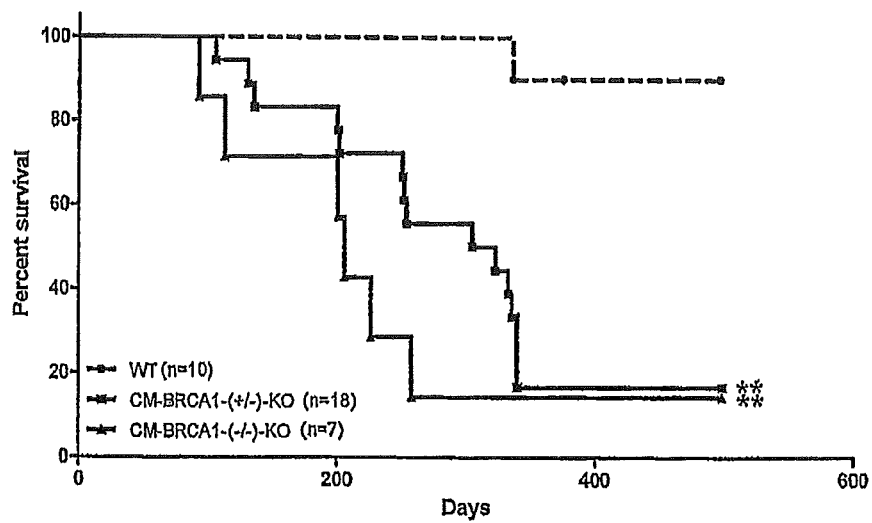
FIG. 18 shows a Kaplan-Meier survival curve of male and female WT littermates as well as cardiomyocyte-specific BRCA1 homozygous (CM-BRCA1$^{-/-}$) and heterozygous (CM-BRCA1$^{+/-}$) knockout mice. Mice homozygous for a floxed BRCA1 allele (BRCA1$^{fl/fl}$) were crossed with heterozygous mice expressing Cre recombinase under the control of the $\alpha$-myosin heavy chain ($\alpha$MHC-Cre$^{tg/+}$) promoter. Mice demonstrating postnatal inactivation of BRCA1 (−/−; $\alpha$MHC-Cre$^{tg/+}$; BRCA1$^{fl/fl}$ and +/−; $\alpha$MHC-Cre$^{tg/+}$; BRCA1$^{fl/+}$) were identified as CM-BRCA1$^{-/-}$ mice while littermates not expressing the Cre transgene were used as WT controls (**$p<0.01$).

Male and female WT littermates as well as cardiomyocyte-specific BRCA1 heterozygous (CM-BRCA1$^{+/-}$) mice exhibited increased survival as compared to homozygous (CM-BRCA1$^{-/-}$) knockout mice (See FIG. 18).

Figure 19A:
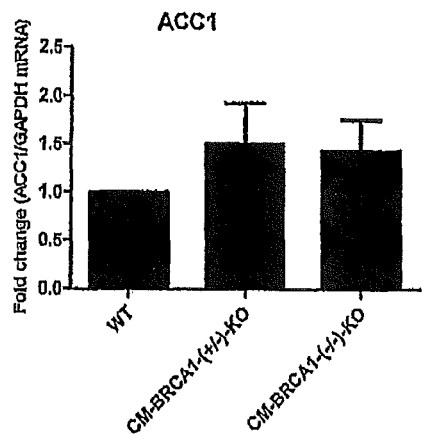
FIGS. 19A through 19D show acetyl-CoA carboxylase 2 (ACC2) and malonyl-CoA decarboxylase (MCD) expression in the hearts of WT, CM-BRCA1$^{+/-}$ and CM-BRCA1$^{-/-}$ mice. Total RNA and protein were extracted from the hearts of 32-week old female mice (n=3 per group) to determine levels of ACC1 transcripts (FIG. 19A), ACC2 transcripts (FIG. 19B), total ACC (ACC1+ACC2) and phospho(Ser 79)-ACC protein levels (FIG. 19C) and MCD transcripts (FIG. 19D). Positive values indicate fold increases and negative values indicate fold decreases relative to the control WT group. *$p<0.05$, **$p<0.01$ vs. WT.
Figure 19B:
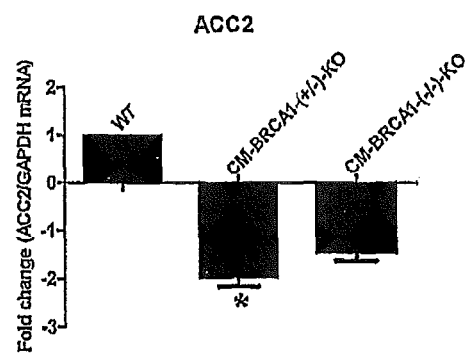
Figure 19C:
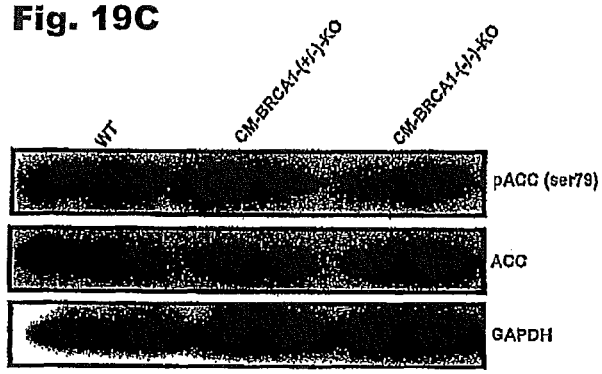
Figure 19D:
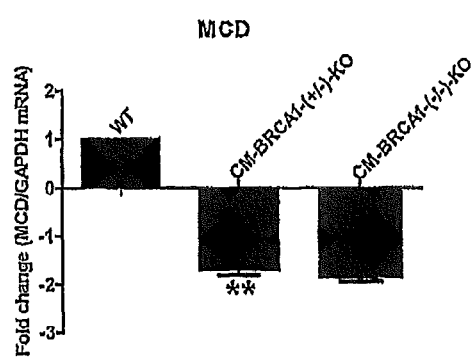

Cardiomyocyte (CM)-specific BRCA1 deletion reduced acetyl-CoA carboxylase 2 (ACC2; FIGS. 19B and 19C)) and malonyl-CoA decarboxylase (MCD; FIG. 19D) expression in the heart. Panels A, B and D were derived from real-time PCR; panel C was measured by western blotting.

Figure 20A:
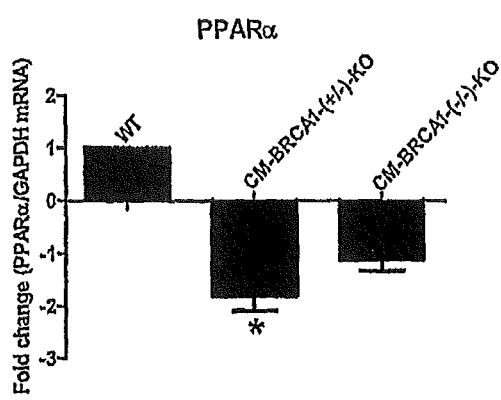
FIGS. 20A through 20C show PPAR$\alpha$, PPAR$\beta$ and PPAR$\gamma$ levels in the hearts of WT, CM-BRCA1$^{+/-}$ and CM-BRCA1$^{-/-}$ mice. Total RNA was extracted from the hearts of 32-week old female mice (n=3 per group) to determine transcript levels of PPAR$\alpha$ (FIG. 20A), PPAR$\beta$ (FIG. 20B) and PPAR$\gamma$ (FIG. 20C). Positive values indicate fold increases and negative values indicate fold decreases relative to the control WT group. *$p<0.05$, **$p<0.01$ vs. WT.
Figure 20B:
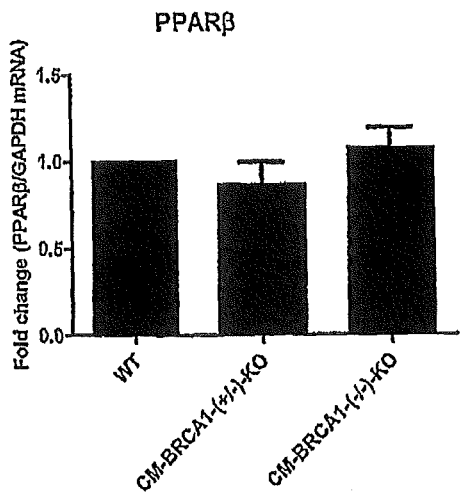
Figure 20C:
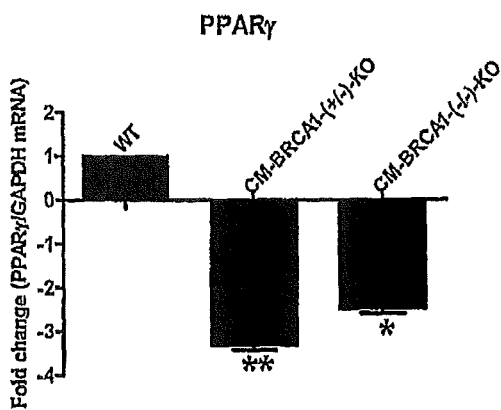
Figure 21A:
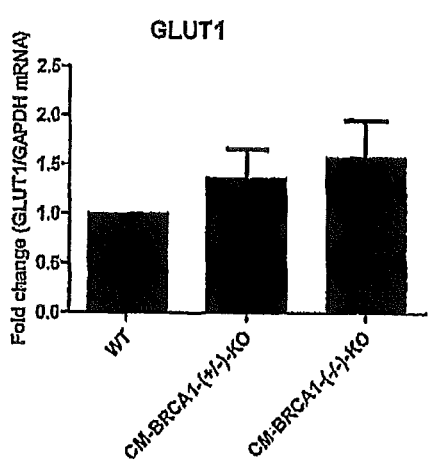
FIGS. 21A through 21D show downstream PPAR target levels in the hearts of WT, CM-BRCA1$^{+/-}$ and CM-BRCA1$^{-/-}$ mice. Total RNA was extracted from the hearts of 32-week old female mice (n=3 per group) to determine transcript levels of GLUT1 (FIG. 21A), GLUT4 (FIG. 21B), CD36 (FIG. 21C) and carnitine palmitoyl transferase 1a (CPT1.
Figure 21B:
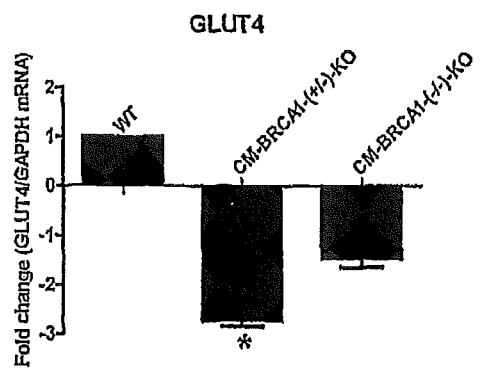
Figure 21C:
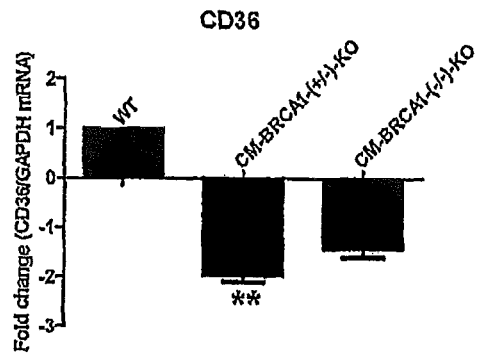
Figure 21D:
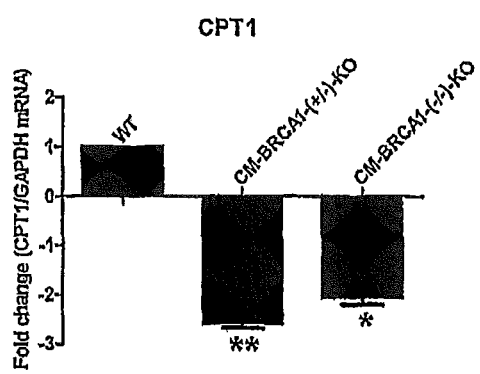

Cardiomyocyte (CM)-specific BRCA1 deletion also reduced PPARα (FIG. 20A) and PPARγ (FIG. 20C) levels in the heart (as measured by real-time PCR), as well as activation of downstream PPAR targets, GLUT4 (FIG. 21B), CD36 (FIG. 21C) and carnitine palmitoyl transferase 1a (CPT1a; FIG. 21D)) in the heart, as measured by real-time PCR.

Figure 22:
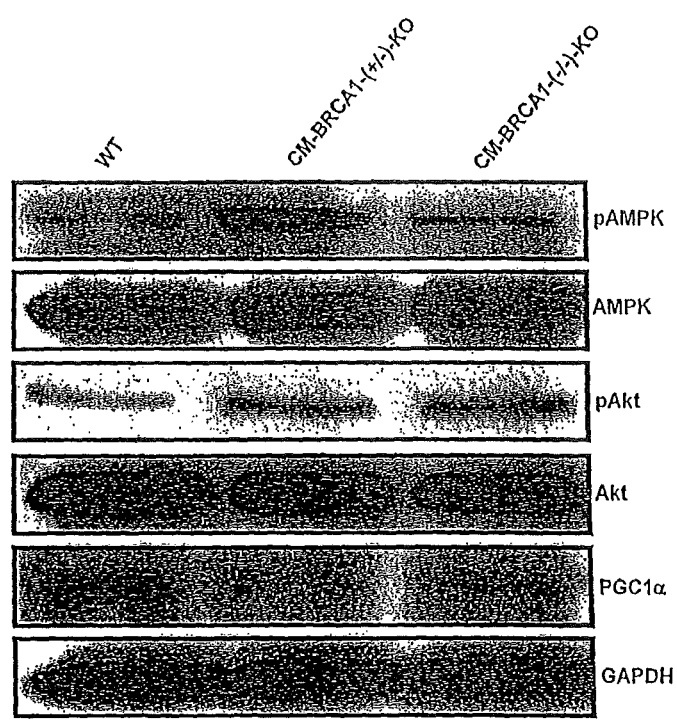
FIG. 22 shows AMPK and Akt pathways as well as PGC1$\alpha$ levels in the hearts of WT, CM-BRCA1$^{+/-}$ and CM-BRCA1$^{-/-}$ mice. Total protein was extracted from the hearts of 32-week old female mice (n=3 per group) to determine levels of total and phospho-Akt, total and phospho-AMPK, and PGC1$\alpha$. GAPDH was used as a loading control.

Further, cardiomyocyte (CM)-specific BRCA1 deletion activated AMPK and Akt pathways while reducing PGC1α levels in the heart (FIG. 22) as measured by western blotting.

The inventors have now found that BRCA1 can also be used to limit inflammation-induced endothelial cell apoptosis and to restore endothelial function.

Figure 23A:
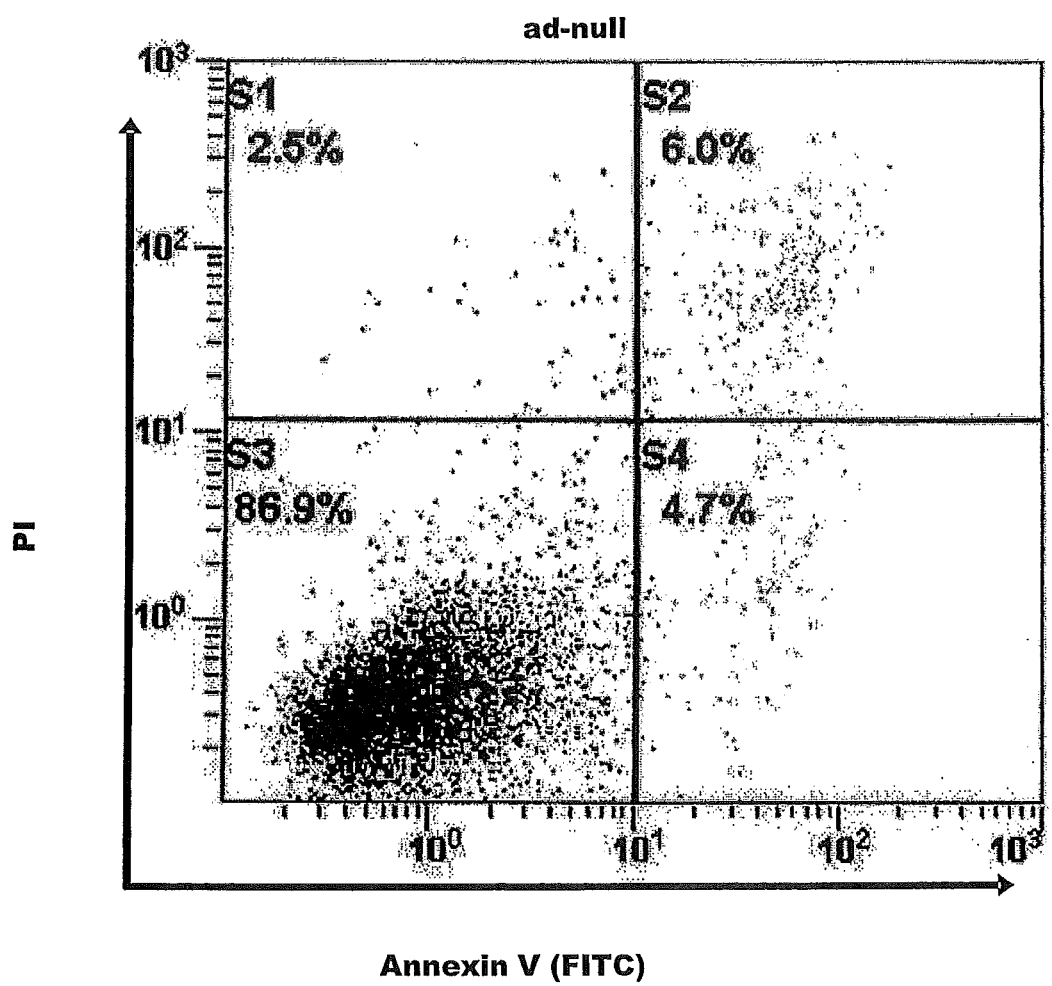
FIGS. 23A through 23E shows results from experiments demonstrating BRCA1 protects endothelial cells against apoptosis.
Figure 23A:
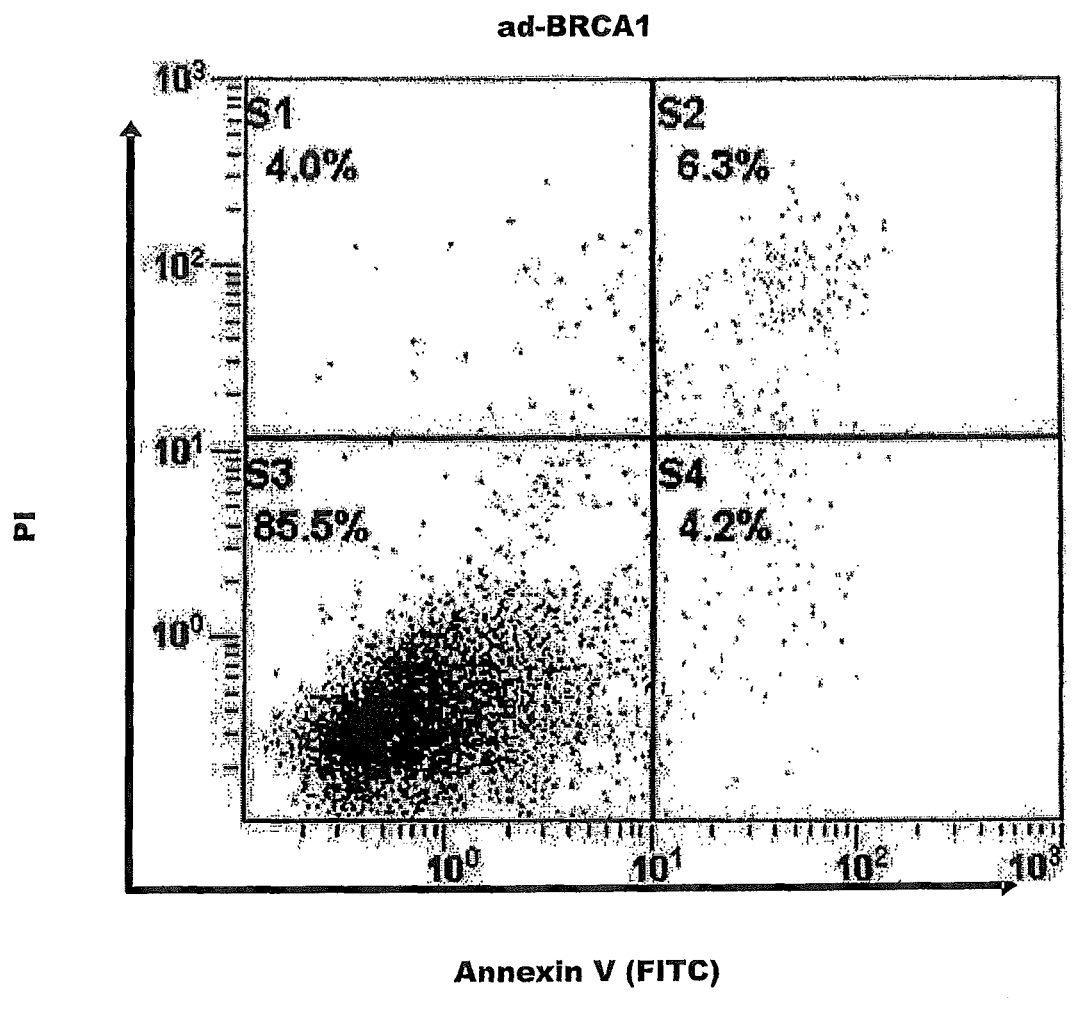
Figure 23A:
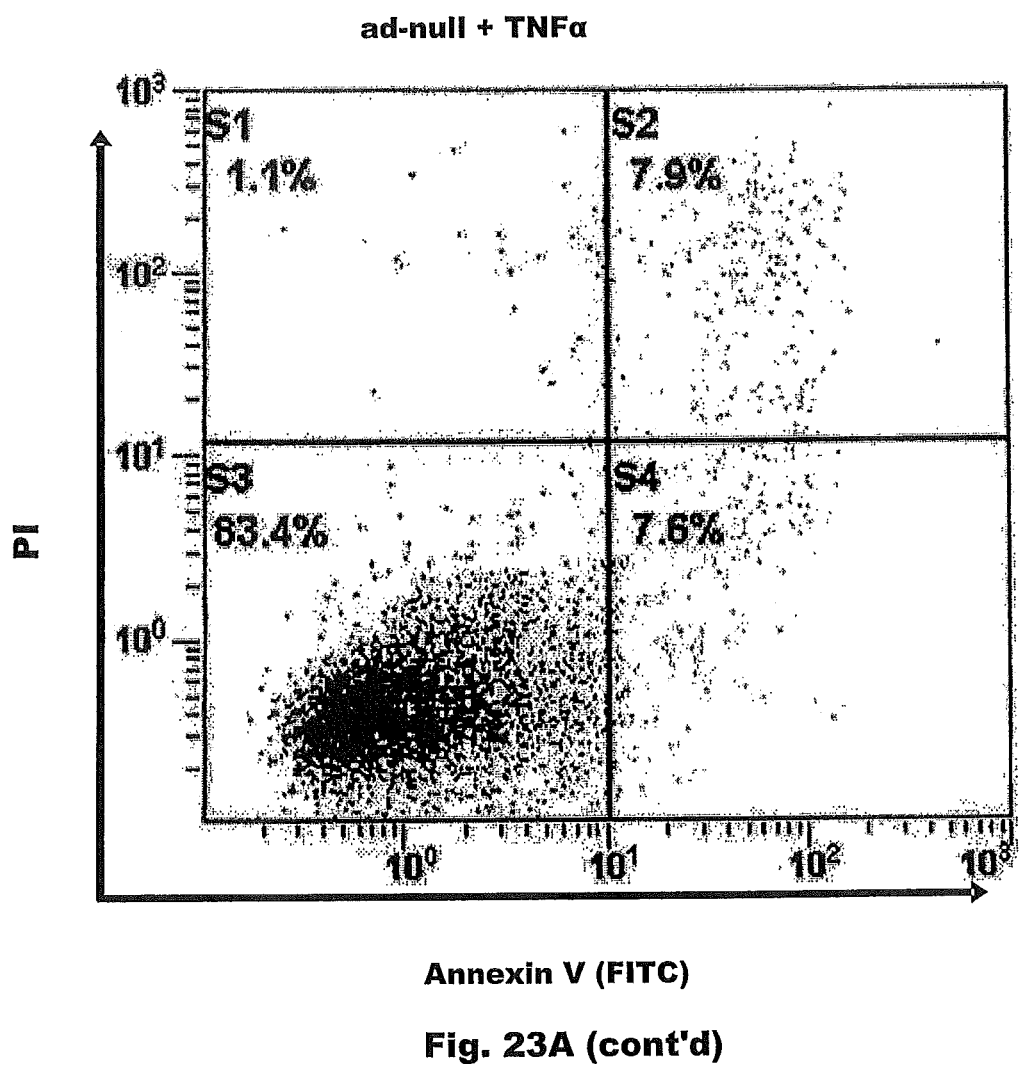
Figure 23A:
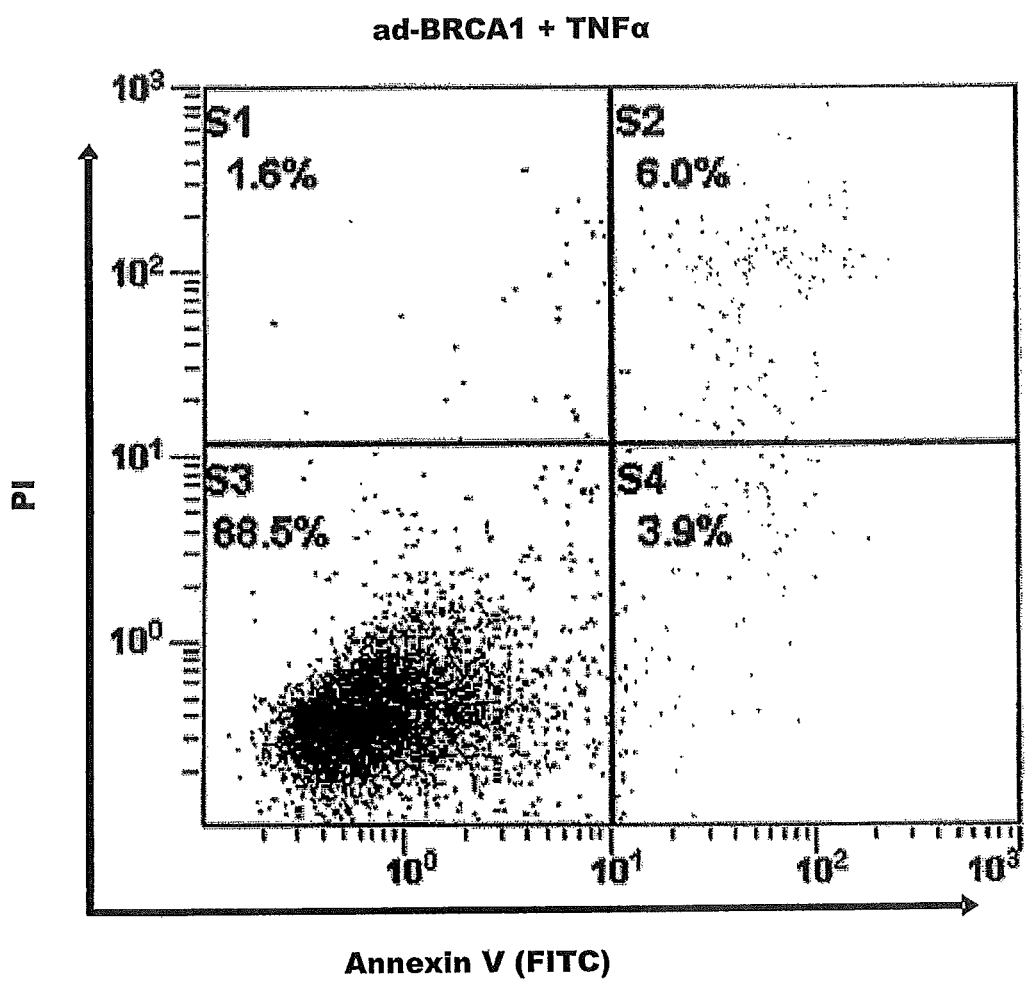
Figure 23A:
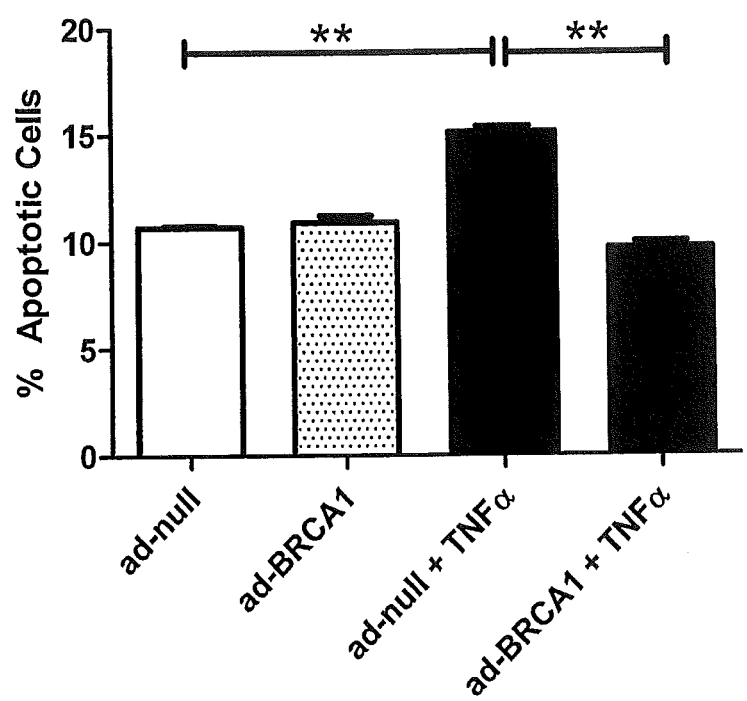
Figure 23B:
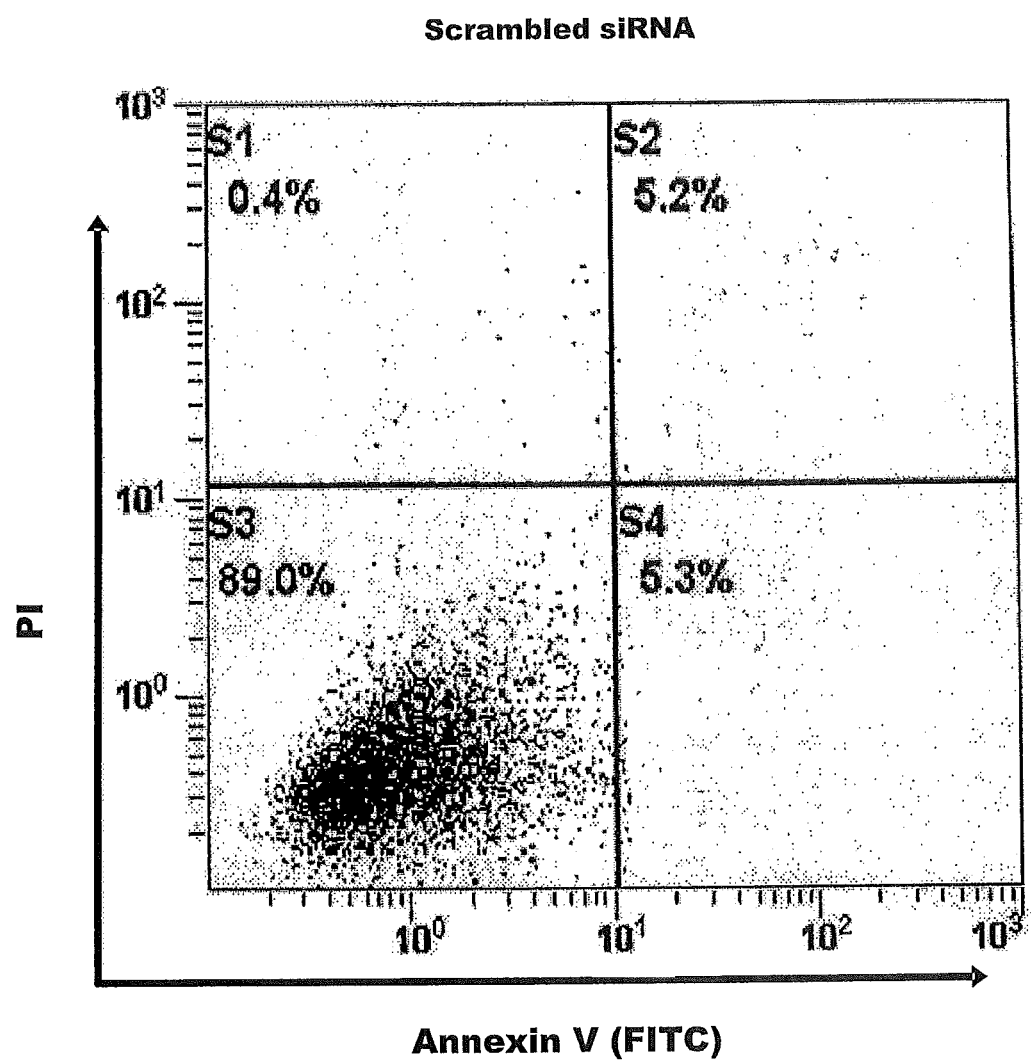
Figure 23B:
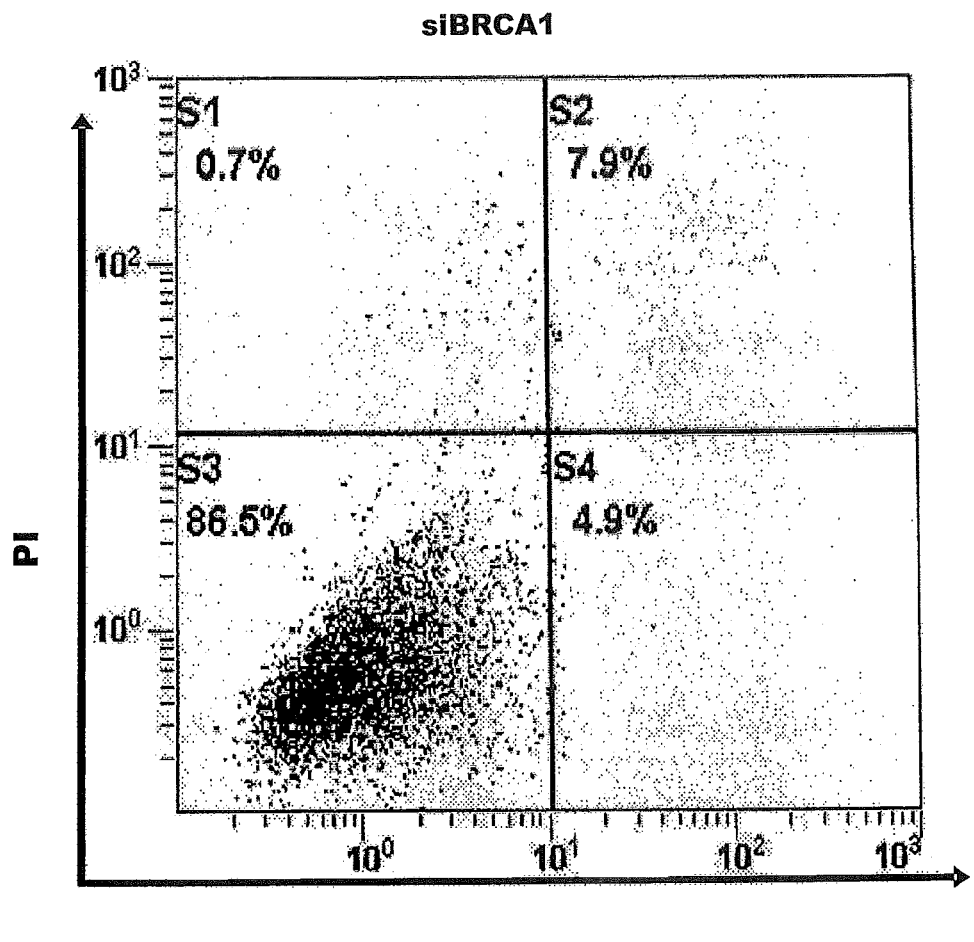
Figure 23B:
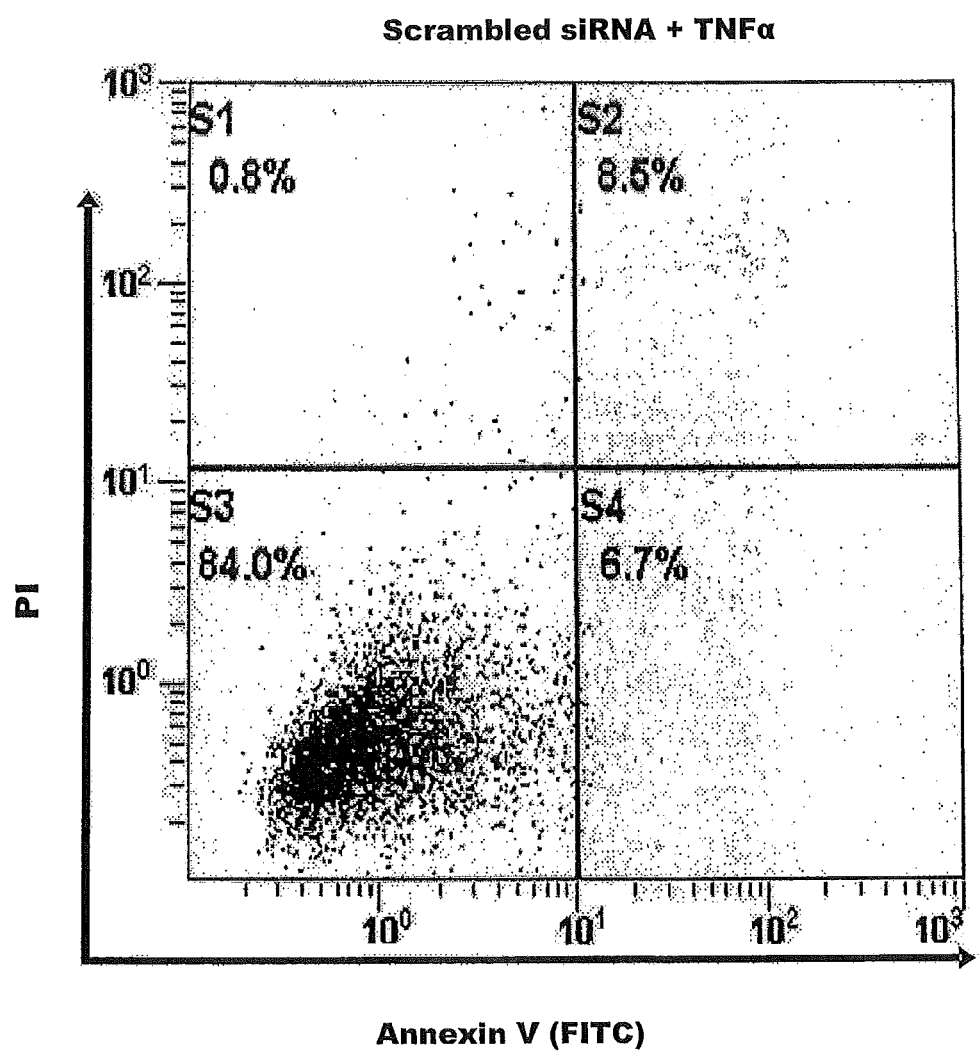
Figure 23B:
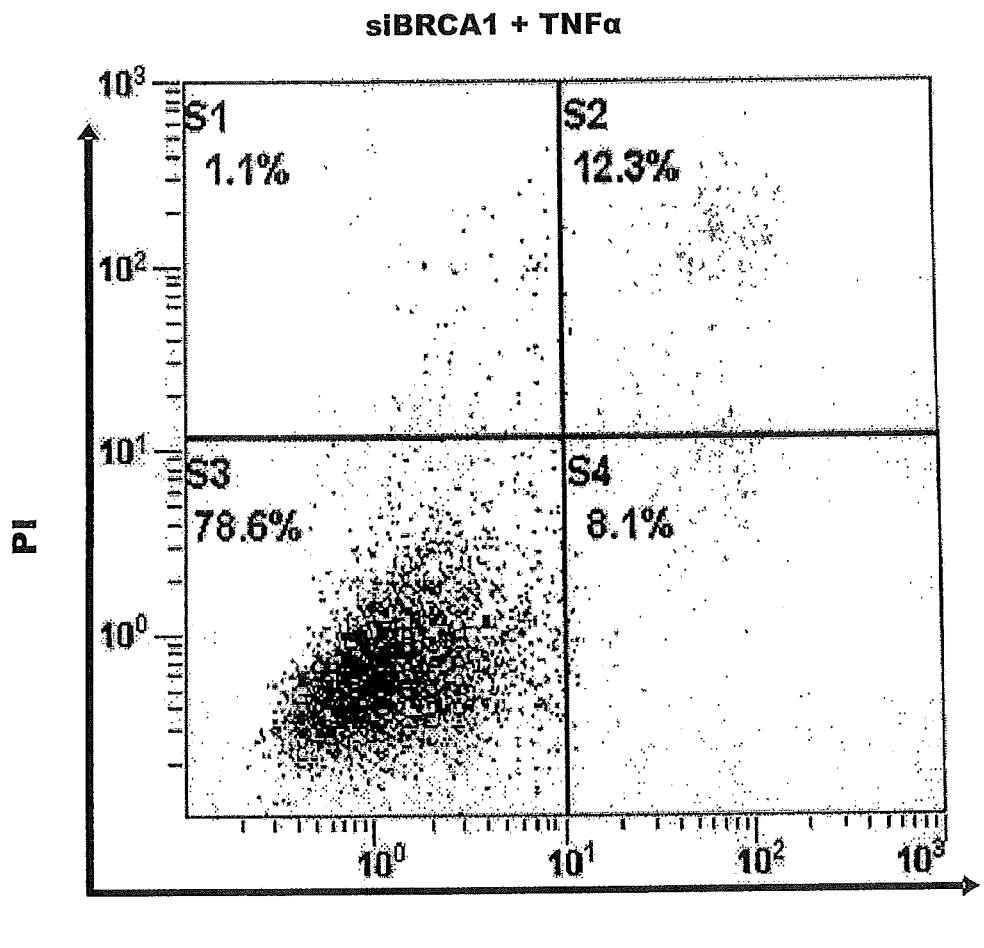
Figure 23B:
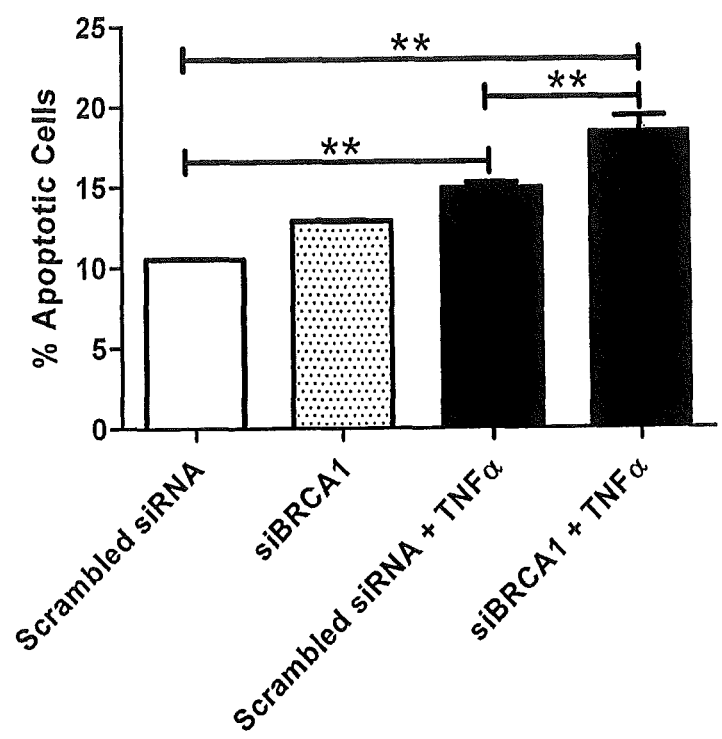
Figure 23C:
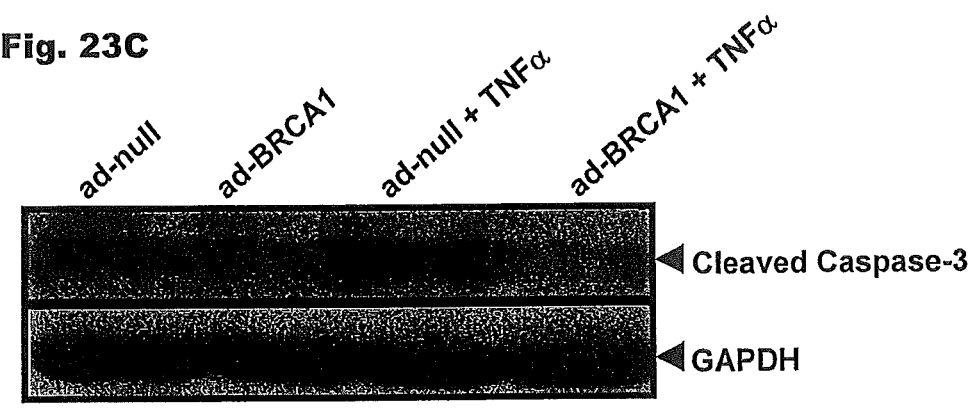
Figure 23D:
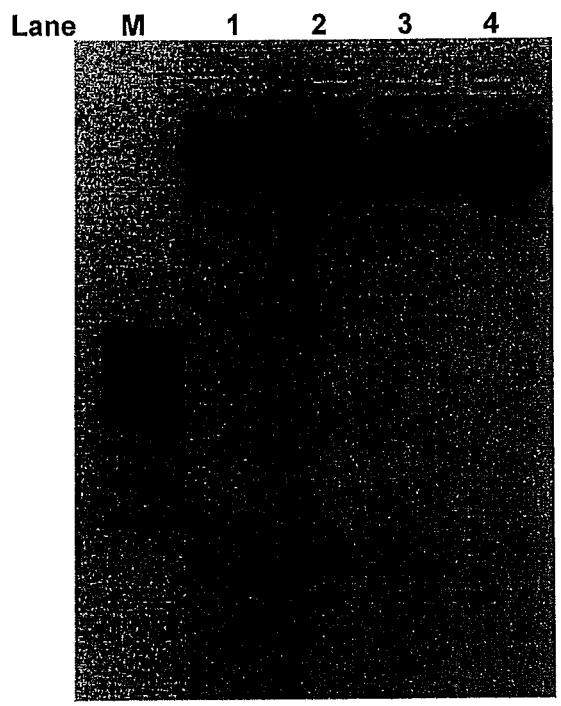
Figure 23E:
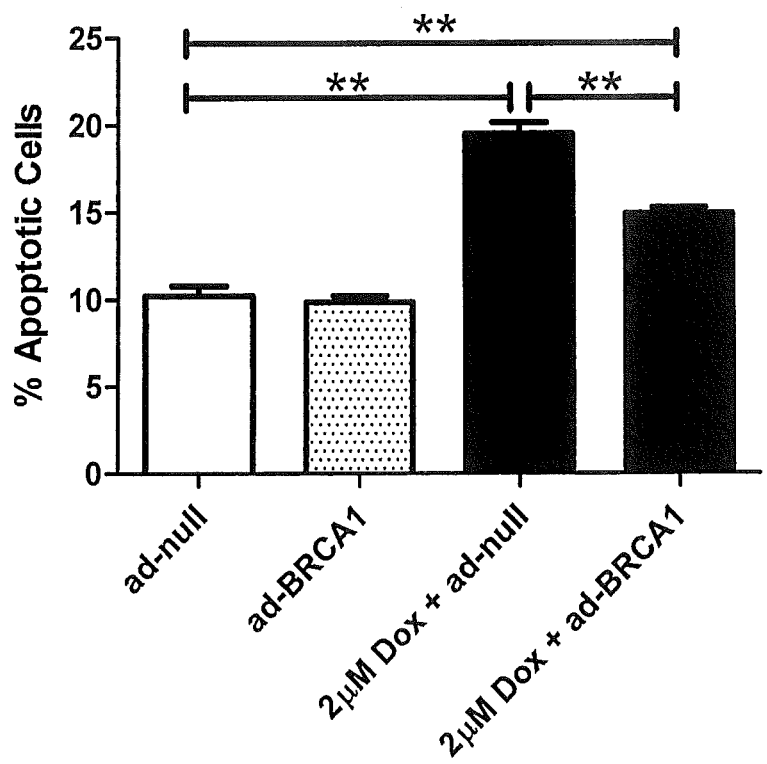

As shown in FIG. 23A, TNFα evoked significant apoptosis in ad-null infected HUVECs (p<0.01), an effect that was absent in similarly treated BRCA1-overexpressing HUVECs. In contrast, a greater number of apoptotic events were observed in TNFα-treated BRCA1-silenced HUVECs than in TNFα-treated HUVECs that had been previously incubated with scrambled siRNA (p<0.01; FIG. 23B). BRCA1-overexpression also dampened TNFα-associated increase in cleaved caspase-3 protein levels (see FIG. 23C) as well as TNFα-induced DNA fragmentation (see FIG. 23D). While apoptosis was prevalent in doxorubicin-treated ad-null infected HUVECs, HUVECs transfected with ad-BRCA1 appeared to be protected against doxorubicin-induced apoptosis (p<0.01; FIG. 23E).

Figure 24A:
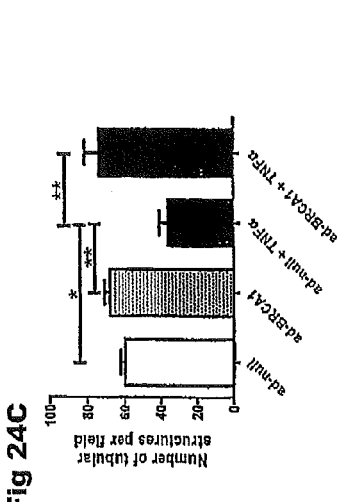
FIGS. 24A through 24I show results from experiments demonstrating adenoviral BRCA1 restores the endothelial function following detrimental TNFα treatment.
Figure 24B:
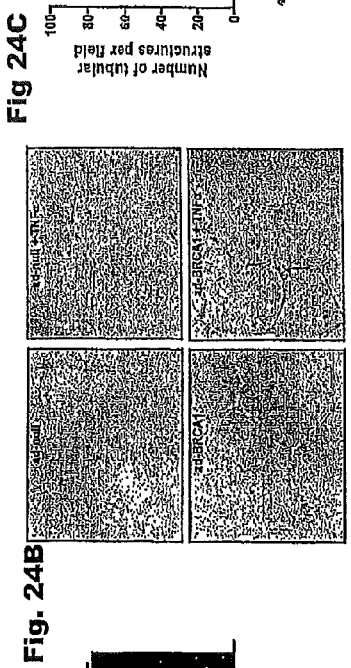
Figure 24C:
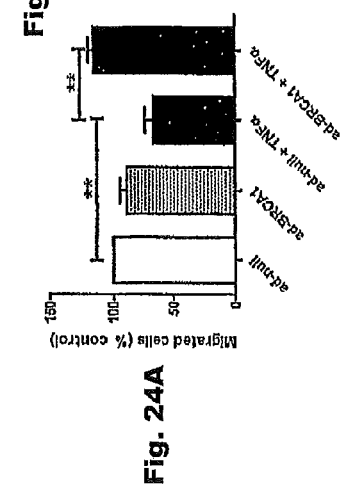
Figure 24D:
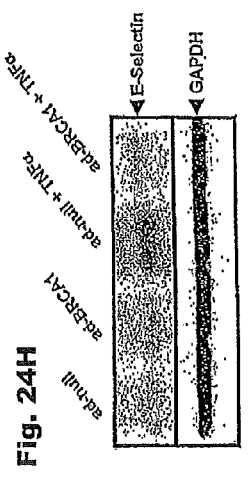
Figure 24E:
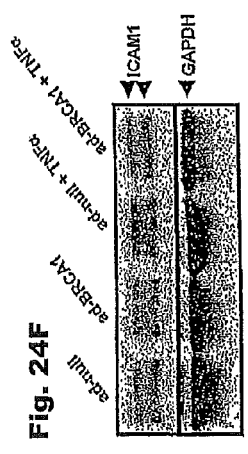
Figure 24F:
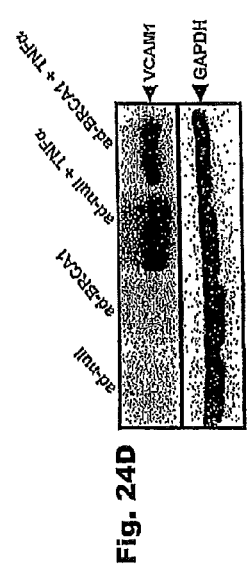
Figure 24G:
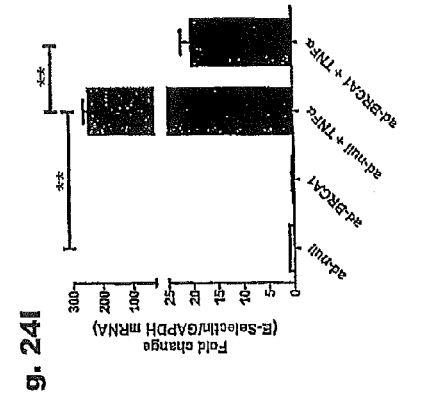
Figure 24H:
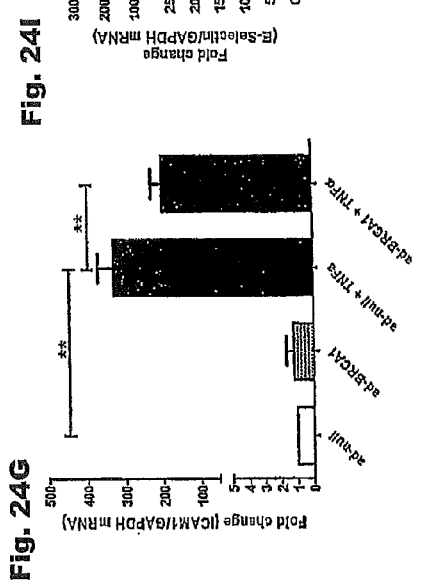
Figure 24I:
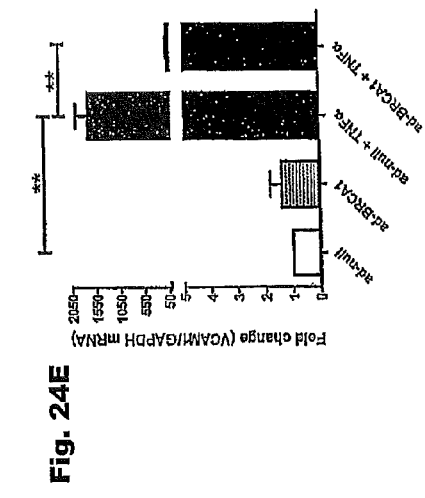

BRCA1 was also demonstrated to restore endothelial function. TNFα significantly hampered the migratory capacity of HUVECs (p<0.01), an effect that could be restored in BRCA1 over-expressing HUVECs (p<0.01) (see FIG. 24A). As shown in FIGS. 24B and 24C, the capacity of HUVECs to form vessel-like tubular structures was reduced in the presence of TNFα (p<0.05). There was no appreciable difference in tube formation ability between the ad-null treated and ad-BRCA1 treated groups for up to 18 hours after treatment. In BRCA1-overexpressing HUVECs, generation of tube-like structures was unaffected by TNFα as early as 5 hours post-treatment (see FIGS. 24B and 24C). At the transcript level, ad-null treated HUVEC VCAM1, ICAM1 and E-selectin expression in ad-null treated HUVECs were respectively upregulated 1500 times, 400 times and 200 times (p<0.01) following TNFα treatment (see FIGS. 24E, 24G and 24I). These TNFα-elicited increases were significantly dampened in BRCA1-overexpressing HUVECs (p<0.01; FIGS. 24E, 24G and 24I). Protein levels of VCAM1, ICAM1 and E-selectin, as measured by western blotting, followed a similar response pattern to TNFα stimulation and ad-BRCA1 transfection (see FIGS. 24D, 24F and 24H).

Figure 25A:
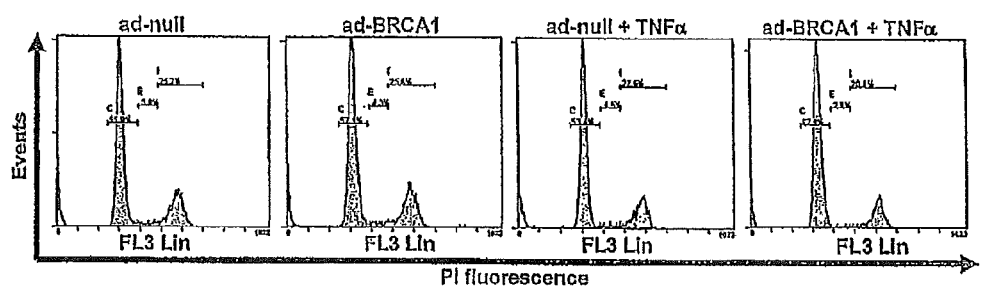
FIGS. 25A and 25B show results from experiments demonstrating BRCA1 overexpression leads to p21-mediated but p53 independent growth arrest in response to TNFα.
Figure 25B:
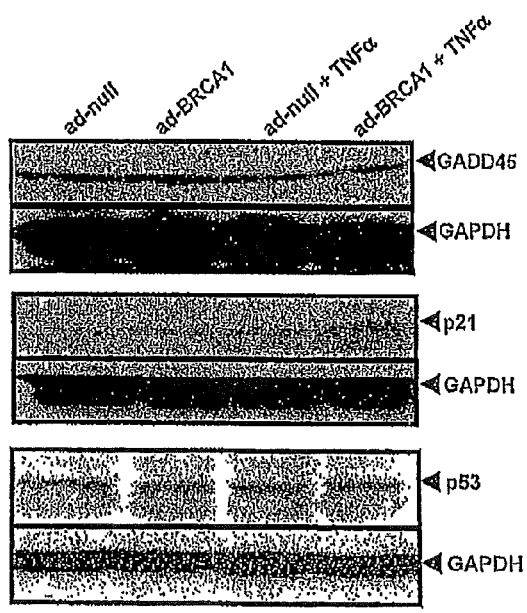

BRCA1 was also demonstrated to promote growth arrest. BRCA1 has previously been shown to promote reversible growth arrest under stress in order to allow repair via upregulation of GADD45 or p21, in both a p53-dependent or -independent manner (Murray et al. Biochem Soc Trans. 2007 November; 35(Pt 5):1342-6; Gilmore et al. Biochem Soc Trans. 2003 February; 31(Pt 1):257-62). In contrast, TNFα signaling is associated with an increase in oxidative stress or reactive oxygen species (ROS) production which can in turn induce DNA damage. In experiments set forth herein, 12 hours of TNFα treatment resulted in significantly more BRCA1-overexpressing cells entering the growth arrest phase ($G_0/G_1$) compared to similarly stressed ad-null treated HUVECs (p<0.01; FIG. 25A). Western blotting showed that TNFα had no influence on the protein levels of p53 and GADD45 but did significantly elevate p21 protein levels in the presence and absence of BRCA1 overexpression (see FIG. 25B). These results indicate that BRCA1 induces growth arrest in HUVECs treated with TNFα in a p21-dependent but p53-independent manner.

Figure 26:
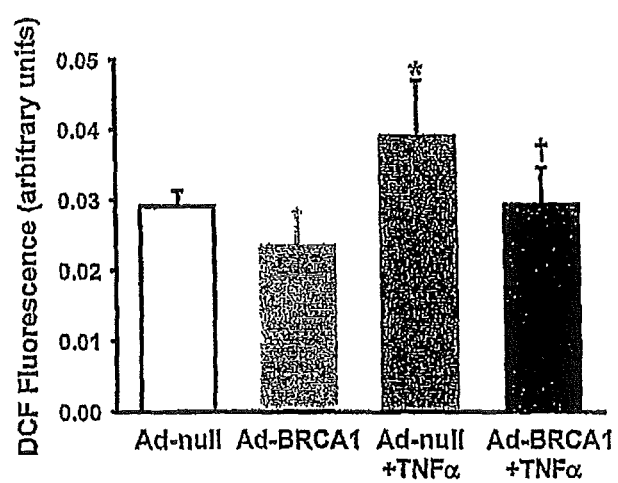
FIG. 26 is a bar graph demonstrating reduction of TNFα-induced reactive oxygen species production in HUVECs by BRCA1 overexpression. Ad-null or Ad-BRCA1 infected HUVECs were harvested and seeded with or without TNFα (20 ng/ml). Intracellular ROS production was determined by measuring the intensity of DCF fluorescence after 12 hours. Data are presented as mean±SD (n=3).

BRCA1 overexpression also reduced TNFα-induced reactive oxygen species production in HUVECs. See FIG. 26.

Figure 27A:
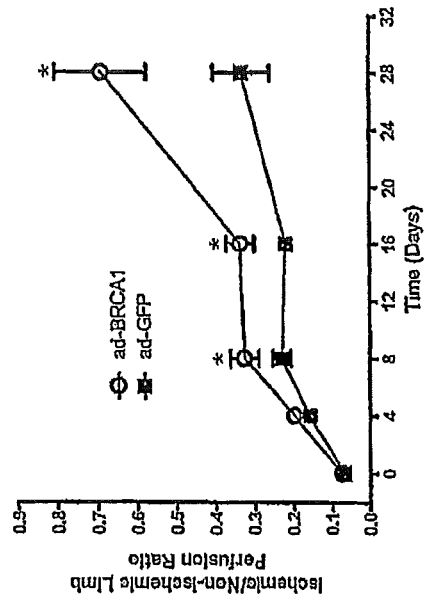
FIGS. 27A through 27D show results from experiments demonstrating BRCA1 overexpression promotes neoangiogenesis in the ischemic hind limb. Hind limb ischemia was performed by ligation and excision of the left femoral artery. Both ad-BRCA1 and ad-GFP (20 µl of $10^{10}$ PFU/ml each) was delivered locally. Following 8 days of ischemia, perfusion was assessed by Laser Doppler flowmetry as depicted in FIG. 27A.
Figure 27B:
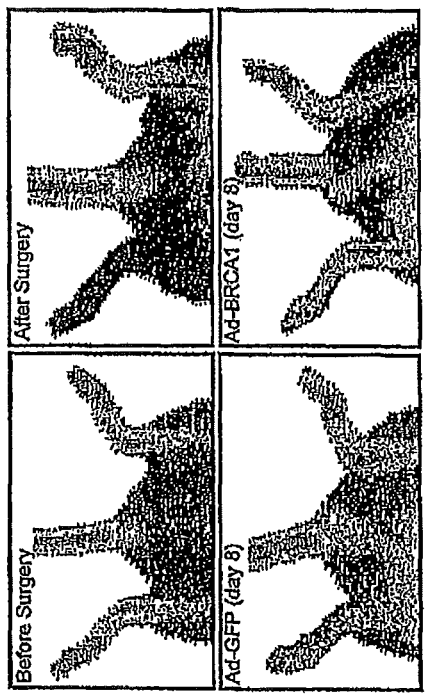
Figure 27C:
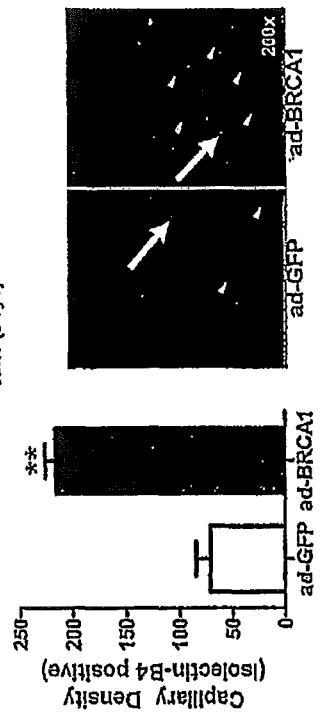
Figure 27D:
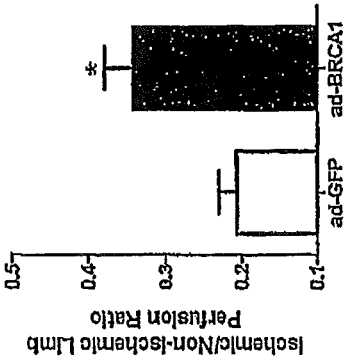

Ad-null or Ad-BRCA1 infected HUVECs BRCA1 was also demonstrated to improve recovery of ischemic hind limbs. To determine the in vivo significance of BRCA1 over-expression, the capacity for neovascularization after inducing hind limb ischemia was assessed in 8-10 week old BALE/c mice. Mice that had received locally administered ad-BRCA1 had significantly greater (p<0.01) limb perfusion as early as day 8 post-surgery in comparison to ad-GFP treated control mice (see FIGS. 27A, 27B and 27C). Increased limb perfusion was consistently and significantly (p<0.01 versus control) higher in ad-BRCA1 mice throughout the timepoints (days 16 and 28) studied (see FIG. 27C). The enhanced recovery of blood flow after hind limb ischemia was associated with a higher capillary density in ad-BRCA1 administered mice in comparison to controls (p<0.01; FIG. 27D).

Figure 28A:
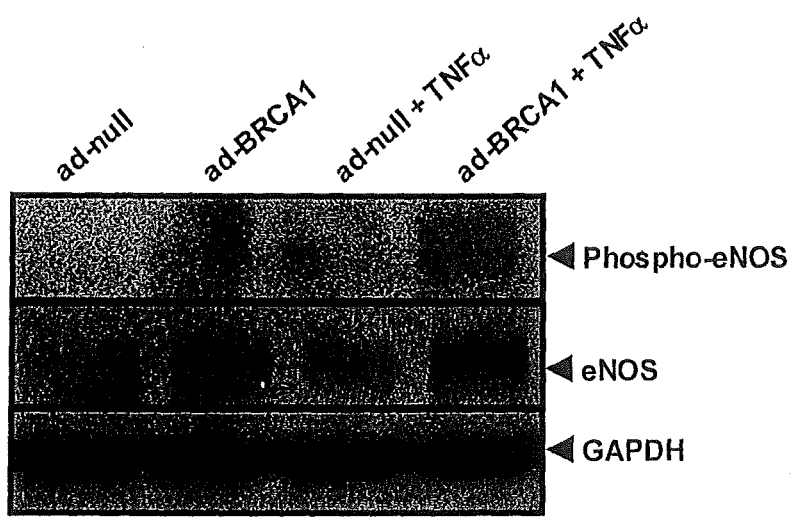
FIGS. 28A through 28E show eNOS/phospho-eNOS, Akt/phospho-Akt and VEGFa protein and RNA expression. Total protein and RNA were extracted from ad-null or ad-BRCA1 infected HUVECs treated thereafter with TNFα for 24 hours.
Figure 28B:
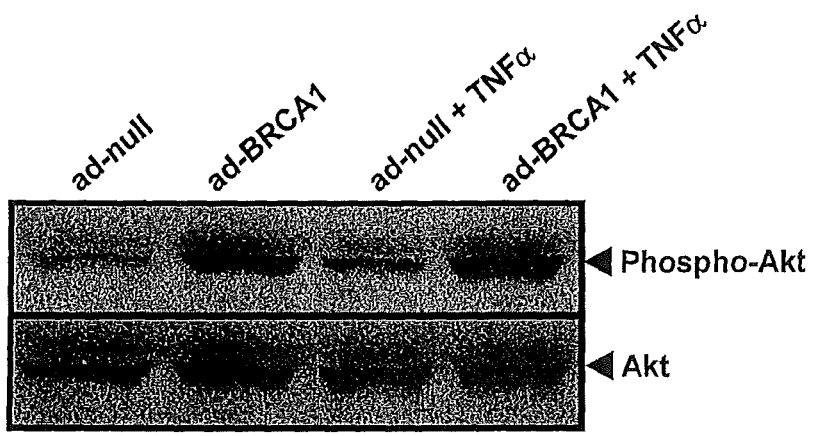
Figure 28C:
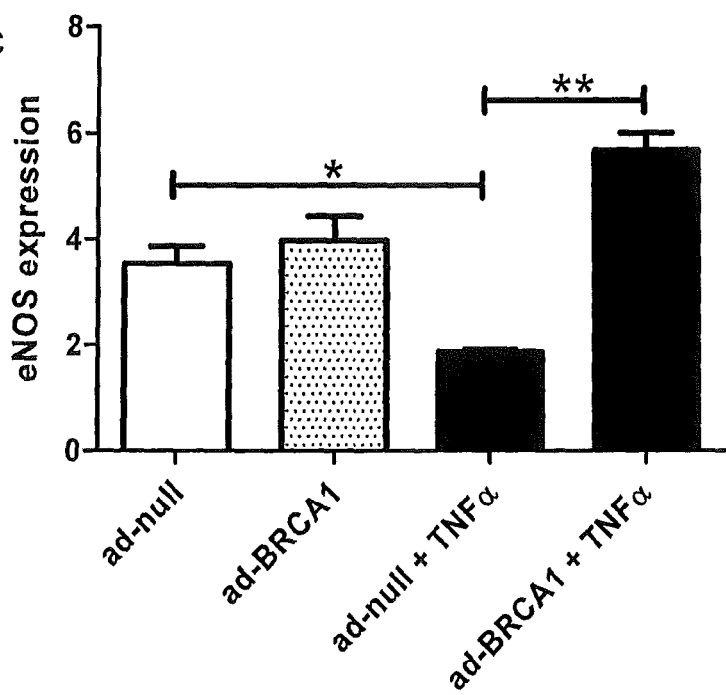
Figure 28D:
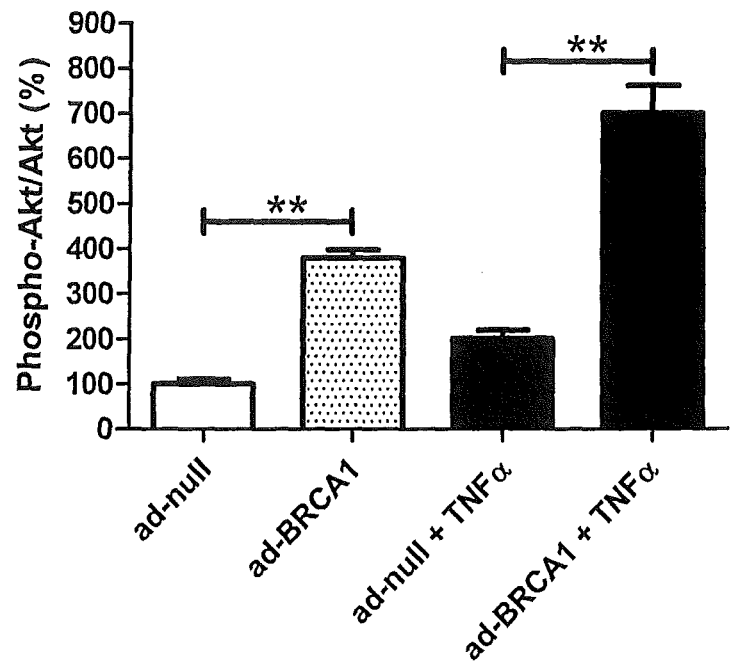
Figure 28E:
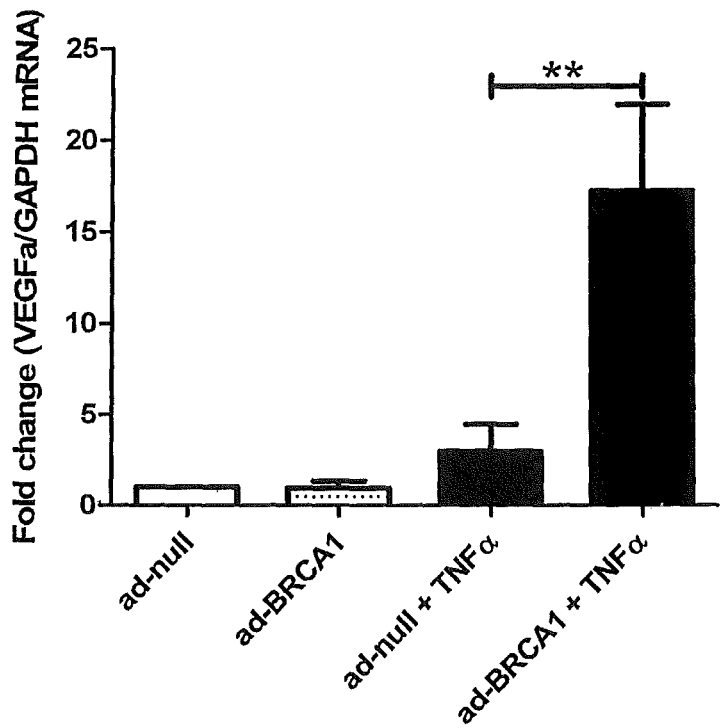
Figure 29A:
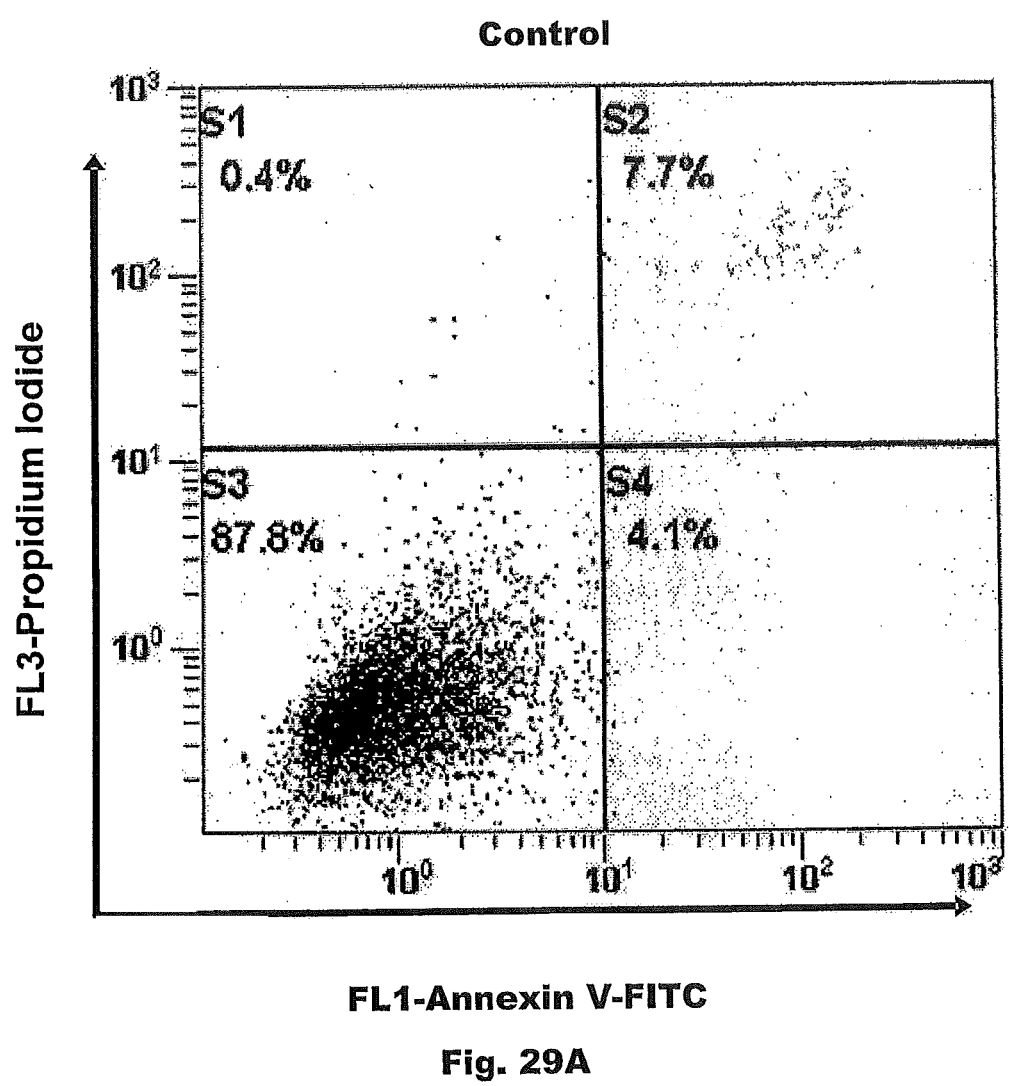
FIGS. 29A and 29B show apoptosis in HUVECs following 24 hours of exposure to TNFα.
Figure 29A:
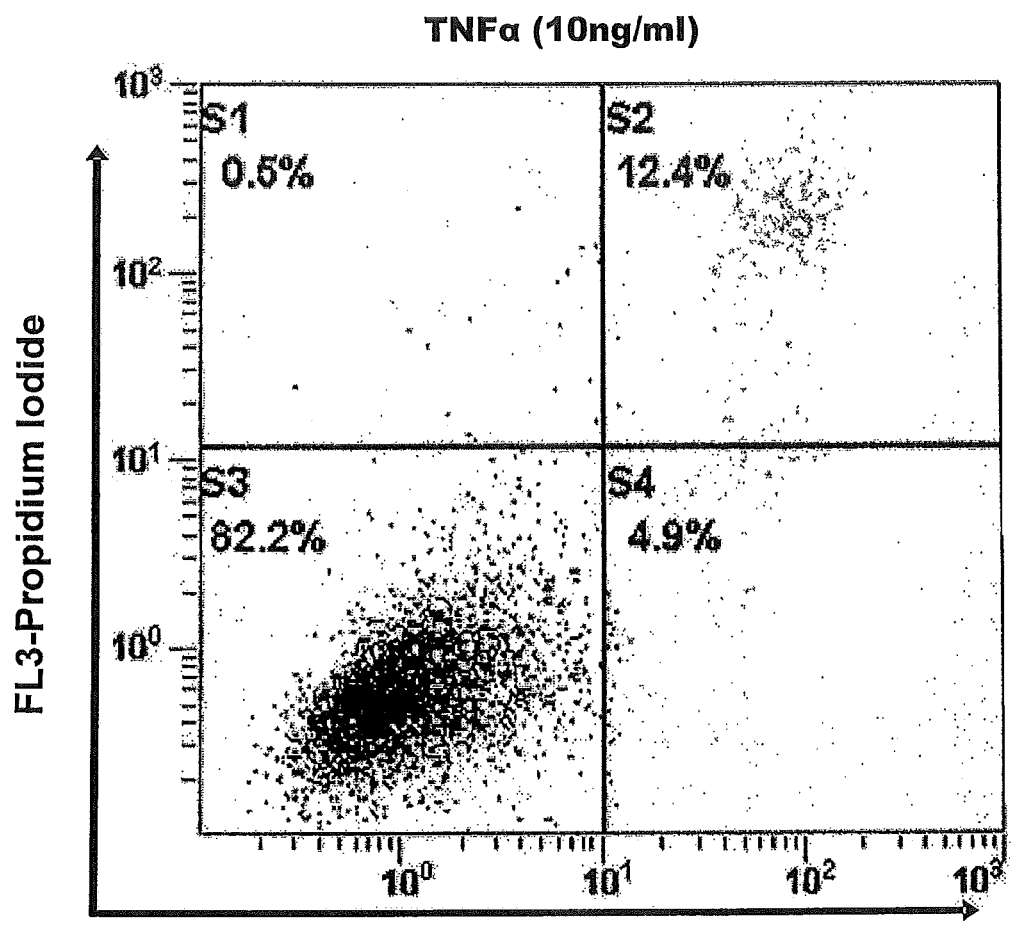
Figure 29A:
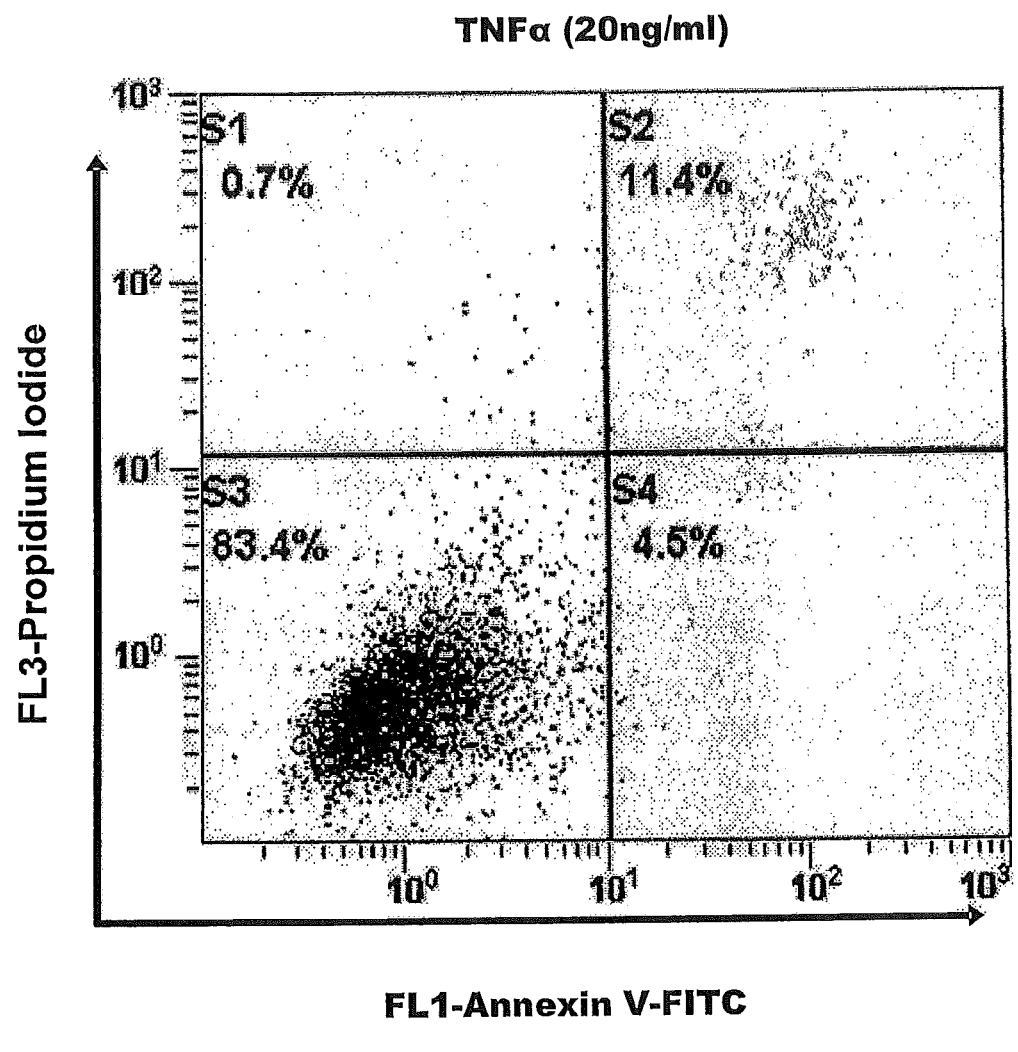
Figure 29A:
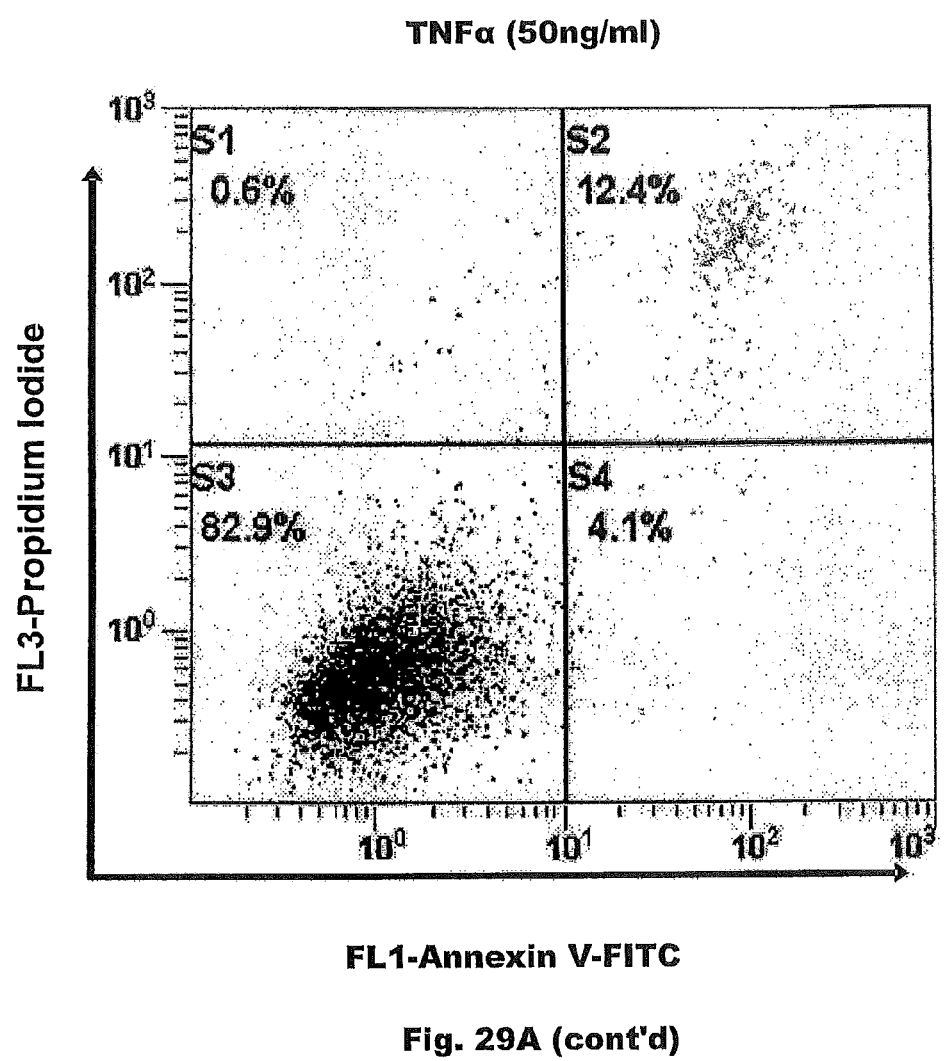
Figure 29A:
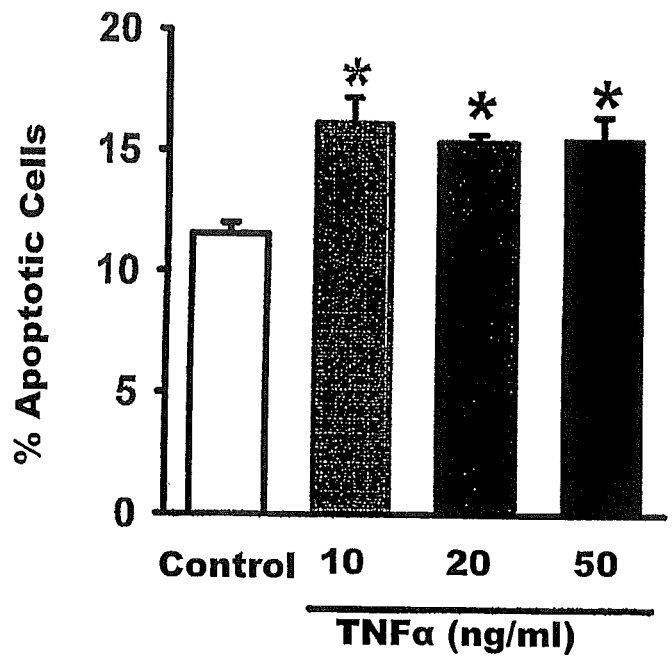
Figure 29B:
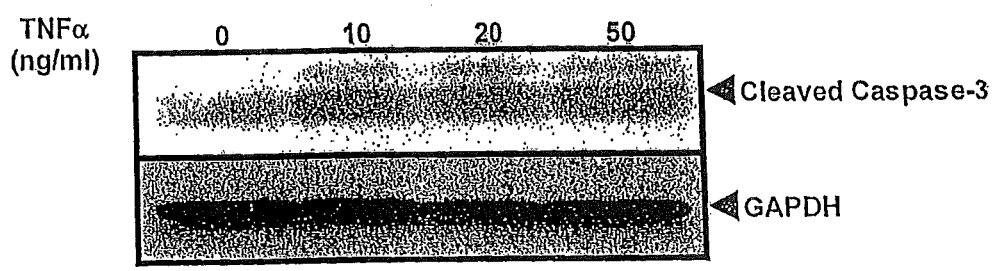
Figure 30A:
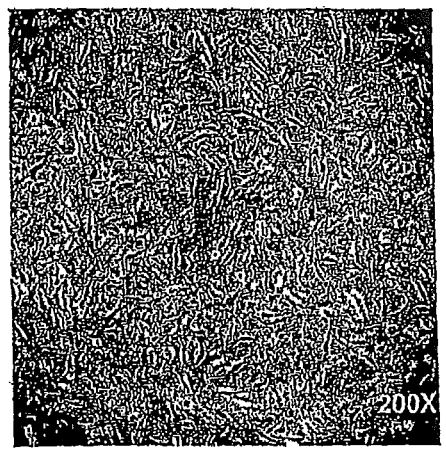
FIGS. 30A and 30B show adenoviral infection efficiency and BRCA1 overexpression in HUVECs.
Figure 30B:
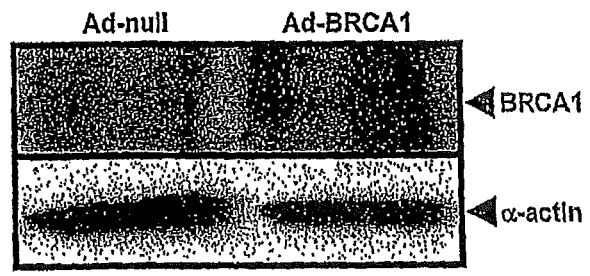

BRCA1 also promoted eNOS, phospho-eNOS, phospho-Akt and VEGFa expression. Since eNOS is essential for endothelial function, the potential regulation of endothelial nitric oxide synthase (eNOS) expression and phosphorylation by BRCA1 was examined via western blot analysis. The significant reduction in eNOS protein levels following TNFα treatment was completely reversed by BRCA1 overexpression (p<0.01; FIGS. 28A and 28C). eNOS phosphorylation at serine 1177 was appreciably raised following concomitant TNFα stimulation and BRCA1 overexpression (see FIGS. 28A and 28C) as was phospho-Akt protein levels (see FIGS. 28B and 28D) and VEGFa transcript levels (FIG. 28E).

Figure 31:
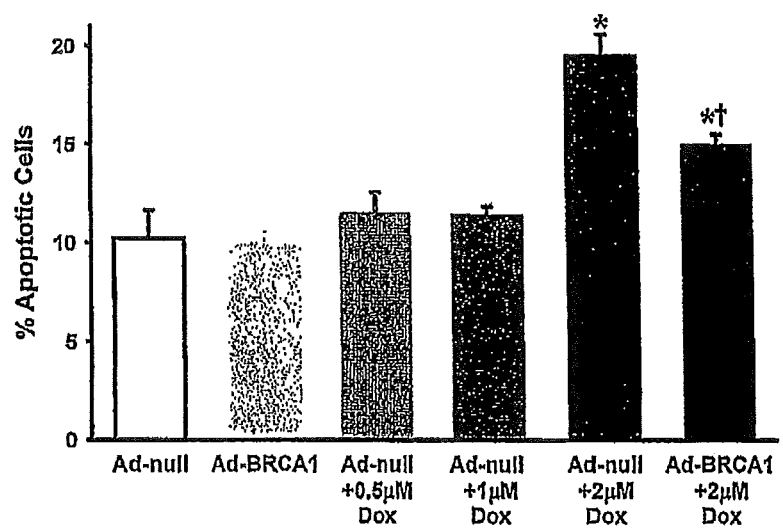
FIG. 31 is a bar graph showing protection of HUVECs against doxorubicin-induced apoptosis by BRCA1 overexpression. To assess the effect of doxorubicin on endothelial cell apoptosis, Ad-null or Ad-BRCA1 infected HUVECs were treated with 0.5, 1.0 or 2.0 µM of doxorubicin for 24 h and flow cytometry analysis was performed using Annexin V-FITC and Propidium Iodide staining. Data was calculated as the percentage of total apoptotic cells and presented as mean±SD (n=3 in triplicate, *p<0.01 vs. Ad-null group, †p<0.01 vs. Ad-null+2 µM Dox group).
Figure 32A:
FIGS. 32A through 32D show BRCA1 limiting atherosclerosis lesion formation in vivo.
Figure 32B:
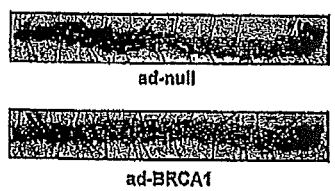
Figure 32C:
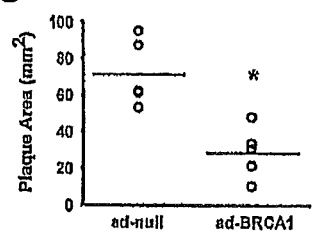
Figure 32D:
Figure 33A:
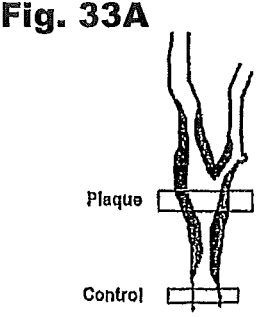
FIGS. 33A through 33D provide evidence of reduced BRCA1 expression in human carotid artery plaques.
Figure 33B:
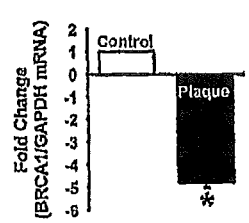
Figure 33C:
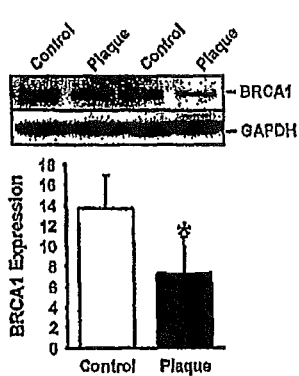
Figure 33D:
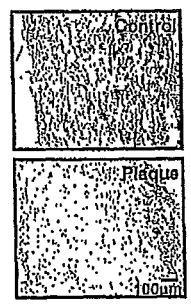

As shown in FIG. 31, BRCA1 overexpression also protected HUVECs against doxorubicin-induced apoptosis.

As shown by these experiments, BRCA1 plays a role in limiting cardiomyocyte apoptosis, and improving cardiac function in response to genotoxic and oxidative stress. Heart specific deletion of BRCA1 promoted severe systolic dysfunction and limited survival.

As shown in FIG. 32, BRCA1 overexpression also limited atherosclerosis lesion formation in vivo. In these experiments, ApoE$^{-/-}$ mice were fed a Western diet for 4 weeks (FIGS. 32A and 32C) or 16 weeks (FIGS. 32B and 32D). Mice were administered ad-null or ad-BRCA1 every second week. Mice in the 4 week study administered ad-BRCA1 exhibited significantly less stained plaque areas in their aortic roots as compared to mice administered ad-null, and mice in the 16 week study administered ad-BRCA1 exhibited less macrophage sequestration as compared to mice administered ad-null.

Male 12 week old Apog$^{-/-}$ mice were fed the Western diet for 4 weeks and were concurrently administered either ad-BRCA1 or ad-GFP (20 μl of $10^{10}$ PFU/ml) on days 0 and 14 via the tail vein. At the end of this diet-adenoviral treatment regime, hearts were embedded in Tissue-Tek O.C.T. and cryosections (5 μm) of the aortic roots were stained with Oil Red 0 for analysis of atherosclerotic lesions.

An additional group of ApoE$^{-/-}$ mice was maintained on the Western diet for 16 weeks and concomitantly treated on day 0 and every 14 days thereafter with either ad-GFP or ad-BRCA1 (20 μl of $10^{10}$ PFU/ml). At the end of this diet-adenoviral treatment regime, en face preparations of the whole aortas were stained with Oil Red 0. Macrophage infiltration into the aortic root was determined in 5 μm sections probed with an F4/80 antibody and visualized with a DAB substrate.

Further, in humans carotid artery plaques exhibited reduced BRCA1 expression as compared to samples from normal control sections of the carotid artery. See FIGS. 33A through 33D. Carotid artery segments were collected at the time of endarterectomy en bloc from intima to external elastic lamina. Two sections were taken from below ("normal") and at (plaque containing) the carotid bifurcation. One was snap frozen in liquid nitrogen and the other fixed and embedded in Tissue-Tek O.C.T. Human carotid cryosections (4-5 μm) were fixed with 4% paraformaldehyde, underwent antigen retrieval in 10 mM sodium citrate (pH 6.0), were blocked with BSA (5% BSA-0.5% Tween-20), probed with anti-BRCA1 (Santa Cruz, 1:50) and stained with a DAB substrate.

Accordingly, an aspect of the present invention relates to use of BRCA1 to inhibit cardiomyocyte apoptosis and/or to improve cardiac function in a subject. Apoptosis, or programmed cell death has been identified as a key mechanism of cell death in acute myocardial infarction, and ischemia-reperfusion injury. In addition, the presence of apoptotic cardiomyocytes has been demonstrated in the hearts of humans with end-stage dilated and ischemic cardiomyopathies. Increasing evidence suggests that continual loss of cardiomyocytes via apoptosis actually contributes to the development of the heart failure phenotype and/or progressive cardiac decompensation. Administration of a BRCA1 construct to subjects suffering from conditions including, but not limited to, acute myocardial infarction, ischemia-reperfusion injury, restenosis, atherosclerosis, vascular disease and/or end-stage dilated and ischemic cardiomyopathies is expected to inhibit further cardiomyocyte apoptosis and improve cardiac function in such subject. Administration of a BRCA1 construct to a subject is also expected to inhibit the development of heart failure phenotype and/or progressive cardiac decompensation due to continual loss of cardiomyocytes via apoptosis. Accordingly, BRCA1 is useful in treating various cardiovascular diseases including, but not limited to, coronary heart disease, coronary artery disease, peripheral artery disease, intermittent claudication and cerebral vascular disease. In addition, BRCA1 delivery can be used to treat subjects at high risk or very high risk of developing cardiovascular disease, for example subjects suffering from familial cholesterolemia, subjects suffering from peripheral artery disease, wherein delivering BRCA1 increases tissue neovascularization and enhances collateral blood flow of the tissue or limbs, i.e. extremities. BRCA1 can also be administered to prevent or reduce cardiac remodeling in a subject.

BRCA1 can be delivered alone or in combination with an existing patient care paradigm for cardiovascular disease such as, but not limited to, statins, ACE inhibitors, angiotensin receptor blockers (ARBs), antihyperlipidemics and antihyperglycaemics.

In one embodiment, BRCA1 is delivered in combination with an angiogenic gene therapy agent such as VEGF which induces blood vessel growth and thus increases blood flow to the heart. In this embodiment, genes for BRCA1 and VEGF can be administered in a single construct, as two separate constructs in single delivery system, or as two separate constructs in separate delivery systems administered simultaneously or at different times.

It is well-established that an individual having suffered a first acute coronary event will very often undergo a second or subsequent, and oftentimes more serious, second coronary event or events within several months to several years after the first event. In one embodiment of the present invention, BRCA1 is administered to such subjects after the first acute coronary event to prevent or inhibit further damage leading to a second or subsequent coronary event or events.

As also shown by these experiments, BRCA1 protects endothelial cells against inflammation-induced apoptosis, through a mechanism that involves up-regulation of eNOS and reduced ROS production. Accordingly, administration of a BRCA1 construct is expected to limit aberrant vascular remodeling. These data also indicate that patients with BRCA1 mutations or cancer syndromes may be at exaggerated risk of native and transplant atherosclerosis and graft dysfunction, particularly in the setting of DNA damaging immunosuppressants.

Accordingly, another aspect of the present invention relates to a method for inhibiting inflammation-induced endothelial cell apoptosis and/or restoring endothelial function in a subject which comprises delivering BRCA1 to endothelial cells. Inhibiting inflammation-induced endothelial cell apoptosis and/or restoring endothelial function in a subject via administration of BRCA1 is expected to be useful in treating or preventing atherosclerosis or promoting regression of atherosclerotic lesions. BRCA1 delivery is also expected to be useful in the treatment of disorders linked to endothelial dysfunction including, but not limited to, pulmonary artery hypertension, systemic hypertension, diabetes, insulin resistance, sepsis, acute respiratory distress syndrome, and pregnancy induced hypertension.

Endothelial cell apoptosis, in response to inflammatory, ischemic and hypoxic stressors, and has also been identified as a target for therapies aimed at improving graft patency.

A wide range of chemotherapy agents have been associated with cardiotoxicity, of which the anthracyclines and related compounds are the most frequently implicated agents. As also shown by experiments herein, delivery of BRCA1 to cardiomyocytes inhibits cardiotoxicity of the anthracycline chemotherapeutic agent doxorubicin.

Accordingly, another aspect of the present invention relates to a method for inhibiting or decreasing cardiotoxicity in a subject receiving a cardiotoxic chemotherapeutic agent comprising delivering BRCA1 to the subject. Systemic, local or adjunctive delivery of BRCA1, for example during bypass surgery or angioplasty, is expected to be useful in rescuing or protecting individuals from chemotherapy induced cardiac failure.

Inhibiting the cardiotoxicity of such agents through delivery of BRCA1 is expected to allow higher doses of such chemotherapeutic agents to be administered thus enhancing their efficacy for the treatment of cancer. Accordingly, another aspect of the present invention relates to enhancing efficacy of cardiotoxic chemotherapeutic agents by delivering BRCA1 to a subject receiving a cardiotoxic chemotherapeutic agent so that higher doses of the chemotherapeutic agent can be administered. In this embodiment, BRCA1 can be administered at the same time as the chemotherapeutic agent or prior to administration of the chemotherapeutic agent so that sufficient protective levels of BRCA1 are expressed during administration of the chemotherapeutic agent.

Further, these experiments indicate that BRCA1 mutant breast and ovarian cancer patients are at higher risk to cardiotoxicity of cardiotoxic chemotherapeutic agents such as doxorubicin and agents similar thereto. Accordingly, another aspect of the present invention relates to assessing expression of BRCA1 or a BRCA1 mutant in a subject suffering from cancer to provide a pharmacogenomic basis to guide chemotherapeutic decision making.

The experiments set forth herein are also indicative of subjects having a BRCA1 mutation being at higher risk of native and transplant atherosclerosis and graft dysfunction, particularly in the setting of DNA damaging immunosuppressants. It is expected that delivery of BRCA1 to a subject undergoing, for example, a heart transplant donor operation will protect the subject against the development of transplant atherosclerosis in response to immunosuppressants. Thus, another aspect of the present invention relates of a method of protecting against or inhibiting development of transplant atherosclerosis in response to immunosuppressants in a subject at risk which comprises delivering BRCA1 to the subject.

BRCA1 delivery is also expected to be useful in subjects with hepatic steatosis, insulin resistance or adiposity, to decrease free fatty acid oxidation and/or fatty acid synthesis with resultant treatment of dyslipidemia.

By "subject", as used herein it is meant to be inclusive of all animals and in particular mammals such as, but not limited to, humans and dogs as well as agricultural animals such as bovine, ovine, and porcine.

By "delivering BRCA1", "BRCA1 delivery", or "administration of BRCA1" as used herein, it is meant to include delivery of a gene construct comprising a BRCA1 gene or an active fragment thereof to be expressed in cells, delivery of a progenitor cell overexpressing BRCA1 or an active fragment thereof, or delivery of the BRCA1 protein or an active fragment thereof.

An exemplary active fragment useful in the present invention is the BRCA1 c-terminus domain.

For purposes of the present invention, when delivering a BRCA1 polynucleotide, a BARD1 antisense is not administered in combination therewith.

For purposes of the present invention, when delivering a progenitor cell overexpressing BRCA1, the stem cell does not express at least one polypeptide selected from the group consisting of Fosb; NRAP; MEF2A; Furin; and TGFβ1 or and at least one polypeptide selected from the group consisting of integral membrane protein 2A; insulin-like growth factor binding protein 4; thymus cell antigen 1, theta; selenoprotein P, plasma 1; and glycoprotein 38.

For purposes of the present invention, when delivering a BRCA1 protein, a STAT activating agent is not administered therewith as a BRCA/STAT complex.

By "BRCA1 gene", for purposes of the present invention, it is meant to include any polynucleotide sequence encoding breast cancer susceptibility gene 1 or a variant or active fragment thereof which maintains tumor suppressor activity and which does not comprise a mutation implicated in the hereditary predisposition to familial breast and ovarian cancers. An exemplary polynucleotide encoding BRCA1 useful in the present invention is human BRCA1 gene (NM_007294.2).

The sequence listing sets forth the polynucleotide sequences of human BRCA1 gene (NM_007294.2 (SEQ ID NO:1) and known isoforms NM_007295.2 (SEQ ID NO:2), NM_007296.2 (SEQ ID NO:3), NM_007297.2 (SEQ ID NO:4), NM_007298.2 (SEQ ID NO:5), NM_007299.2 (SEQ ID NO:6), NM_007300.2 (SEQ ID NO:7), NM_007302.2 (SEQ ID NO:8), NM_007303.2 (SEQ ID NO:9), NM_007304.2 (SEQ ID NO:10), NM_007305.2 (SEQ ID NO:11) and BC072418 (SEQ ID NO:12).

Multiple BRCA1 mutations not encompassed within the present invention have been compiled and can be found in the Breast Cancer Information Core (BIC) database. Also see Fackenthal and Olopade Nature 2007 7: 937-948. There are 27 BRCA1 missense mutations that have been reported which affect 15 codons. Examples of founder mutations that are more common in certain nationalities are: 185delAG in exon 1; 1135insA in exon 11; 1675delA in exon 11; 3171ins5 in exon 11; 4153delA in exon 11; and 5382insC in exon 20. These mutations are mainly in the BRCA1 regions encoding the RING and BRCT domains, which are involved in protein-protein interactions. There are also four known BRCA1 mutations in the first codon (M1I, M1R, M1T, and M1V). The effect of the base change in this first codon is more likely due to translation initiation differences than amino acid substitutions. Additional missense mutations may be due to splicing defects when in proximity to intron-exon junctions. There are over 670 truncating mutations that have been reported for BRCA1, these include nonsense mutations, frame-shift mutations due to small insertions and/or deletions, and mutations within splicing sites. These mutations occur throughout the length of the gene. Larger genomic alterations are also known to result in duplications or deletions of one or more exons, producing premature stop codons. Polynucleotides with any of these mutations are not encompassed within BRCA1 of the present invention.

In addition to the polynucleotide sequence encoding BRCA1 or an active fragment thereof, gene constructs used in the present invention may further comprise regulatory DNA sequences operably linked thereto. Regulatory DNA sequence may be autologous or heterologous regulatory sequences such as promoters or enhancers, wherein upon expression of these DNA sequences in human cells, including human cells in which the DNA sequences are normally repressed or functionally inactive, BRCA1 is expressed. In such constructs, the regulatory sequences may be operably linked to BRCA1 encoding mature BRCA1 protein or a variant thereof which maintains tumor suppressor activity and which does not comprise a mutation implicated in the hereditary predisposition to familial breast and ovarian cancers. In alternative constructs, the regulatory sequences may be operably linked to a BRCA1 polynucleotide fragment which does not encode full length BRCA1 gene product, but which contains a sufficient portion of the BRCA1 nucleotide sequence to target the genetic construct to the native BRCA1 locus in a host cell wherein the BRCA1 gene may be inactive due to repression or mutation. Upon introduction of such constructs into the host cell, the regulatory sequence is integrated into the host cell genome proximal to the endogenous BRCA1 gene via homologous recombination ("gene targeting"), thereby activating or de-repressing BRCA1 gene expression.

BRCA1 polynucleotides useful in the present invention include (a) DNA molecules comprising an open reading frame (ORF) with an initiation codon of human BRCA1 gene (NM_007294.2; SEQ ID NO:1); (b) DNA molecules comprising the coding sequence for the mature BRCA1 gene product of human BRCA1 gene (NM_007294.2; SEQ ID NO:1); and (c) DNA molecules which comprise a sequence substantially different from those described above but which, due to the degeneracy of the genetic code, still encode the BRCA1 gene product. Since the genetic code is well known in the art, it is routine for one of ordinary skill in the art to produce the degenerate variants described above without undue experimentation. BRCA1 polynucleotides useful in the present invention which encode a BRCA1 polypeptide may include, but are not limited to, those encoding the amino acid sequence of the mature polypeptide by itself; the coding sequence for the mature polypeptide and additional, non-coding sequences, including for example introns and non-coding 5' and 3' sequences, such as the transcribed, untranslated regions (UTRs) or other 5' flanking sequences that may play a role in transcription (e.g., via providing ribosome- or transcription factor-binding sites), mRNA processing (e.g. splicing and polyadenylation signals) and stability of mRNA; and the coding sequence for the BRCA1 polypeptide operably linked to a regulatory DNA sequence, including an autologous or heterologous regulatory DNA sequence such as a promoter or enhancer.

BRCA1 polynucleotide also useful in the present invention are variants of BRCA1, which encode portions, analogs or derivatives of the BRCA1 polypeptide, which maintain tumor suppressor activity and which do not comprise a mutation implicated in the hereditary predisposition to familial breast and ovarian cancers. Variants may occur naturally, such as a natural allelic variant. By an "allelic variant" is intended one of several alternate forms of a gene occupying a given locus on a chromosome of an organism (see Lewin, B., ed., Genes II, John Wiley & Sons, New York (1985)). Non-naturally occurring variants may be produced using art-known mutagenesis techniques. Such variants include those produced by nucleotide substitutions, deletions and/or additions. The substitutions, deletions and/or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the tumor suppressor properties and activities of the BRCA1 gene product or portions thereof. Also especially preferred in this regard are conservative substitutions.

Also useful in the present invention are BRCA1 polynucleotides comprising a polynucleotide having a nucleotide sequence at least 90% identical, at least 95%, at least 96%, at least 97%, at least 98% or at least 99% identical to (a) human BRCA1 gene (NM_007294.2; SEQ ID NO:1); (b) a nucleotide sequence encoding the full-length BRCA1 polypeptide encoded by human BRCA1 gene (NM_007294.2; SEQ ID NO:1); and (c) a nucleotide sequence complementary to any of the polynucleotide sequences in (a) or (b) above. By a polynucleotide having a nucleotide sequence at least, for example, 95% "identical" to a reference nucleotide sequence encoding a BRCA1 polypeptide, it is intended that the nucleotide sequence of the polynucleotide is identical to the reference sequence except that the polynucleotide sequence may include up to five point mutations per each 100 nucleotides of the reference nucleotide sequence encoding the BRCA1 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Determining whether a polynucleotide is at least 90%, at least 95%, at least 96%, at least 97%, at least 98% or at least 99% identical to human BRCA1 gene (NM_007294.2; SEQ ID NO:1), can be determined routinely using various commercially available computer programs including, but not limited to, FASTA, Gap or Bestfit, which are programs in Wisconsin Package Version 10.0, Genetics Computer Group (GCG), Madison, Wis. The BESTFIT program (Wisconsin Sequence Analysis Package, Version 8 for Unix, Genetics Computer Group, University Research Park, 575 Science Drive, Madison, Wis. 53711), employs a local homology algorithm (Smith and Waterman, Advances in Applied Mathematics 2: 482-489 (1981)) to find the best segment of homology between two sequences. Unless otherwise specified, default parameters for a particular program or algorithm are used. For instance, percent sequence identity between polynucleotides can be determined using FASTA with its default parameters (a word size of 6 and the NOPAM factor for the scoring matrix) or using Gap with its default parameters as provided in GCG Version 6.1.

Due to the high incidence of alternative splicing in human BRCA1 gene (NM_007294.2; SEQ ID NO:1), there are several known isoforms (NM_007295.2 (SEQ ID NO:2), NM_007296.2 (SEQ ID NO:3), NM_007297.2 (SEQ ID NO:4), NM_007298.2 (SEQ ID NO:5), NM_007299.2 (SEQ ID NO:6), NM_007300.2 (SEQ ID NO:7), NM_007302.2 (SEQ ID NO:8), NM_007303.2 (SEQ ID NO:9), NM_007304.2 (SEQ ID NO:10), NM_007305.2 (SEQ ID NO:11) and B0072418 (SEQ ID NO:12)) present naturally. Due the degeneracy of the genetic code, one of the ordinary skill in the art will immediate recognize that a large number of the nucleic acid molecules having a sequence at least 90%-99% identical to the nucleic acid sequence (NM_007294.2 (SEQ ID NO:1) or its isoforms) will encode a polypeptide having BRCA1 protein activity. In fact, since degenerate variants of the polynucleotide all encode the same polypeptide, this will be clear to the skilled artisan even without performing the above-described comparison assay. It will be further recognized by one of ordinary skill in the art that, for such polynucleotides that are not degenerate variants, a reasonable number will also encode a polypeptide having BRCA1 protein activity. This is because the skilled artisan is fully aware of amino acid substitutions that are either less likely or unlikely to significantly affect protein function (e.g., replacing one aliphatic amino acid with a second aliphatic amino acid). For example, guidance concerning how to make phenotypically silent amino acid substitutions is provided in Bowie, J. U., et al., Science 247:1306-1310 (1990), and the references cited therein.

In one embodiment of the present invention, BRCA1 is administered as a gene construct in a vector. Expression vectors useful in the present invention include chromosomal, episomal- and virus-derived vectors, e.g., vectors derived from bacterial plasmids, bacteriophages, yeast episomes, yeast chromosomal elements, viruses and vectors derived from combinations thereof, such as cosmids and phagemids as well as non-viral vectors such as polymers. Examples of vectors used in human gene therapy include, but are not limited to, adenovirus (Stewart et al. Gene Ther. 2006 November; 13(21):1503-11), retrovirus (Cavazzana-Calvo et al. Science 2000 669-672; Bonini et al. Science 1997 1719-1724; Gong et al. Gene Ther. 2007 November; 14(21):1537-42), lentivirus (Vigna et al. J. Gene. Med. 2000 308-316; Park et al. Nat. Genet. 2000 49-52; Shi et al. J Thromb Haemost. 2007 February; 5(2):352-61), vaccinia, poxviruses, adeno-associated virus, herpes simplex virus, nonviral vectors, and plasmids (Edelstein et al. J Gene Med 2007 9: 833-842). Delivery of a vector comprising BRCA1 may be achieved by a number of mechanisms including, but not limited to, infection, liposomal delivery, transfection, and gene gun. Viral vectors have been disclosed to be particularly effective in cardiac gene delivery due to their high transduction efficiency (Yockman et al. J Control Release. 2008 Jul. 6. [Epub ahead of print]). Viral vectors routinely used in cardiovascular gene therapy are adenoviruses (Yla-Herttuala et al., Nat Med 2007 9:694-701). Adenovirus-associated vectors (AAV), which are believed to be safer, injectable vectors in vivo for gene therapy, are also useful (Gregorevic et al. Nature Medicine 2004 Vol 10, (8):828-834). AAV is a parvovirus with a single-stranded DNA genome. The wild-type virus cannot replicate without the presence of a helper virus. There are multiple serotypes for this virus, but serotype 2 (AAV2) is the most commonly used (Wu et al. Mol Ther 2006 14: 316-327).

The BRCA1 polynucleotide may be joined to a vector containing a selectable marker for propagation in a host. Generally, a plasmid vector is introduced into mammalian or avian cells in a precipitate, such as a calcium phosphate precipitate, or in a complex with a charged lipid (e.g., LIPOFECTAMINE™; Life Technologies, Inc.; Rockville, Md.) or in a complex with a virus (such as an adenovirus) or components of a virus (such as viral capsid peptides). If the vector is a virus, it may be packaged in vitro using an appropriate packaging cell line.

In one embodiment, vectors comprising cis-acting control regions to the BRCA1 polynucleotide are used. Appropriate trans-acting factors may be supplied by the host, by a complementing vector or by the vector itself upon introduction into the host.

In one embodiment, the vectors provide for specific expression, which may be inducible and/or cell type-specific.

In one embodiment, the BRCA1 polynucleotide is operably linked to an appropriate regulatory sequence, for example, a promoter such as the SV40 early and late promoters, promoters of retroviral LTRs, the CMV immediate early promoter, the HSV thymidine kinase promoter, metallothionein promoters, and native human BRCA1 promoters and derivatives thereof, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiation codon (AUG) at the beginning and a termination codon (UAA, UGA or UAG) appropriately positioned at the end of the polypeptide to be translated.

In one embodiment, the BRCA1 polynucleotide is operably linked to a regulatory genetic sequence, which may be an autologous or a heterologous regulatory genetic sequence, to form a genetic construct. Genetic constructs according to this aspect of the invention are intended to encompass not only those comprising a polynucleotide encoding BRCA1 protein operably linked to a regulatory DNA sequence, but also those constructs comprising one or more regulatory sequences operably linked to a BRCA1 polynucleotide fragment which does not encode BRCA1 protein, but which contains a sufficient portion of the BRCA1 nucleotide sequence (a "targeting fragment") to target the genetic construct to the native BRCA1 locus upon introduction into a host cell wherein the BRCA1 gene may be inactive due to repression or mutation. These constructs may be inserted into a vector as above, and the vectors introduced into a host cell, the genome of which comprises the target gene, by any of the methods described above. The BRCA1 polynucleotide will then integrate into the host cell genome by homologous recombination. In the case of a construct comprising an autologous or heterologous regulatory sequence linked to a targeting BRCA1 polynucleotide fragment, the regulatory sequence will be targeted to the native BRCA1 locus in the host cell, and will amplify or de-repress the expression of the native BRCA1 gene in the host cell, thereby increasing the level of production of BRCA1 protein. Alternatively, such gene targeting may be carried out using genetic constructs comprising the above-described BRCA1 targeting fragment in the absence of a regulatory sequence. Such methods of producing genetic constructs, introducing genes of interest into a host cell via homologous recombination and producing the encoded polypeptides are generally described in U.S. Pat. No. 5,578, 461; WO 94/12650; WO 93/09222; and WO 90/14092, teachings of which are herein incorporated by reference in their entirety.

Transcription of the DNA encoding BRCA1 by the host may be increased by inserting an enhancer sequence into the vector. Enhancers are cis-acting elements of DNA, usually from about 10 to 300 bp, that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers. In an alternative embodiment of the invention, transcriptional activation of the BRCA1 gene may be enhanced by inserting one or more concatamerized elements from the native human or BRCA1 promoter into the vector.

Viral vector delivery may be enhanced by addition of a peptide as described by Gratton et al. (Nature Medicine 2003 357-362) and Kahnel et al. J. Virol. 2004 December; 78(24): 13743-54)

Non-viral vectors have also been described with increased transfection efficiency (Muller et al. Cardiovasc Res 2007 73(3): 453-462) and can be used in the present invention. In one embodiment a polymer that employs lipid modifications to improve transfection or target cardiovascular tissues can be used. An example is water-soluble lipopolymer (WSLP) consisting of a low molecular weight branched PEI (1800) and cholesterol. The cholesterol moiety adds extra condensation by forming stable micellular complexes and can be employed for myocardial gene therapy to exploit the high expression of lipoprotein lipase found within cardiac tissue. Bioreducible polymers made of poly(amidopolyethylenimines) (SS-PAEI) can also be used. SS-PAEIs breakdown within the cytoplasm through inherent redox mechanisms and provide for high transfection efficiencies (upwards to 60% in cardiovascular cell types) with little to no demonstrable toxicity.

In another embodiment of the present invention, BRCA1 is administered as naked DNA delivered directly to the cardiac myocardium (Hao et al. Cardiovasc Res. 2007 73(3): 481-487) or endotheilium.

Microbubble based gene therapy techniques as described by Shen et al. (Gene Therapy 2008 (15) 257-266) can also be used to deliver the BRCA1 gene.

In another embodiment, the BRCA1 protein is delivered directly to the cardiac myocardium (Hao et al. Cardiovasc Res. 2007 73(3): 481-487; Laham et al. J Am Coll Cardiol. 2000 December; 36(7):2132-9). In this embodiment, BRCA1 may be administered as a fusion protein. A better understanding of active peptide sequences involved in cell-binding, fusogenic peptides, and nuclear localization has contributed to protein delivery strategies (Morris et al., Curr Opin Biotechnol 2000 11:461-466). Nuclear localization signals (NLS) can direct protein through the nuclear pore complex and are often characterized by being rich in the basic amino acids, such as lysine and arginine (Dingwall and Laskey, 1991, TIBS16: 478-481). The SV40 large T antigen, Pro-Lys-Lys-Lys-Arg-Lys-Val, has been viewed as the model for mapping nuclear targeting sequences. Consensus sequences have been described in many organisms and the list of such signals keeps growing (Mekhail et al., 2007, Molec Biol of the Cell 18: 3966-3977). Fusing NLS signals to gene sequences is commonly used to target cells and/or the nucleus; examples are the SV40 NLS and the HIV-1 Transactivator of Transcription (TAT) sequences. Other methods of targeting proteins to cells also include nanoparticles, antibodies, ligands, peptide sequences, etc.

Various means for delivery of BRCA1 can be used.

In one embodiment, a BRCA1 gene construct such as AdBRCA1 is delivered percutaneously at the time of coronary or percutaneous angiography or angioplasty. In another embodiment, a BRCA1 gene construct such as AdBRCA1 is delivered by intramyocardial injection into the left or right ventricle at the time of coronary artery bypass surgery. Endomyocardial injections using a nonflouroscopic, 3-dimensional mapping and injection (NOGA) catheter-based system as well as percutaneous, catheter-based intramyocardial injection provide practical, feasible, and potentially safe approaches for intramyocardial gene transfer (Fuchs et al. Catheter Cardiovasc Interv. 2006 Sepetember; 68(3):372-8; Ripa et al. Eur Heart J. 2006 August; 27(15):1785-92;). Direct intramyocardial delivery of a replication-deficient adenovirus-containing the gene can also be used (Rivard et al. Gene Ther. 2006 November; 13(21):1503-11). In another embodiment, particularly useful in non-revascularizable patients to improve angiogenesis and cardiac function, delivery can be achieved via a small mini thoracotomy (Kastrup et al. J Am Coll Cardiol. 2005 Apr. 5; 45(7):982-8; Symes et al. Ann Thorac Surg. 1999 September; 68(3):830-6; discussion 836-7). In another embodiment, BRCA1 overexpressing progenitor cells are delivered systemically by intravenous delivery to patients with coronary artery disease or heart failure.

Strategies to augment BRCA1 delivery in the heart and blood vessels (macro and microvasculature) using gene, cell or protein based approaches encompassed within the present invention include, but are not limited to, administration with or without systemic and/or local therapies such as statins, angiotensin antagonists, aspirin, clopidogrel, or growth factors.

Hundreds of gene therapy trials have been performed and are currently ongoing, and dose varies depending on the indications. While not be limiting to a particular dose range for BRCA1 in the present invention, based upon many clinical trials with human vascular endothelial growth factor (VEGF), it is expected that subjects can be administered anywhere from 500 to 16,000 µg of a BRCA1 construct in single or multiple sessions. Doses can also be described in particle units (PU) or plaque forming units (pfu), which can range from 100 to $10^{13}$. These trials, among others, are reviewed in Kalka and Baumgartner (2008, Vascular Medicine 13:157-172) for the treatment of peripheral arterial occlusion diseases and other examples can be found in Evans et al. (2008, Arthritis Research & Therapy 10(110): 1-9).

The following nonlimiting examples further illustrate the present invention.

EXAMPLES

Example 1

Animals

All animal protocols used in this study received approval and were according to institutional guidelines. Wild type mice on a C57Bl/6 background and purchased from Jackson Laboratories. All mice were maintained in sterile micro-isolator cages under pathogen-free conditions. Food and water was available ab-libidum, and all handling was done under a laminar-flow hood according to standard procedures for maintaining clean mice. Sprague-Dawley rat pups (1-2 day old) were obtained from (Charles-River).

Cardiac specific BRCA1 knockout mice were generated on a mixed background. Mice homozygous for a floxed BRCA1 allele were crossed with heterozygous mice that express Cre recombinase under the control of the α-myosin heavy chain (αMHC-Cre) promoter. Mice demonstrating the αMHC-Cre$^{tg/+}$; BRCA1$^{fl/fl}$ combination were identified as cardiomyocyte specific BRCA1 knockouts (CM-BRCA1-KO) while littermates not expressing the Cre transgene were used as controls. Each mouse was genotyped using routine PCR methods with the following sets of primers: BRCA1 floxed allele-004: 5'-CTGGGTAGTTTGTAAGCATGC-3' (SEQ ID NO:13); 005: 5'-CAATAAACTGCTGGTTCTAGG-3' (SEQ ID NO:14) and 006: 5;-CTGCGAGCAGTCTTCAGAAAG-3' (SEQ ID NO:15); αMHC-Cre transgene-5'-ATGACAGA-CAGATCCCTCCTATCTCC-3' (SEQ ID NO:16) and 5'-CT-CATCACTCGTTGCATCGAC-3' (SEQ ID NO:17).

Example 2

Experimental Myocardial Infarction (MI)

C57Bl/6 WT mice were anesthetized using 2% isofluran mixed with saturated oxygen and ventilated. MI was induced by permanent occlusion of the left anterior descending coronary artery with a 7-0 silk suture immediately distal to main ramification. Significant discoloration in the ischemic area was considered indicative of successful coronary occlusion. In sham MI group, the same surgical procedure was performed, except the coronary ligation step. Mice were sacrificed at stipulated time points.

Example 3

Doxorubicin Treatment and Exogenous BRCA1 Delivery

Eight to nine weeks old C57Bl/6 WT males with median body weight 24 g were treated with a single intraperitoneal dose of 10 mg/kg doxorubicin (Sigma Aldrich, USA).

Concomitantly, 40 µl of adenoviral construct containing either human-BRCA1, GFP or Null (Vector Biolabs, USA) was given intravenously with the concentration of $1 \times 10^{10}$ PFU/ml.

Example 4

Two-Dimensional Echocardiography

Double-blinded echocardiography was performed on the doxorubicin- and adenoviral vectors-treated mice 3 days and 7 days post-treatment. Echocardiographic imaging was performed under light sedation (1-1.5% isofluran) using an HDI 5000cv echocardiographic system (Philips Ultrasound, Bothell, Wash.) equipped with a compact 15 MHz broadband linear transducer (CL15-7). Two-dimensional (2-D) imaging was performed in the parasternal long- and short-axis views. An M-mode cursor was positioned perpendicular to the interventricular septum and posterior wall of the LV at the level of the papillary muscles, and M-mode images were obtained for measurement of chamber dimensions throughout the cardiac cycle. End-diastolic posterior LV wall thickness, LV end-diastolic (LVEDD) and end-systolic LV dimension (LVESD) were measured. During diastole, LV dimension and wall thickness were measured from the maximum chamber cavity; during systole, they were measured during maximum anterior motion of the posterior wall. Images were stored to the hard drive for off-line analysis.

Fractional shortening (FS) was defined as [(LVEDD–LVESD)/LVEDD]. LV ejection fraction was defined as [(LVEDD$^3$–LVESD$^3$)/LVEDD$^3$]×100. Stroke volume (SV) and cardiac output (CO) was calculated from the following equations. CSA=(AoD/2)$^2$×π, SV=CSA×Aortic VTI, CO=SV×HR. In all cases, three beats were averaged for each measurement.

Example 5

Neonatal Rat Ventricular Myocytes in Culture

Cultured rat neonatal ventricular cardiomyocytes (NRVMs) were prepared as follows. Ventricles were harvested from 1- or 2-day-old Sprague-Dawley rats, and cardiomyocytes isolated by digestion with trypsin. Following digestion, the cells were pre-plated for 1 hour and supernatants were collected containing primarily cardiomyocytes, removing non-myocyte cells. Cardiomyocytes were kept in medium supplemented with 10% fetal bovine serum, antibiotics (50 µg/ml) and BrdU (0.1 mM) for 48 hours before adenoviral infection.

Example 6

Adenoviral Overexpression of BRCA1 in Isolated NRVMs

Cardiomyocytes were infected with 10MOI of a replication deficient adenoviral vector containing the CMV promoter and either human BRCA1 or a null vector (human Adenovirus Type5 dE1/E3, Vector Biolabs, USA). Following 48 hours incubation, cardiomyocytes were treated with 21 μM of doxorubicin or 50 μM of $H_2O_2$. The inhibitor of p53, pifithrin-α (10 μm, Sigma Aldrich, USA) was added 2 hrs prior to the addition of doxorubicin or hydrogen peroxide. After 24 hours, cardiomyocytes were either trypsinized and collected for flow cytometry or harvested for protein and RNA extraction.

Example 7

Flow Cytometry for AnnexinV-FITC and Propidium Iodide Staining

Following appropriate treatment, cardiomyocytes were trypsinized and collected in 1× binding buffer provided with AnnexinV-FITC Apoptosis Detection Kit (BD Biosciences, USA). Flow cytometric analyses were performed according to the manufacturer's instructions, and cells were examined within 1 hour for AnnexinV-FITC and PI staining (Beckmann Coulter, USA).

Example 8

RNA, Protein Extraction, Real-Time PCR and Western Blotting

Total RNA was isolated from NRVMs or heart using trizol (Invitrogen, USA) reagent and reverse transcribed using a commercially available kit (Quantitect Reverse Transcription Kit, Qiagen Germany). Real-time reactions were carried out with the ABI-SYBR Green master mix (ABI Systems, UK). The following primers were used (i) murine BRCA1 (forward-5'-ATCTGCCGTCCAAATTCAAG-3' (SEQ ID NO:18), reverse-5'-TTCCAAACAGATCGGACACTC-3' (SEQ ID NO:19), human BRCA1 (forward-5'-AACAGC-TACCCTTCCATCATAAGT-3' (SEQ ID NO:20), reverse-5'-GGGTATTCACTACTTTTCTGTGAAGTT-3' (SEQ ID NO:21)) and GAPDH (forward-5'-TGGATGCAGGGAT-GATGTTCT-3' (SEQ ID NO:22), reverse-5'-TGCACCAC-CAACTGCTTAGCC (SEQ ID NO:23)) as internal control. Total proteins were extracted using RIPA buffer (Sigma Aldrich, USA) and 40 μg of total lysates were resolved via SDS gel electrophoresis before being transferred to nitrocellulose membranes. The membranes were probed with antibodies for BRCA1 (Santa Cruz Biotechnology, USA), p53, phospho-p53, cleaved caspase-3 (Cell Signaling Technology, USA), TFIIB (Santa Cruz Biotechnology, USA), GAPDH and α-actin (Chemicon, USA).

Example 9

Immunoprecipitation Assay

For analysis of physical interaction between BRCA1 and p53, cardiomyocytes were maintained and treated in 6-cm culture-dishes. After adenoviral and/or stress treatments, cells were scraped and suspended in 100 μL of RIPA buffer. The total cell lysate was obtained after homogenization and centrifugation at 14,000 g for 30 minutes at 4° C. Protein concentration was determined by the Bradford assay. Aliquots of each fraction (100 μg protein for total cell lysate) were incubated with either 0.5 μg of anti-p53 mouse monoclonal antibody (Cell Signaling Technology, USA) or with 0.5 μg of anti-BRCA1 (Santa Cruz Biotechnology, USA) for 1 hour at 4° C. Addition of protein A-Sepharose (Santa Cruz Biotechnology) and incubation for 16 hours at 4° C. was followed by centrifugation and repetitive washing of the Sepharose beads. After the final wash, the beads were resuspended in 24 uL of sample buffer, and the samples were boiled, resolved by 4-12% SDS-polyacrylamide gel electrophoresis and the proteins transferred to nitrocellulose membranes. Western blot analyses was performed with anti-p53 (Cell Signaling Technology, USA) and anti-BRCA1 antibodies (Santa Cruz Biotechnology, USA). The immunoblots were probed with appropriate horseradish peroxidase-conjugated secondary antibodies and visualized with enhanced chemiluminescence (GE Healthscience, USA).

Example 10

Cells

Human umbilical vein endothelial cells (HUVECs) were purchased from Cambrex and cultured in MCDB-131 complete medium (Cambrex Corporation). After appropriate RNA interference, HUVECs were incubated with 20 ng/ml TNFα (R & D) or 2 μM doxorubicin (Sigma) before experimental protocols were initiated. These concentrations were determined from pilot optimization studies.

Example 11

RNA Interference

A BRCA1 adenovirus (ad-BRCA1) containing the complete coding sequence of human BRCA1 with the CMV promoter was purchased from Vector BioLabs. Ad-null and ad-GFP from the same source served as controls. The efficacy of adenovirus delivery was optimized by transfecting HUVECs with ad-GFP (see FIG. 19A). Optimal ratio for ad-BRCA1 transfection was determined in preliminary western blot (FIG. 19B) and real-time PCR experiments to be 20 MOI.

BRCA1 gene expression was silenced by transfection with a SMART pool BRCA1 siRNA coupled with the siPORT NeoFX transfection reagent as per the manufacturer's recommendations (Ambion). The negative control comprised a cocktail of four scrambled siRNAs. The optimal siBRCA1 concentration was determined in pilot experiments to be 10 nM. The transfection medium was removed after 24 hours and maintained for the next 24 hours in MCDB-131 complete medium before initiating experimental procedures.

Example 12

Western Blotting

Western blot analysis was performed according to standard procedures. Proteins from whole cell lysates of HUVECs were resolved on SDS-polyacrylamide gels and transferred to nitrocellulose membranes (Bio-Rad). Membranes were probed with primary antibodies from Santa Cruz (BRCA1), Cell Signaling (p53, p21, Ser1177-phospho-eNOS, Akt, Ser473-phospho-Akt, cleaved caspase-3), Chemicon (GADD45a, GAPDH) and BD (eNOS). Immunoblots were incubated with the appropriate horseradish peroxidase-asso-

Example 13

In Vitro Apoptosis Assays

Apoptotic and necrotic cell death were assessed in ad-BRCA1 and ad-null infected HUVECs by flow cytometry coupled with the BD Annexin V-FITC Apoptosis Detection Kit. Data were acquired on a Beckman Coulter Cytomics FC500 flow cytometer equipped with a 488 nm argon gas laser.

DNA extracted from ad-BRCA1 and ad-null infected HUVECs were resolved by horizontal electrophoresis. DNA fragmentation was visualized under ultraviolet light.

Example 14

Cell Cycle Analysis

Ad-BRCA1 and ad-null infected HUVECs were fixed with 70% ethanol and 100 µg/ml RNase A (Sigma) before being stained with propidium iodide (50 µg/ml, Sigma). Data on DNA content was collected with by flow cytometry and quantified with CXP software (Beckman Coulter).

Example 15

Migration Assay

The migratory function of HUVECs was determined with the CytoSelect™ 24-Well Cell Migration Fluorometric Assay (Cell Biolabs). Ad-BRCA1- or ad-null-transfected HUVECs ($0.25 \times 10^6$) were placed in the upper chambers (pore size 8 µm) in the presence or absence of TNFα (20 ng/ml). The lower chambers were filled with 10% FBS-supplemented complete MCDB-131 medium. Following 12 hours at 37° C., migratory cells were dissociated from the underside of the insert membrane, lysed and stained with the Lysis Buffer/CyQuant® GR dye solution before being fluorescently quantified. Each experiment was performed in triplicate and repeated thrice.

Example 16

Matrigel Assay

HUVEC-associated angiogenesis was measured with the In Vitro Angiogenesis Assay Kit from Chemicon. Ad-BRCA1- or ad-null-transfected HUVECs ($9 \times 10^3$) were seeded in 96-well Matrigel-coated plates. Capillary-like tube formation was examined and photographed 5 hours after seeding with an inverted microscope (Nikon). Tube formation was quantified by counting the number of tubes, branching points and network of tubes in randomly captured microscopic fields and by scoring the values for each type of structure. Each experiment was performed in triplicate and repeated thrice.

Example 17

RNA Extraction and Real-Time Quantitative PCR

Total RNA extracted from HUVECs were reverse transcribed for quantitative assessment of VCAM1, ICAM1, E-selectin and VEGFa expressions by real-time PCR using the primer pairs listed in Table 4.

TABLE 4

| Primer Pairs | |
|---|---|
| Gene primer pairs | Sequences |
| ICAM1- Forward | 5'-TGATGGGCAGTCAACAGCTA-3' (SEQ ID NO: 24) |
| ICAM1- Reverse | 5'-AGGGTAAGGTTCTTGCCCAC-3' (SEQ ID NO: 25) |
| VCAM1- Forward | 5'-TGGGAAAAACAGAAAAGAGGTG-3'(SEQ ID NO: 26) |
| VCAM1- Reverse | 5'-GTCTCCAATCTGAGCAGCAA-3' (SEQ ID NO: 27) |
| E-Selectin- Forward | 5'-AAGCCTTGAATCAGACGGAA-3' (SEQ ID NO: 28) |
| E-Selectin- Reverse | 5'-TCCCTCTAGTTCCCCAGATG-3' (SEQ ID NO: 29) |
| VEGFa- Forward | 5'-CTACCTCCACCATGCCAAGT-3' (SEQ ID NO: 30) |
| VEGFa- Reverse | 5'-AGCTGCGCTGATAGACATCC-3' (SEQ ID NO: 31) |
| GAPDH- Forward | 5'-CACCAGGGCTGCTTTTAACTCTGGTA-3' (SEQ ID NO: 32) |
| GAPDH- Reverse | 5'-CCTTGACGGTGCCATGGAATTTGC-3' (SEQ ID NO: 33) |

PCR reactions were performed on the ABI PRISM 7900HT system (Applied Biosystems) with GAPDH acting as the housekeeping control.

Example 18

Mouse Hindlimb Ischemia

Unilateral hindlimb ischemia was performed on anaesthetized 8-week old male Balb/c mice. Briefly, the left femoral artery was ligated and excised distal to the origin of the deep femoral artery but proximal to the popliteal artery. Immediately following the surgical procedure, 20 µl of $10^{10}$ PFU/ml ad-BRCA1 or ad-GFP were injected intramuscularly at five locations of the left adductor muscle. Blood flow in the feet was assessed upon completion of the surgery and on post-operative days 4, 8, 16 and 28 by laser Doppler flow imaging. Perfusion recovery was expressed as the recovery of blood flow to the ischemic foot normalized to that in the contralateral foot.

Following 28 days of ischemia, gastrocnemius muscles were harvested, frozen and embedded in OCT for cryosectioning (7 μm). Sections were subsequently stained with hematoxylin and eosin. Antibodies targeting isolectin B4, TOPRO-3A and α-smooth muscle actin were used to identify endothelial cells, nuclei and arterioles respectively. Capillary density was determined in at least ten independent fields by fluorescence microscopy.

Example 19

Statistical Analysis

Where appropriate, means were compared by the Student's t test. Differences between multiple means were evaluated by analysis of variance (ANOVA) and post hoc Bonferroni test. A probability value of less than 0.05 was taken as statistically significance.

What is claimed is:

1. A method for inhibiting or decreasing cardiomyocyte apoptosis associated with cardiotoxic chemotherapeutic treatment in a subject receiving a cardiotoxic chemotherapeutic agent causing cardiomyocyte apoptosis, said method comprising delivering BRCA1 polynucleotide operably linked to a promoter to the heart of the subject so that BRCA1 is expressed in cardiomyocytes thereby inhibiting or decreasing cardiomyocyte apoptosis associated with administration of the cardiotoxic chemotherapeutic treatment to said subject, wherein the BRCA1 polynucleotide comprises (a) human BRCA1 gene (SEQ ID NO:1) or an isoform selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12; b) a nucleotide sequence encoding the full-length BRCA1 polypeptide encoded by human BRCA1 gene (SEQ ID NO:1) or by an isoform selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12; or (c) a nucleotide sequence complementary to (a) or (b).

2. A method for inhibiting or decreasing cardiomyocyte apoptosis associated with cardiotoxic chemotherapeutic treatment in a subject receiving a cardiotoxic chemotherapeutic agent causing cardiomyocyte apoptosis, said method comprising delivering BRCA1 polynucleotide operably linked to a promoter to the heart of the subject so that BRCA1 is expressed in cardiomyocytes thereby inhibiting or decreasing cardiomyocyte apoptosis associated with administration of the cardiotoxic chemotherapeutic treatment to said subject, wherein the BRCA1 polynucleotide comprises (a) human BRCA1 gene (SEQ ID NO:1); (b) a nucleotide sequence encoding the full-length BRCA1 polypeptide encoded by human BRCA1 gene (SEQ ID NO:1); or (c) a nucleotide sequence complementary to (a) or (b).

3. The method of claim 1 wherein the polynucleotide is incorporated into a vector for delivery.

4. The method of claim 3 wherein the vector is a viral vector.

5. The method of claim 3 wherein the vector is a nonviral vector.

6. The method of claim 1 wherein the polynucleotide is delivered as naked DNA.

7. The method of claim 1 wherein the BRCA1 polynucleotide is delivered in combination with an existing patient care paradigm for cardiovascular disease.

8. The method of claim 7 wherein the existing patient care paradigm is selected from the group consisting of statins, ACE inhibitors, angiotensin receptor blockers, antihyperlipidemics and antihyperglycaemics.

9. The method of claim 1 wherein the cardiotoxic chemotherapeutic treatment is doxorubicin.

10. The method of claim 1 wherein the BRCA1 polynucleotide is delivered at the same time as administration of the cardiotoxic chemotherapeutic agent.

11. The method of claim 1 wherein the BRCA1 polynucleotide encodes a BRCA1 protein that maintains tumor suppressor activity.

12. The method of claim 4 wherein the viral vector is an adenovirus or adenovirus-associated vector.

13. The method of claim 3 wherein the vector comprises a cis-acting enhancer operably linked to the promoter.

14. The method of claim 1 wherein from 500 to 16,000 μg of said BRCA1 polynucleotide are delivered to the subject in a single session.

15. The method of claim 1 wherein from 500 to 16,000 μg of said BRCA1 polynucleotide are delivered to the subject in multiple sessions.

16. The method of claim 2 wherein the polynucleotide is incorporated into a vector for delivery.

17. The method of claim 2 wherein the polynucleotide is delivered as naked DNA.

18. The method of claim 2 wherein the BRCA1 polynucleotide is delivered in combination with an existing patient care paradigm for cardiovascular disease.

19. The method of claim 2 wherein the BRCA1 polynucleotide is delivered at the same time as administration of the cardiotoxic chemotherapeutic agent.

20. The method of claim 2 wherein from 500 to 16,000 μg of said BRCA1 polynucleotide are delivered to the subject in a single session.

21. The method of claim 2 wherein from 500 to 16,000 μg of said BRCA1 polynucleotide are delivered to the subject in multiple sessions.

* * * * *